(12) United States Patent
Gupta et al.

(10) Patent No.: US 11,141,114 B2
(45) Date of Patent: Oct. 12, 2021

(54) METHOD AND APPARATUS FOR WIDE-BAND PHASE GRADIENT SIGNAL ACQUISITION

(71) Applicant: Analytics For Life Inc., Toronto (CA)

(72) Inventors: Sunny Gupta, Amherstview (CA); Konstantin Papirov, Richmond Hill (CA); Jason Woo, Thornhill (CA)

(73) Assignee: Analytics for Life Inc., Toronto (CA)

( * ) Notice: Subject to any disclaimer, the term of this patent is extended or adjusted under 35 U.S.C. 154(b) by 498 days.

(21) Appl. No.: 15/911,047

(22) Filed: Mar. 2, 2018

(65) Prior Publication Data

US 2018/0249960 A1 Sep. 6, 2018

Related U.S. Application Data

(60) Provisional application No. 62/466,322, filed on Mar. 2, 2017.

(51) Int. Cl.
*A61B 5/30* (2021.01)
*A61B 5/00* (2006.01)
(Continued)

(52) U.S. Cl.
CPC ............ *A61B 5/7203* (2013.01); *A61B 5/291* (2021.01); *A61B 5/30* (2021.01); *A61B 5/316* (2021.01); *A61B 5/7225* (2013.01); *A61B 5/0006* (2013.01)

(58) Field of Classification Search
CPC . A61B 5/0006; A61B 5/04017; A61B 5/0428; A61B 5/0478; A61B 5/7203; A61B 5/7225
See application file for complete search history.

(56) References Cited

U.S. PATENT DOCUMENTS

| 5,020,540 A | 6/1991 | Chamoun |
| 5,243,993 A | 9/1993 | Alexander et al. |

(Continued)

FOREIGN PATENT DOCUMENTS

| JP | 05-220121 | 8/1993 |
| JP | 2001-190510 | 7/2001 |

(Continued)

OTHER PUBLICATIONS

Asadi, F., et al., "Cardiac Arrhythmia Recognition with Robust Discrete Wavelet-Based and Geometrical Feature Extraction via Classifiers of SVM and MLP-BP and PNN Neural Networks," Computing in Cardiology, Issue 43, 2015, pp. 933-936.

(Continued)

*Primary Examiner* — Amanda K Hulbert
(74) *Attorney, Agent, or Firm* — Meunier Carlin & Curfman LLC

(57) ABSTRACT

The present disclosure facilitates capture (e.g., bipolar capture) of differentially-acquired wide-band phase gradient signals (e.g., wide-band cardiac phase gradient signals, wide-band cerebral phase gradient signals) that are simultaneously sampled. Notably, the exemplified system minimizes non-linear distortions (e.g., those that can be introduced via certain filters such as phase distortions) in the acquired wide-band phase gradient signals so as to not affect the information therein that can non-deterministically affect analysis of the wide-band phase gradient signal in the phase space domain. Further, a shield drive circuit and shield-drive voltage plane may be used to facilitate low noise and low interference operation of the acquisition system.

22 Claims, 41 Drawing Sheets

(51) Int. Cl.
*A61B 5/291* (2021.01)
*A61B 5/316* (2021.01)

(56) References Cited

U.S. PATENT DOCUMENTS

| | | |
|---|---|---|
| 5,823,957 A | 10/1998 | Faupel et al. |
| 5,954,660 A | 9/1999 | Legay et al. |
| 6,014,582 A | 1/2000 | He |
| 8,521,266 B2 | 8/2013 | Narayan et al. |
| 8,923,958 B2 | 12/2014 | Gupta et al. |
| 9,289,150 B1 | 3/2016 | Gupta et al. |
| 9,408,543 B1 | 8/2016 | Gupta et al. |
| 9,597,021 B1 | 3/2017 | Gupta et al. |
| 9,655,536 B2 | 5/2017 | Gupta et al. |
| 9,737,229 B1 | 8/2017 | Gupta et al. |
| 2001/0008953 A1 | 7/2001 | Honda et al. |
| 2002/0029068 A1 | 3/2002 | Lyster et al. |
| 2003/0105403 A1 | 6/2003 | Istvan et al. |
| 2006/0173364 A1 | 8/2006 | Clancy et al. |
| 2006/0178706 A1 | 8/2006 | Lisogurski et al. |
| 2013/0023781 A1 | 1/2013 | Freeman et al. |
| 2013/0303871 A1 | 11/2013 | Brest Van Kempen et al. |
| 2014/0194758 A1 | 7/2014 | Korenberg et al. |
| 2014/0375298 A1 | 12/2014 | Garcia et al. |
| 2015/0133803 A1 | 5/2015 | Gupta et al. |
| 2015/0216426 A1 | 8/2015 | Burton et al. |
| 2016/0378936 A1 | 12/2016 | Burton et al. |
| 2017/0119272 A1 | 5/2017 | Gupta et al. |
| 2018/0000371 A1 | 1/2018 | Gupta et al. |
| 2018/0078146 A1 | 3/2018 | Shadforth et al. |

FOREIGN PATENT DOCUMENTS

| | | |
|---|---|---|
| JP | 2006-500964 | 1/2006 |
| JP | 2006-218304 | 8/2006 |
| JP | 2015-513413 | 5/2015 |
| WO | 2003/047427 | 6/2003 |
| WO | 2013/120014 | 8/2013 |
| WO | 2017/033164 | 3/2017 |

OTHER PUBLICATIONS

Itu, L., et al., "A machine-learning approach for computation of fractional flow reserve from coronary computed tomography," Journal of Applied Physiology, vol. 121, No. 1, 2016, pp. 42-52.

Khan, M., et al., "Wavelet Based ECG Denoising Using Signal-Noise Residue Method," 5th International Conference on Bioinformatics and Biomedical Engineering, May, 4 pages.

McKee, James J., et al., "Sigma-Delta Analogue-to-Digital Converters for ECG Signal Acquisition," Proceedings of 18th Annual International Conference of the IEEE Engineering in Medicine and Biology Society, Amsterdam, Netherlands, Oct. 31-Nov. 3, 1996, pp. 19-20.

International Search Report and Written Opinion issued for International Application No. PCT/IB2018/051358, dated Jun. 18, 2018, 17 pages.

International Search Report and Written Opinion issued for International Application No. PCT/IB2016/055125, dated Nov. 21, 2017.

International Preliminary Report on Patentability issued for International Application No. PCT/IB2016/055125, dated Mar. 8, 2018.

Jobbagy et al. "Biomedical Instrumentation", Typotex Kiado, Budapest University of Technology and Economics, Mar. 31, 2015, pp. 1-241.

Ha, S., et al., "Integrated Circuits and Electrode Interfaces for Noninvasive Physiological Monitoring," IEEE Transactions on Biomedical Engineering, vol. 61, No. 5, 2014, pp. 1522-1537.

Supplementary Partial Search Report, dated Nov. 20, 2020, received in connection with corresponding EP Patent Application No. 18761936.6.

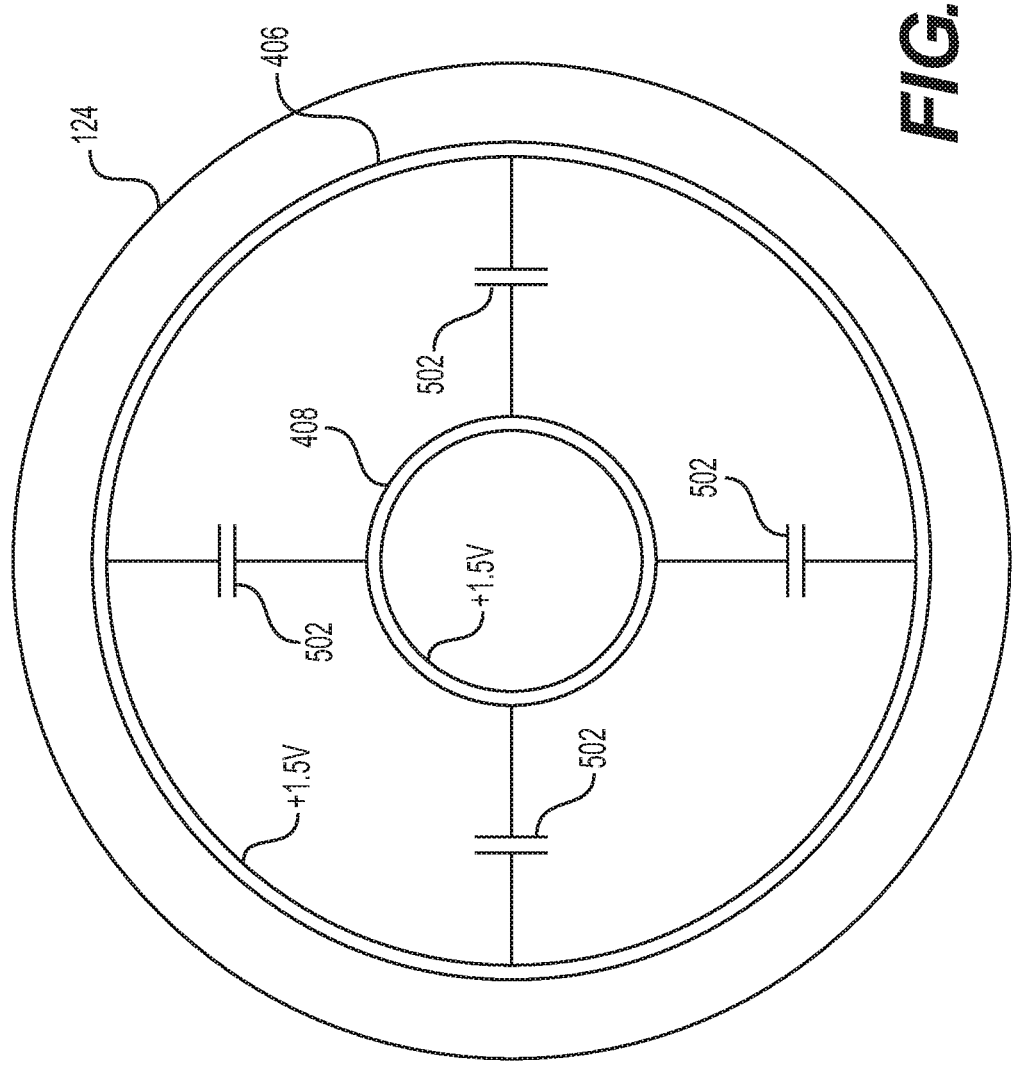

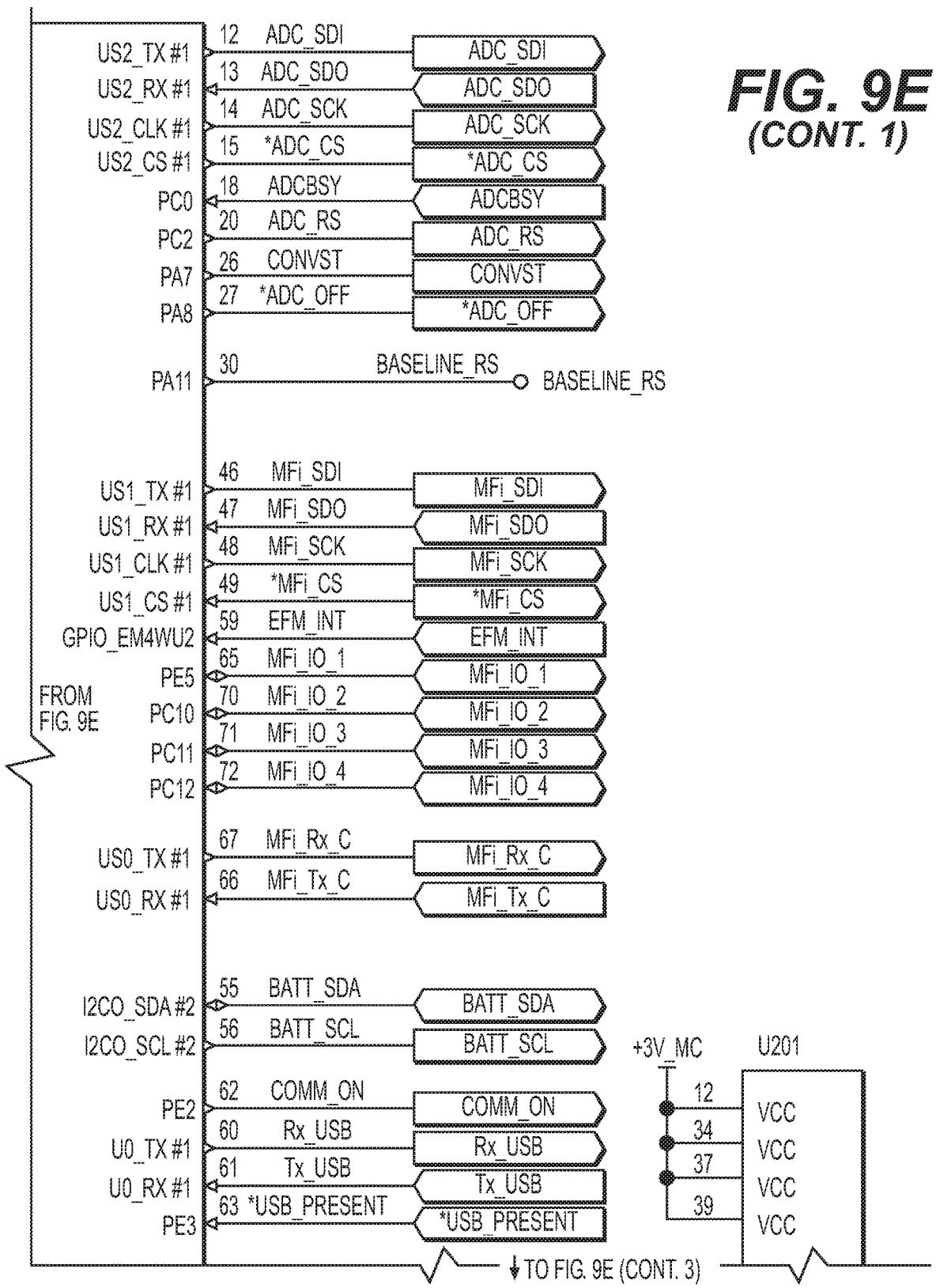
FIG. 9E (CONT. 1)

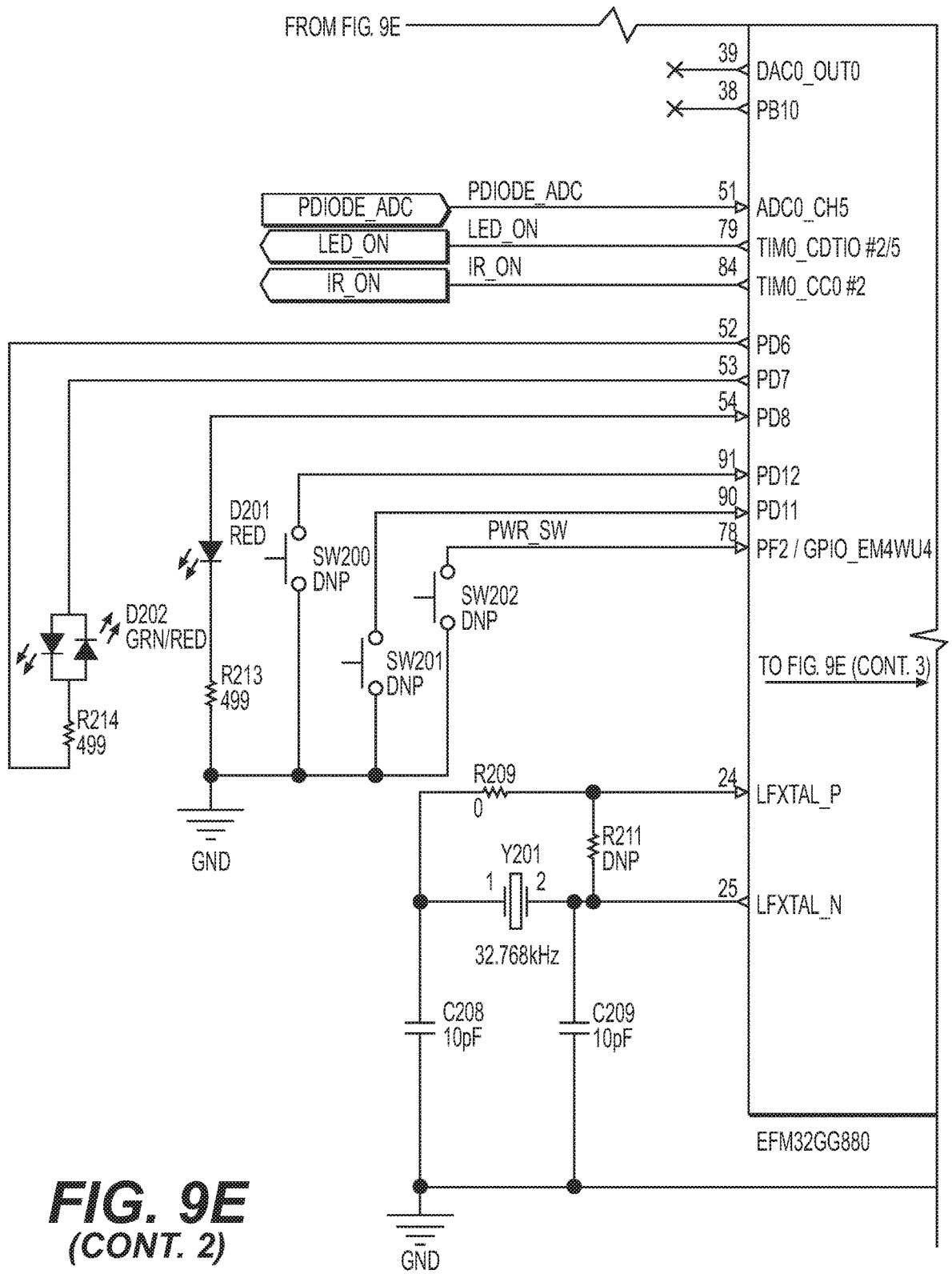
FIG. 9E (CONT. 2)

(CONT. 3)

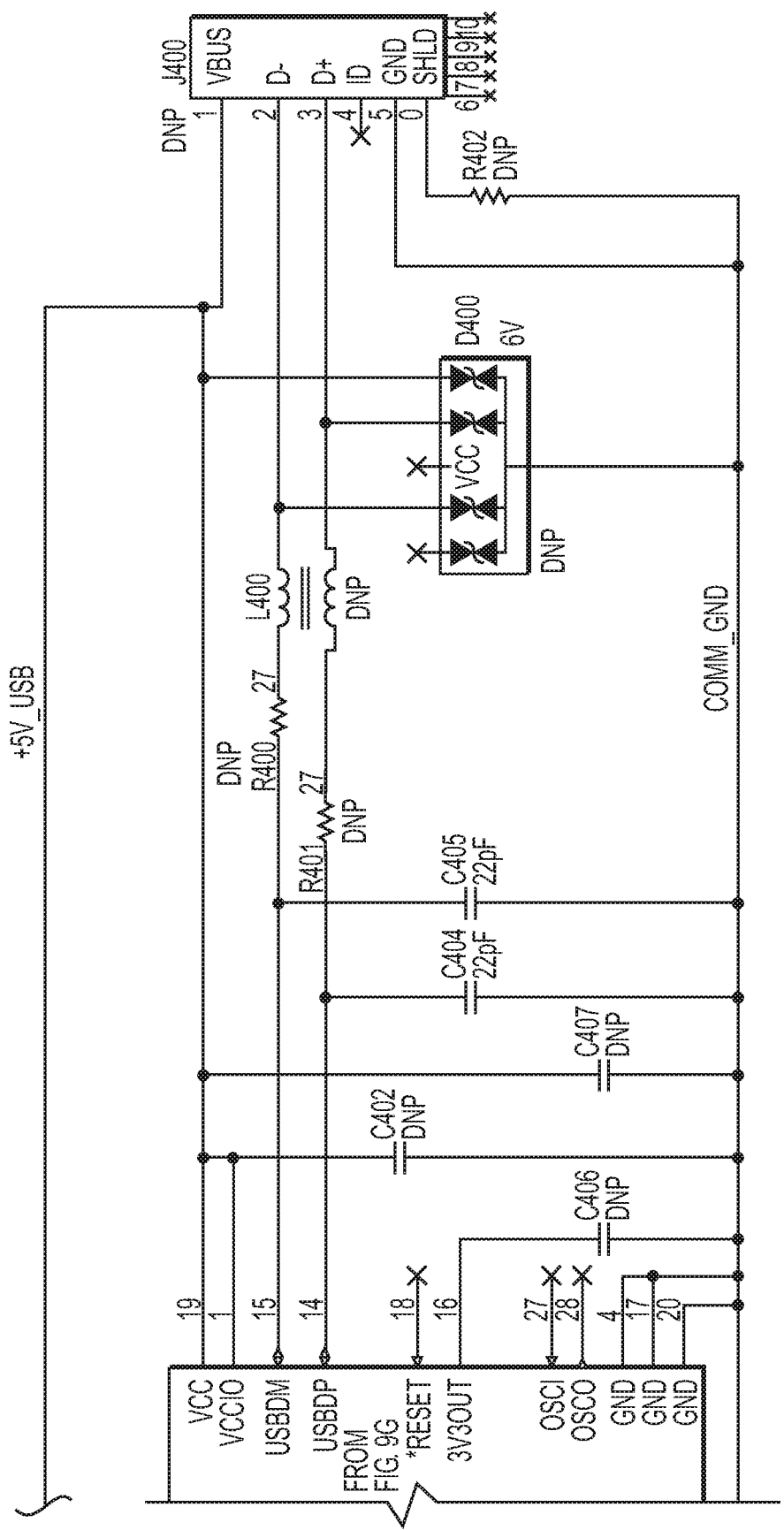

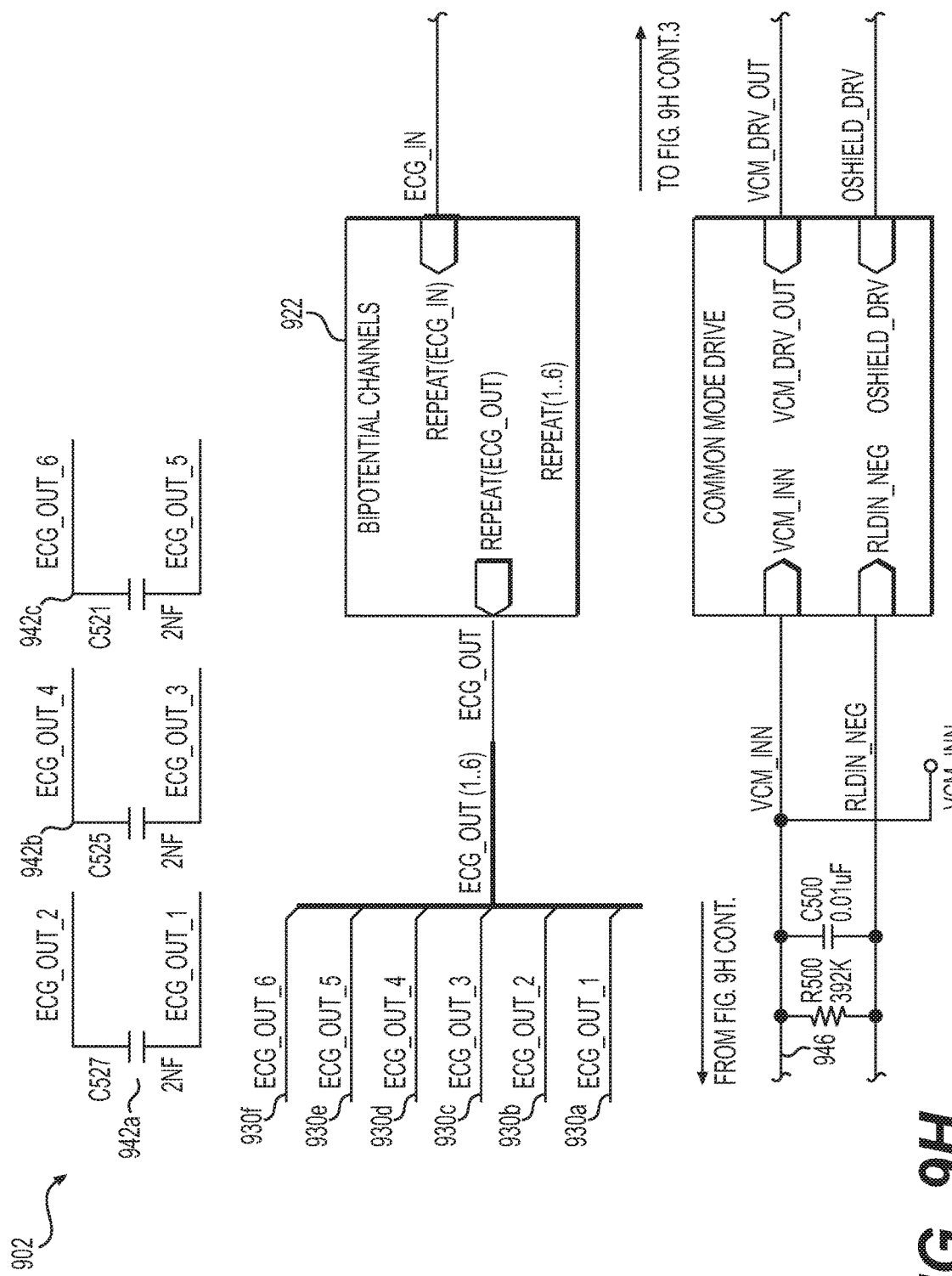
FIG. 9H (CONT.2)

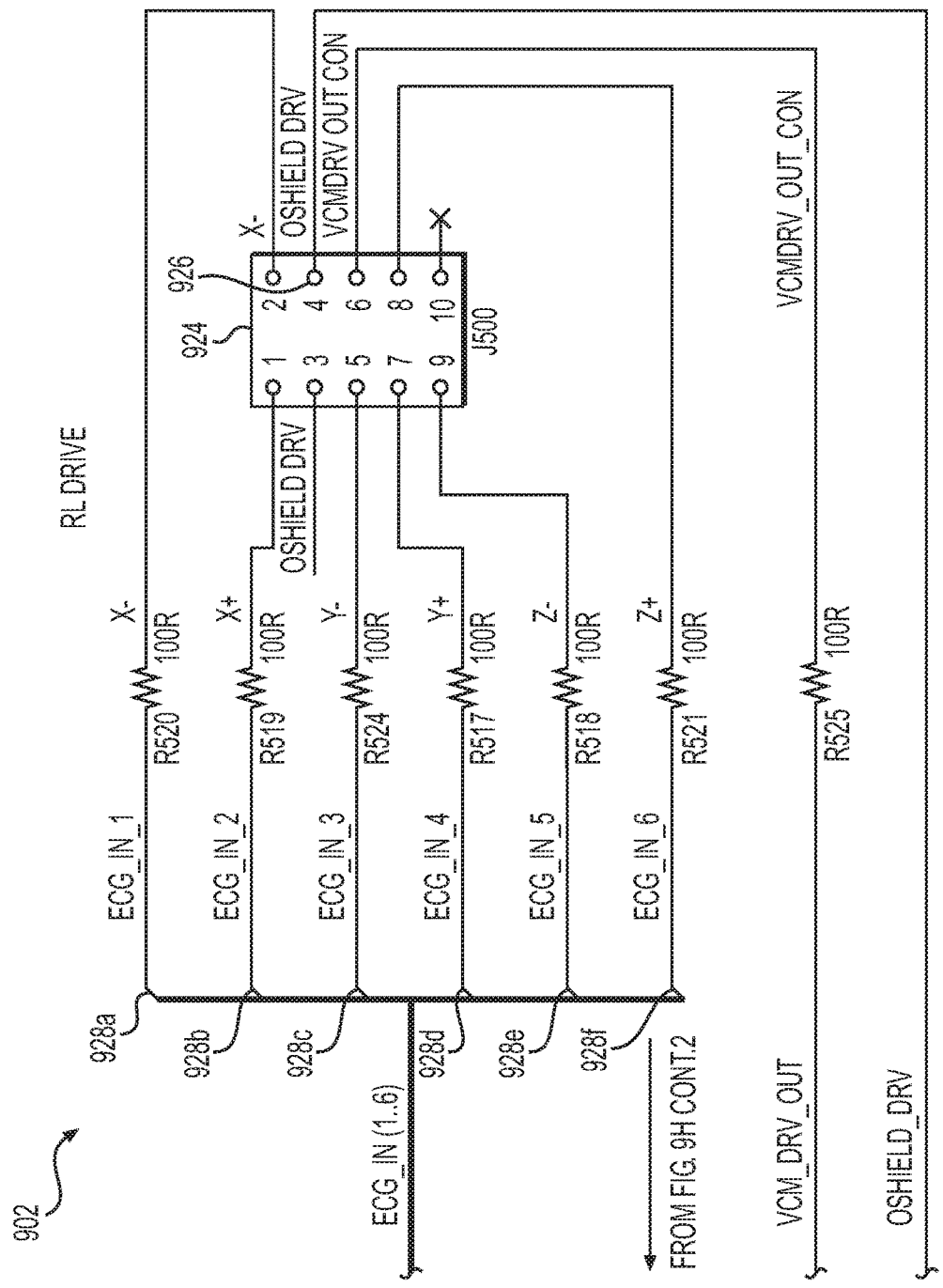
FIG. 9H (CONT.3)

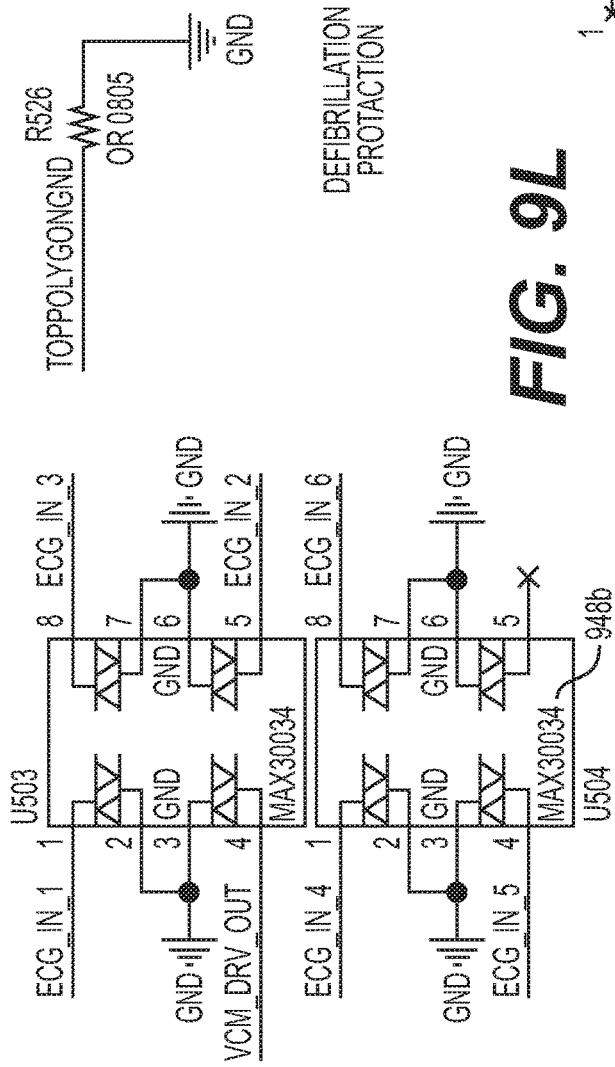
FIG. 9L
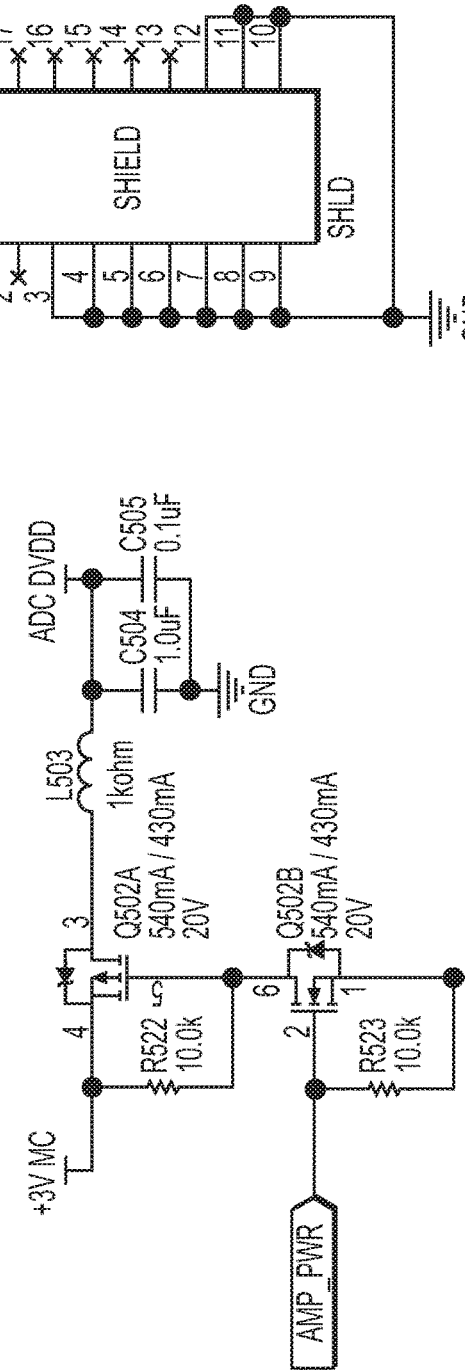
FIG. 9N
FIG. 9M 30-0066-REV2 - LAYER 1
30-0066-REV2 - LAYER 3
30-0066-REV2 - LAYER 4
30-0066-REV2 - LAYER 6

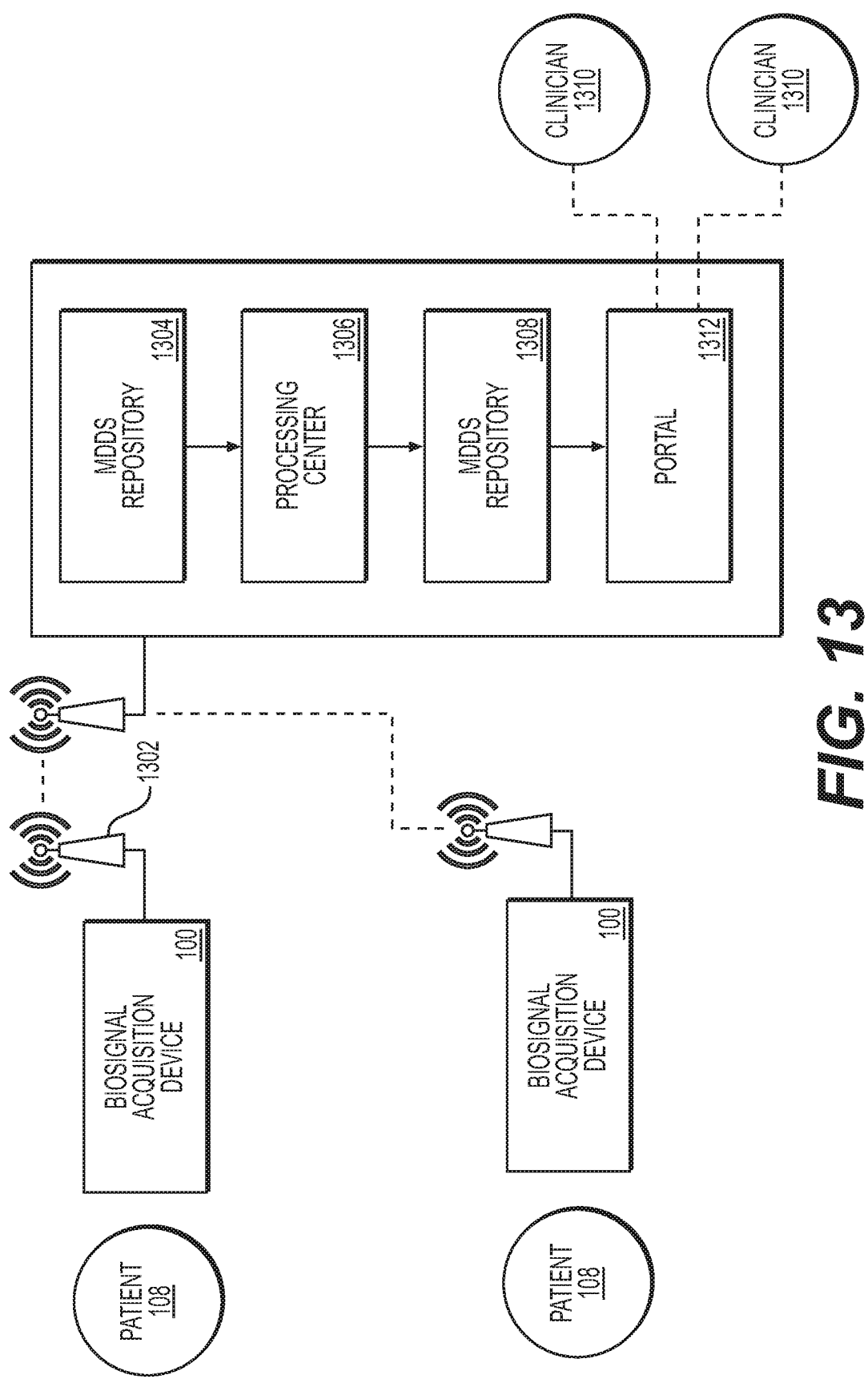

METHOD AND APPARATUS FOR WIDE-BAND PHASE GRADIENT SIGNAL ACQUISITION

RELATED APPLICATION

This application claims priority to, and the benefit of, U.S. Provisional Application No. 62/466,322, filed Mar. 2, 2017, entitled "Method and Apparatus for Wide-Phase Gradient Signal Acquisition," which is incorporated by reference herein in its entirety.

TECHNICAL FIELD

The present disclosure generally relates to a biosignal acquisition apparatus that differentially acquires wide-band phase gradient signals that are used to non-invasively estimate functions of the body such as heart functions, as well as to pinpoint and distinguish disease (e.g., to predict presence or non-presence of a disease).

BACKGROUND

Conventional electrocardiographic instruments are configured to acquire and record biosignals such as biopotential signals relating to electrical activities of the heart. It is conventionally accepted that a large fraction of the total signal collected by such instruments is considered devoid of biological information. However, hidden within the full spectrum of physiologic signals emitted from the human body are information that can be used to pinpoint and distinguish disease.

Because these information can be captured in physiologic signals having signal power comparable to, or lower than, the noise floor of conventional electrocardiographic instruments, such information are difficult to extract, or not discernible, from the measured signals of these instruments. In some instances, the signal of interests has an order of magnitude of a few micro-Volts, and in other instances, even smaller. At such levels, interference from external energy sources such as man-made radiofrequency transmission and those that occur naturally as well as those from internal circuitries of the measurement instrument itself can affect the acquisition and recording of such information.

What are needed are devices, systems and methods that overcome challenges in the present art, some of which are described above.

SUMMARY

The present disclosure facilitates capture (e.g., bipolar capture) of differentially-acquired wide-band phase gradient signals (e.g., wide-band cardiac phase gradient signals, wide-band cerebral phase gradient signals) that are simultaneously sampled, in some embodiments, having a temporal skew among the channels of less than about 1 µs, and in other embodiments, having a temporal skew of not more than about 10 femtoseconds. Notably, the exemplified system minimizes non-linear distortions (e.g., those that can be introduced via certain filters such as phase distortions) in the acquired wide-band phase gradient signals so as to not affect the information therein that can non-deterministically affect analysis of the wide-band phase gradient signal in the phase space domain.

The bipolar capture operation, for use in differential measurements, increases the dynamic range of the differential measurement input so as to reduce, or eliminate, a need for filtering (e.g., low frequency filtering), thereby improving acquisition of the acquired wide-band phase gradient signals by further minimizing potential non-linear distortions that may be introduced from additional hardware circuitry associated with such filtering. The bipolar capture operation, of a differential measurement, also reduce or eliminate common mode noise, via use of a single amplifier, as compared to a pair of amplifiers that capture unipolar signals where common mode noise reduction is based on tolerances of resistors and capacitors and symmetry of the amplifiers (e.g., op-amps).

Further, a shield drive circuit and shield-drive voltage plane may be used to facilitate low noise and low interference operation of the acquisition system. In some embodiments, the acquisition system has a noise performance of better than 10 µV.

In an aspect, an apparatus (e.g., a BioSignal Acquisition Instrument (a "BSA instrument")) is disclosed. The apparatus includes a plurality of biosignal acquisition channels (e.g., three channels) in which each biosignal acquisition channel comprises a gain amplifier configured to, by bipolar sensing for each input (of a differential input pair), differentially amplify biopotential signals received from a pair of associated surface electrodes placed on a patient (including mammals such as human and test animals) to generate a differentially-acquired wide-band phase gradient signal (e.g., differential wide-band cardiac gradient signal), wherein each differential biopotential signal is amplified without filtering that causes distortion in the generated differential wide-band cardiac phase gradient signal above about 1 kHz, wherein each output of the biosignal acquisition channels feeds an analog-to-digital conversion circuit that simultaneously samples (e.g., having a temporal skew among the channels of less than about 1 µs or having a temporal skew of not more than about 10 femtoseconds) each of the biosignal acquisition channels (e.g., having at a sampling frequency above about 10 KHz, e.g., about 40 Khz, about 80 KHz, about 500 Khz, or higher) to generate a differential wide-band cardiac phase gradient signal data stream.

In some embodiments, the apparatus further includes a potential biasing circuit that actively applies a varying potential to a patient so as to shunt environmental noise currents flowing over or in the patient. In some embodiments, the potential biasing circuit applies a constant positive potential to the patient. In some embodiments, the potential biasing circuit drives the patient to a constant negative potential. In some embodiments, the potential biasing circuit drives the patient to a varying potential.

In some embodiments, the apparatus includes a potential biasing circuit that actively applies a potential (e.g., a constant potential, e.g., about 1.5 $V_{DC}$ or a varying potential that varies about $-1.5\ V_{AC\_rms}$) to the patient so as to shunt environmental noise currents flowing over or in the patient. In some embodiments, the applied varying potential has a value of about 2.0 $V_{AC\_rms}$, about 1.8 $V_{AC\_rms}$, about 1.6 $V_{AC\_rms}$, about 1.4 $V_{AC\_rms}$, about 1.2 $V_{AC\_rms}$, about 1.0 $V_{AC\_rms}$, about 0.8 $V_{AC\_rms}$, about 0.6 $V_{AC\_rms}$, about 0.4 $V_{AC\_rms}$, about 0.2 $V_{AC\_rms}$, about $-0.2\ V_{AC\_rms}$, about $-0.4\ V_{AC\_rms}$, about $-0.6\ V_{AC\_rms}$, about $-0.8\ V_{AC\_rms}$, about $-1.0\ V_{AC\_rms}$, about $-1.2\ V_{AC\_rms}$, about $-1.4\ V_{AC\_rms}$, about $-1.6\ V_{AC\_rms}$, about $-1.8\ V_{AC\_rms}$, and about $-2.0\ V_{AC\_rms}$. In some embodiments, the applied potential has a value of about +0.5 $V_{DC}$, about +1.0 $V_{DC}$, about +1.5 $V_{DC}$, about +2.0 $V_{DC}$, +2.5 $V_{DC}$, about +3.0 $V_{DC}$, about +3.5 $V_{DC}$, about +4.0 $V_{DC}$, about +4.5 $V_{DC}$, about +5.0 $V_{DC}$, about $-0.5\ V_{DC}$, about $-1.0\ V_{DC}$, about $-1.5\ V_{DC}$, about $-2.0\ V_{DC}$, −2.5 V$_{DC}$, about −3.0 V$_{DC}$, about −3.5 V$_{DC}$, about −4.0 V$_{DC}$, about −4.5 V$_{DC}$, about −5.0 V$_{DC}$.

In some embodiments, the potential biasing circuit includes a waveform generator (e.g., a configurable waveform generator); and a drive circuit (e.g., a common mode amplifier) that couples to the waveform generator to actively apply an alternating potential (e.g., between about −1.0 VDC and about −2.0 VDC or between about +1.0 and about +2.0 VDC) to the patient so as to shunt environmental noise currents flowing in the patient.

In some embodiments, the potential biasing circuit actively applies an alternating potential having a minimum magnitude greater than a DC bias value associated with one or more of the surface electrodes placed on the patient (e.g., wherein the one or more surface electrodes have a half-cell potential).

In some embodiments, the apparatus includes a potential biasing circuit that actively applies a varying potential on a patient so as to shunt environmental noise currents flowing on or in the patient, wherein a substantial portion (e.g., greater than about 75%) of the varying potential is negative.

In some embodiments, the apparatus includes a potential biasing circuit that actively applies a constant potential to a patient so as to shunt environmental noise currents flowing on or in the patient.

In some embodiments, the apparatus includes a terminal block (e.g., for a given cable) comprising at least one connector configured to couple to a cable associated with a given surface electrode, wherein the cable comprises a shield layer that encapsulates one or more signal wires that carries a given biopotential signal received from the given surface electrode (e.g., wherein the shield layer does not terminate at or connect to the surface electrode); and a noise-rejection circuit (e.g., a unity gain amplifier) that applies a potential of the potential biasing circuit to the shield layer of the cable and to a cable-shield drive voltage plane to allow for return pass for noisy current induced on the shield layer.

In some embodiments, the apparatus includes one or more terminal blocks each of which individually couples to a shield of a cable associated with a surface electrode; and a shield-equalizing circuit that injects a signal carried in the cable to the shield of the cable such that the injected signal approximately matches (e.g., within at least about 90%) the signal carried in the cable.

In some embodiments, the gain amplifier of each of the biosignal acquisition channels directly couples to a terminal block (e.g., for a given cable) comprising a plurality of connectors, each of which couples a cable associated with a given surface electrode.

In some embodiments, each of the biosignal acquisition channels comprises a gain amplifier configured to amplify the received biopotential signal with a gain that provides a measurement resolution, with the analog-to-digital circuit, greater than about 0.3 µV per bit (e.g., wherein the analog-to-digital circuit provides a bit resolution of at least about 12 bits).

In some embodiments, the gain amplifier is powered by a single voltage supply (e.g., about +1.5 V$_{DC}$, about +3 V$_{DC}$, about +3.3 V$_{DC}$, about +5 V$_{DC}$, about +12 V$_{DC}$, and about +15 V$_{DC}$, about −1.5 V$_{DC}$, about −3 V$_{DC}$, about −3.3V$_{DC}$, about −5 V$_{DC}$, about −12 V$_{DC}$, and about −15 V$_{DC}$).

In some embodiments, the biopotential channels comprises a number of channels selected from the group consisting of 2, 3, 4, 5, 6, 7, 8, 9, 10, 11, and 12 (e.g., wherein the number of cables and surface electrodes corresponds to one-half the number of channels plus one, e.g., a common mode reference cable and surface electrode).

In some embodiments, the analog-to-digital circuit of each biosignal acquisition channel is configured to sample a wide-band cardiac phase gradient signal over a pre-defined voltage range of at least about 5 milli-Volt (mV) at a resolution of less than about 2 micro-Volt (µV) per bit and at a rate greater than about 5000 Hertz, wherein the biosignal acquisition channels are simultaneously sampled with a temporal skew between channels less than 1 micro-seconds (µs), and wherein each biosignal acquisition channel comprises a signal-to-noise ratio of greater than about 15 dB (e.g., greater than 20 dB).

In some embodiments, each biosignal acquisition channel comprises a gain amplifier circuit (e.g., a gain amplifier circuit board or flex circuit) that directly couples to given surface electrode within an electrode housing.

In some embodiments, each gain amplifier circuit associated with a given electrode housing feeds a corresponding analog-to-digital circuit located in a second housing, the second housing being connected to the given electrode housing via a cable.

In some embodiments, the apparatus further comprising: a plurality of analog-to-digital circuits, each corresponding to a bio-signal acquisition channel, wherein each output of the each bio-signal acquisition channel feeds a corresponding analog-to-digital circuit, and wherein the analog-to-digital circuits simultaneously sample to generate a plurality of wide-band cardiac phase gradient signal data streams each associated with a given differential wide-band cardiac phase gradient signal.

In another aspect, a method is disclosed of generating wide-band cardiac phase gradient signal data. The method includes differentially amplifying (e.g., a gain amplifier circuit) acquired biopotential signals received from a plurality of surface electrodes each placed on a patient to generate a wide-band cardiac phase gradient signal, wherein each differential biopotential signal is amplified without filtering that causes distortions in the generated differential wide-band cardiac phase gradient signal above about 1 kHz, and wherein each input of the paired differential input is configured for bi-polar sensing; and simultaneously sampling (e.g., AD converters), at a sampling frequency greater than about 50 KHz, each of the amplified differential wide-band cardiac phase gradient signals to generate differential wide-band cardiac phase gradient signal data streams, wherein the amplified differential wide-band cardiac phase gradient signals are simultaneous sampled so as to have a temporal skew among each of the amplified wide-band cardiac phase gradient signals less than about 1 µs.

In another aspect, a signal acquisition board is disclosed. The signal acquisition board includes a multi-layer printed circuit board comprising: a first layer that serves as a reference ground plane; a second layer co-planar to the first layer that serves as a cable-drive voltage plane (e.g., having a potential of about +1.5V); and one or more signal layers having a pair of conductive traces (e.g., low-impedance traces) running substantially therethrough and across one or more regions coincident and coplanar to the second layer, wherein the pair of conductive traces electrically couple, across a connector directly or indirectly affixed to the multi-layer printed circuit, ends of at least two signal-carrying conductors to differential input pins of an analog-to-digital conversion and amplifier stage mounted on a surface of the multi-layer printed circuit, wherein a first signal-carrying conductor of the at least two signal-carrying conductors is associated with a first cable and a second signal-carrying conductor of the at least two signal-carrying conductors is associated with a second cable; wherein the second layer electrically couples, over the at least one connector, i) a first outer conductor that serves as an outer shield of the first cable and ii) a second outer conductor that serves as an outer shield of the second cable, so as to drive potentials of the first outer conductor and the second outer conductor to that of the cable-drive voltage plane.

In some embodiments, the first cable and the second cable terminate at a single cable-pin connector, the single cable-pin connector having a coupling element configured to releasably mate to the connector of the signal acquisition board.

In some embodiments, the pair of conductive traces are arranged, on a same set of signal layers of the one or more signal layers, and in close proximity to one another such that substantial lengths of each conductive trace of the pair of conductive traces are substantially parallel to one another.

In some embodiments, each conductive trace of the pair of conductive traces has a length and have a same number of via so as to have a substantially similar impedance characteristics as one another.

In some embodiments, each conductive trace of the pair of conductive traces includes an impedance element (e.g., a single 10 kΩ resistor) arranged between a respective pin of the connector and a respective differential input pins of the analog-to-digital conversion circuit, and wherein the pair of conductive traces has a capacitance element coupled therebetween to form, with the impedance elements, an antialiasing filter.

In some embodiments, the multi-layer printed circuit board further comprises a conductive housing that serves as a grounded shield cage, wherein the conductive housing spans a portion of the second layer so as to encapsulate a substantial portion of the pair of conductive traces, and wherein the conductive housing is affixed to the surface of the multi-layer printed circuit and is electrically coupled to the reference ground plane.

In some embodiments, the analog-to-digital conversion and amplifier stage comprises a single integrated circuit having one or more analog-to-digital converters (ADCs) with built-in programmable gain amplifiers (PGAs).

In some embodiments, the analog-to-digital conversion and amplifier stage for the pair of conductive traces comprises an analog-to-digital converters (ADCs) integrated circuit coupled to an amplifier circuit.

In some embodiments, the multi-layer printed circuit board further comprises: one or more processors and one or more memory components coupled to the one or more processors, wherein the one or more processors and the one or more memory components are arranged on a portion of the surface of the multi-layer printed circuit that do not coincide or overlap with the cable-drive voltage plane of the second layer.

In some embodiments, the pair of conductive traces forms a part of a first differential input channel of the signal acquisition board.

In some embodiments, the signal acquisition board of claim further comprises a second differential input channel and a third differential input channel, wherein each of the second differential input channel and the third differential input channel comprises a pair of conductive traces running substantially through the one or more signal layers across the one or more regions coincident and coplanar to the cable-drive voltage plane of the second layer, wherein each of the second differential input channel and the third differential input channel connects to a pair of cables having at least one signal-carrying conductor and an outer conductor that serves as an outer shield of the signal-carrying conductor, and wherein the cable-drive voltage plane electrically couples, over the at least one connector, to the outer conductors of the pair of cables so as to drive potentials of the outer conductors to that of the cable-drive voltage plane.

BRIEF DESCRIPTION OF DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIG. 5 is a diagram of a method of matching potential of a signal-carrying conductor and a shield-conductor in accordance with an embodiment.

FIGS. 9A, 9B, 9C, 9D, 9E, 9F, 9G, 9H, 9I, 9J, 9K, 9L, 9M, 9N, 9O, 9P, 9Q, 9R, 9S, and 9T are circuit diagrams of a differentially-acquired wide-band cardiac phase gradient signal acquisition system in accordance with an illustrative embodiment.

FIG. 13 is an example operation of a BSA instrument in accordance with an illustrative embodiment.

DETAILED DESCRIPTION

Figure 1:
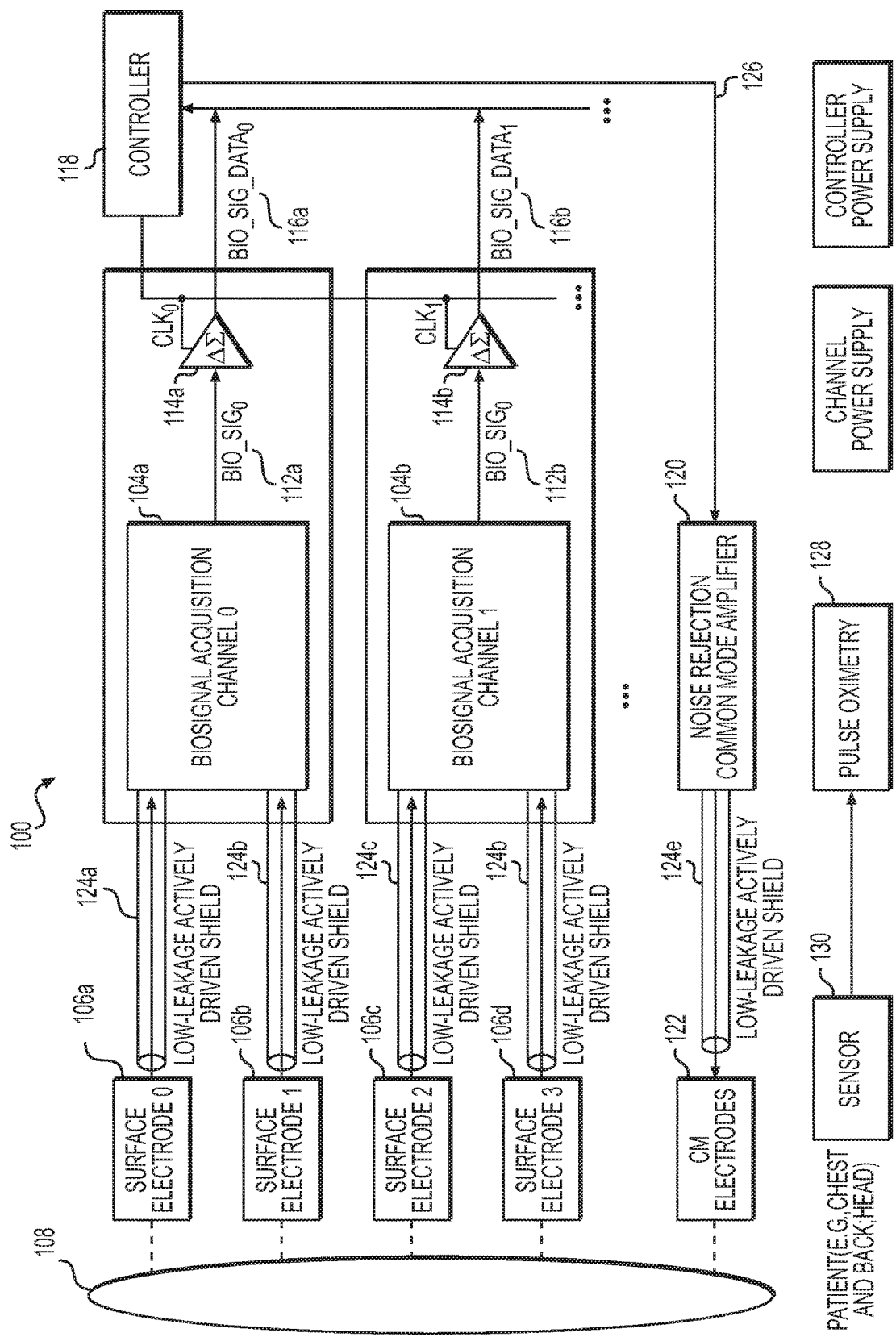
FIG. 1 is a diagram of an example apparatus configured to differentially acquire wide-band cardiac phase gradient signals in accordance with an embodiment.

The components in the drawings are not necessarily to scale relative to each other and like reference numerals designate corresponding parts throughout the several views.

FIG. 1 is a diagram of an example apparatus 100 configured to differentially acquire wide-band cardiac phase gradient signals in accordance with an embodiment. As shown in FIG. 1, apparatus 100 includes a number of biosignal acquisition channels 104 (shown as "biosignal acquisition channel 0" 104a and "biosignal acquisition channel 1" 104b) that is each operatively coupled to a corresponding pair of surface electrodes 106 (shown as surface electrodes 106a, 106b, 106c, 106d, and etc.) to differentially acquire wide-band cardiac phase gradient signals from a patient's chest area and/or back area 108. In some embodiments, apparatus 100 includes three biosignal acquisition channels 104 for XYZ lead measurements.

In some embodiments, the biosignal acquisition channels 104 are configured to differentially acquire wide-band phase gradient signals (e.g., wide-band cerebral phase gradient signal) at other locations, for example, at a patient's head. In other embodiments, wide-band phase gradient signals are differentially acquired from other areas of the body, e.g., in proximity to a target organ.

Bipolar sensing provides true differential XYZ lead measurements of wide-band cardiac phase gradient signals in which vectorcardiograms (VCG) derived therefrom are stable on any choice of reference positions (i.e., the measurements are not sensitive to lead positions). Leads of apparatus 100 have polarity and are placed at specific locations on the body surface. A reference lead (shown as "CM Electrode" 122) is used to reduce noise.

Bipolar sensing facilitate differential measurements that reduce, or eliminate, common mode noise based on internal symmetry of the analog to digital converters (ADCs) and only amplifies potential differences between two points with very high common mode rejection. Bipolar sensing facilitate differential measurements that also provide high static gain accuracy.

Referring still to FIG. 1, each biosignal acquisition channel 104 includes one or more amplifier circuits 110 (e.g., instrumentation class amplifiers) (not shown—see FIG. 4A or 4B) that amplifies, via bipolar inputs, differential biopotential signals received at a given amplifier circuit to generate a differential amplified biopotential signal 112 (shown as "BIO_SIG$_0$" 112a, "BIO_SIG$_1$" 112b, and etc.) corresponding to wide-band cardiac phase gradient signal having little or no non-linear distortions introduced into the signal path.

Example of such non-linear distortions includes phase distortions that may affect the signal at different frequencies which can distort the wide-band cardiac phase gradient signal in the phase space domain. In addition, non-linear distortions includes variability in the signal paths among the different acquisition channels.

As shown in FIG. 1, the biosignal acquisition channels 104 are coupled to a corresponding analog-to-digital conversion circuit 114 (shown as 114a, 114b, and etc.) that are simultaneously sampled such that a temporal skew among each of the sampled signal is less than about 1 μs, to convert the amplified differential biopotential signals 112a, 112b to time-series data (shown as "BIO_SIG_DATA$_0$" 116a, "BIO_SIG_DATA$_1$" 116b, and etc.) associated with the differentially-acquired wide-band cardiac phase gradient signal and that are received by a controller 118 for subsequent analysis (e.g., in phase space domain). In some embodiments, the biosignal acquisition channels 104 are configured to simultaneously sample the acquired signal with a temporal skew of not more than about 10 femtoseconds.

The controller 118 manages the acquisition and recording of the biosignal from the patient and, in some embodiments, manages the transmission of recorded information (including, e.g., biosignals, instrument identification, and patient identification) to a remote data storage location (e.g., a storage area network). In some embodiments, the controller 118 manages the acquisition and recording of the biosignal from the patient and interfaces with a computing device to transmit recorded information (including, e.g., biosignals, instrument identification, and patient identification) to a remote data storage location. In some embodiments, processing is performed on the stored data set to determine cardiac performance, including but not limited to, predicting Ejection Fraction (in percentage), assessing ischemic burden, and/or detecting coronary artery disease, from the differentially-acquired wide-band cardiac phase gradient signals generated from the acquired biopotential signals. In some embodiments, the controller 118 manages the acquisition and recording of the biosignal from the patient and manages the processing, e.g., locally or remotely, of the biosignal to present results on a graphical user interface operatively connected to the controller.

In some embodiments, the system 100 includes a pulse oximeter circuit 128 that operates with a pulse oximeter (PO2) sensor 130 to collect oxygen saturation readings. The collected oxygen saturation readings may be used to augment analyses of the differentially-acquired wide-band cardiac phase gradient signal data. In some embodiments, data associated with oxygen saturation readings are collected concurrently with the acquisition of the wide-band cardiac phase gradient signal data. In other embodiments, data associated with oxygen saturation readings are independently collected. Other sensors or features may also be included.

Referring still to the embodiment of FIG. 1, each analog-to-digital conversion circuit 114a or 114b includes a high-speed sigma-delta converter that is configured to sample simultaneously to have a temporal skew of less than about 1 us (e.g., not more than about 10 fs (femtosecond)) with the other biosignal acquisition channels. The output of the analog-to-digital conversion circuit 114 is preferably a serial data stream (serial digital stream) that is provided to the controller 118. The controller 118, in some embodiments, is configured to aggregate the acquired data 116a, 116b (associated with a differentially-acquired wide-band cardiac phase gradient signal) over a pre-defined period and transmit the collected data to a repository (e.g., a storage area network). In some embodiments, the acquired data 116a, 116b are transmitted as time series data in a file. In some embodiments, the transmission is only performed in between acquisition events. In some embodiments, the file includes one or more, e.g., time series data, instrument identification data, instrument performance data, and/or patient identification data.

In other embodiments, the controller 118 is configured to store the acquired data 116a, 116b, which is then processed locally. In some embodiments, the acquired data is processed by the acquisition system and is then transmitted as collected data (e.g., as a time-series data) to the repository. Each differentially-acquired wide-band cardiac phase gradient signal data sets may have a duration period between about 100 seconds and about 200 seconds.

The differentially-acquired wide-band cardiac phase gradient signal data comprises a wide range of frequencies, in some embodiments, having a sampling greater than 1 KHz (Kilo-Hertz). In some embodiments, the differentially-acquired wide-band cardiac phase gradient signal data comprises a sampling frequency greater than about 5 KHz. In some embodiments, the wide-band cardiac phase gradient signal data comprises a sampling frequency greater than about 10 KHz. In some embodiments, the differentially-acquired wide-band cardiac phase gradient signal data comprises a sampling frequency greater than about 40 KHz. In some embodiments, the wide-band cardiac phase gradient signal data comprises a sampling frequency greater than about 80 KHz. In some embodiments, the differentially-acquired wide-band cardiac phase gradient signal data comprises a sampling frequency greater than about 500 KHz. In various embodiments, the differentially-acquired wide-band cardiac phase gradient signal data has little or no non-linear distortion within its range of sampled frequencies.

In addition, the differentially-acquired wide-band cardiac phase gradient signal data has a range of at least about 5 mV (millivolt) at a resolution of less than about 2 µV (microvolt) per bit. In some embodiments, the differentially-acquired wide-band cardiac phase gradient signal data has a resolution of about, or less than, ½ µV per bit. Other such ranges and resolutions may be used.

Because ½ µV is below the thermal noise associated with most conventional circuitries, the system 100 includes several features to reduce interference from its own circuitries as well as from external energy sources such as from radiofrequency transmissions. It is observed that noise level of a differentially-acquired wide-band cardiac phase gradient signal, when implemented with such techniques, are generally less than about 10 µV.

Figures 2, 3:
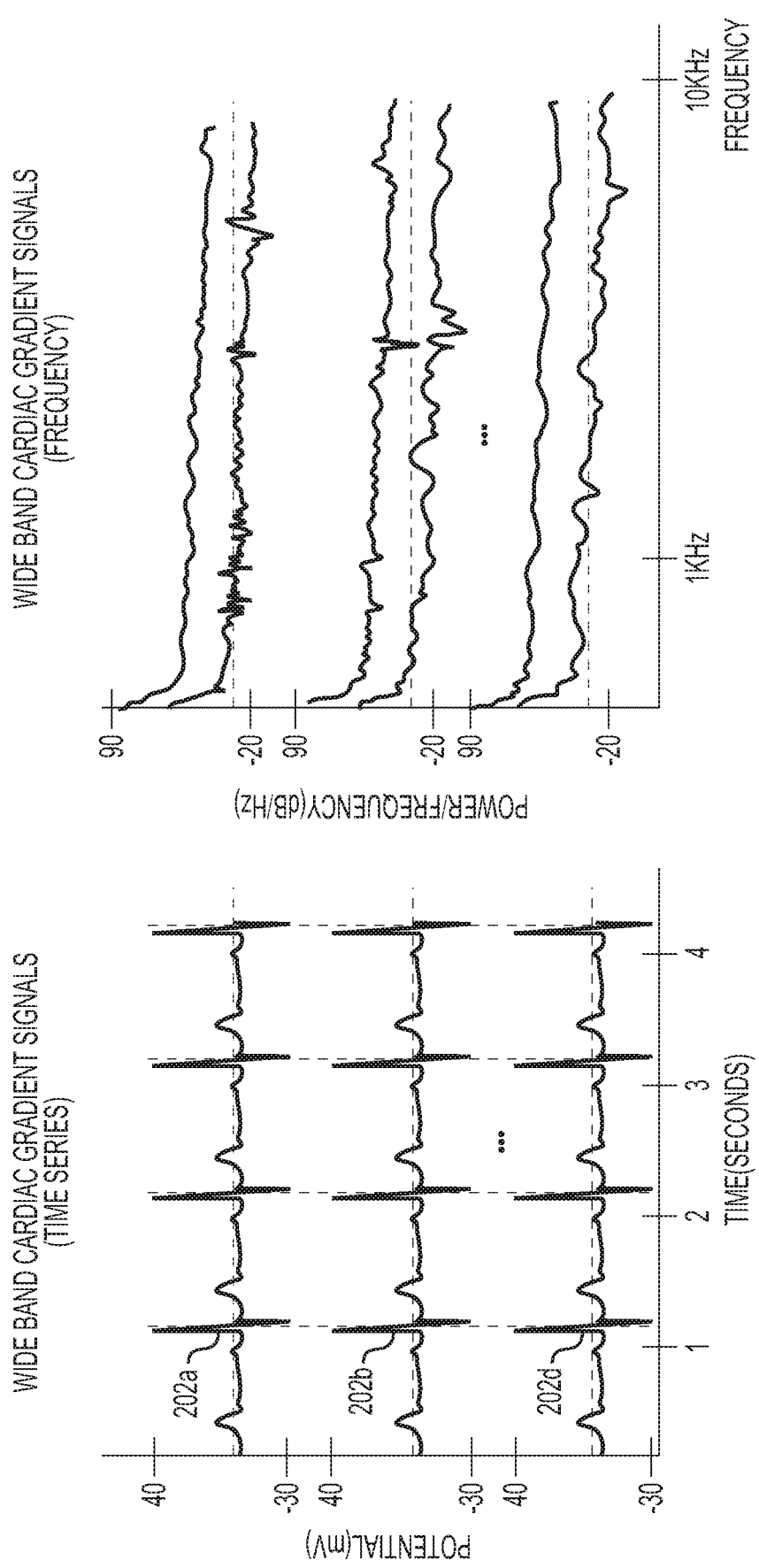
FIG. 2 is a diagram of a time series representation of a wide band cardiac gradient signal (unipolar) in accordance with an illustrative embodiment.
FIG. 3 is a diagram of the example differentially-acquired wide-band cardiac gradient signal data of FIG. 2 shown in the frequency domain, in accordance with an embodiment.

FIG. 2 is a diagram of an example unipolar wide-band cardiac phase gradient signal data (shown as 202a, 202b, 202c, and etc.) shown as a time series data, in accordance with an embodiment. The differentially-acquired wide-band cardiac phase gradient signal data shows a difference between two of these signals (e.g., 202a and 202b; 202c and 202d, and etc.). In some embodiments, the patient is actively driven to a common mode potential and the acquired biopotential signal includes that common mode potential. In such embodiments, the differentially-acquired wide-band cardiac phase gradient signal data is the remaining signal with the common-mode reference removed, e.g., via differential acquisition scheme or via computation. In some embodiments, the differentially-acquired wide-band cardiac phase gradient signal data has been amplified and normalized with the common-mode reference removed via hardware circuitry.

FIG. 3 is a diagram of the example differentially-acquired wide-band cardiac phase gradient signal data of FIG. 2 shown in the frequency domain, in accordance with an embodiment.

It is discovered that wide-band biopotential signals and differential signals thereof, having energy and frequency components beyond those of conventional electrocardiography (ECG) and traditionally perceived to be random noise, includes measurable data of the heart physiology that can be discriminated by genetic algorithms (and other machine learning algorithms) to assess regional flow characteristics of the heart, including an estimated value for stenosis an identification of ischemia, a fractional flow reserve (FFR) of specific arteries and branches thereof. Noise removal (e.g., by applying cleaning techniques to the data resulting in the same amount of data as prior to noise removal) is a fundamental step in signal processing. However, the exemplified method and system processes the entire obtained biopotential signals without any noise removal operations in the wide-band region of the signal. What has heretofore been perceived and/or classified as unwanted noise in the wide-band data is, in many cases, the signal of interest. Examples of noise removal that is not performed include, but not limited to, analog-based low-pass filters, band-pass filters, high-pass filters and well as digital-based filters such as FIR filters, Butterworth filters, Chebyshev filters, median filters, among others.

In addition to removing information of interest from the acquired wide-band signals, certain circuit elements can introduce non-linear distortions that can affect analyses in phase space of the differentially-acquired wide-band phase gradient signals and are not included, or minimized, in the signal path of the exemplified system. For example, certain analog pass filters (e.g., analog-based low-pass filters, band-pass filters, high-pass filters and well as digital-based filters such as FIR filters, Butterworth filters, Chebyshev filters, median filters, among others, as discussed above) may introduce phase distortions which may result in non-linear group delays among the multiple acquisition channels or introduce frequency-dependent distortions in individual acquisition channels. In addition, certain circuit elements such as field-effect transistors (e.g., MOSFET) may introduce unnecessary capacitance and gate-field effect noise to the signal path. In addition, certain semiconductor and insulating materials with avalanche breakdown effects (e.g., in Zener diodes) may introduce avalanche noise to the signal path.

In some embodiments, the signal may be processed via phase linear operations to allow for analyses of specific aspects of the high-frequency wide-band data. In some embodiments, the signal may be processed via operations or circuitries that affect frequencies completely outside the band of interest. In some embodiments, these frequencies that are filtered are in the radiofrequency range or above.

As shown in FIG. 3, the wide-band cardiac gradient signal has a frequency component greater than about 1 kHz, which is significantly higher than convention electrocardiogram measurements. In some embodiments, the differential wide-band cardiac gradient signal has a frequency component up to about 2 kHz (e.g., about 0 Hz to about 2 kHz). In some embodiments, the different wide-band cardiac gradient signal has a frequency component up to about 4 kHz (e.g., about 0 Hz to about 4 kHz). In some embodiments, the differential wide-band cardiac gradient signal has a frequency component up to about 5 kHz (e.g., about 0 Hz to about 5 kHz). In some embodiments, the differential wide-band cardiac gradient signal has a frequency component up to 6 kHz (e.g., about 0 Hz to about 6 kHz). In some embodiments, the differential wide-band cardiac gradient signal has a frequency component up to about 7 kHz (e.g., about 0 Hz to about 7 kHz). In some embodiments, the differential wide-band cardiac gradient signal has a frequency component up to about 8 kHz (e.g., about 0 Hz to about 8 kHz). In some embodiments, the differential wide-band cardiac gradient signal has a frequency component up to 9 kHz (e.g., about 0 Hz to about 9 kHz). In some embodiments, the differential wide-band cardiac gradient signal has a frequency component up to 10 kHz (e.g., about 0 Hz to about 10 kHz). In some embodiments, the differential wide-band cardiac gradient signal has a frequency component up to 50 kHz (e.g., about 0 Hz to about 50 kHz).

Figure 4A:
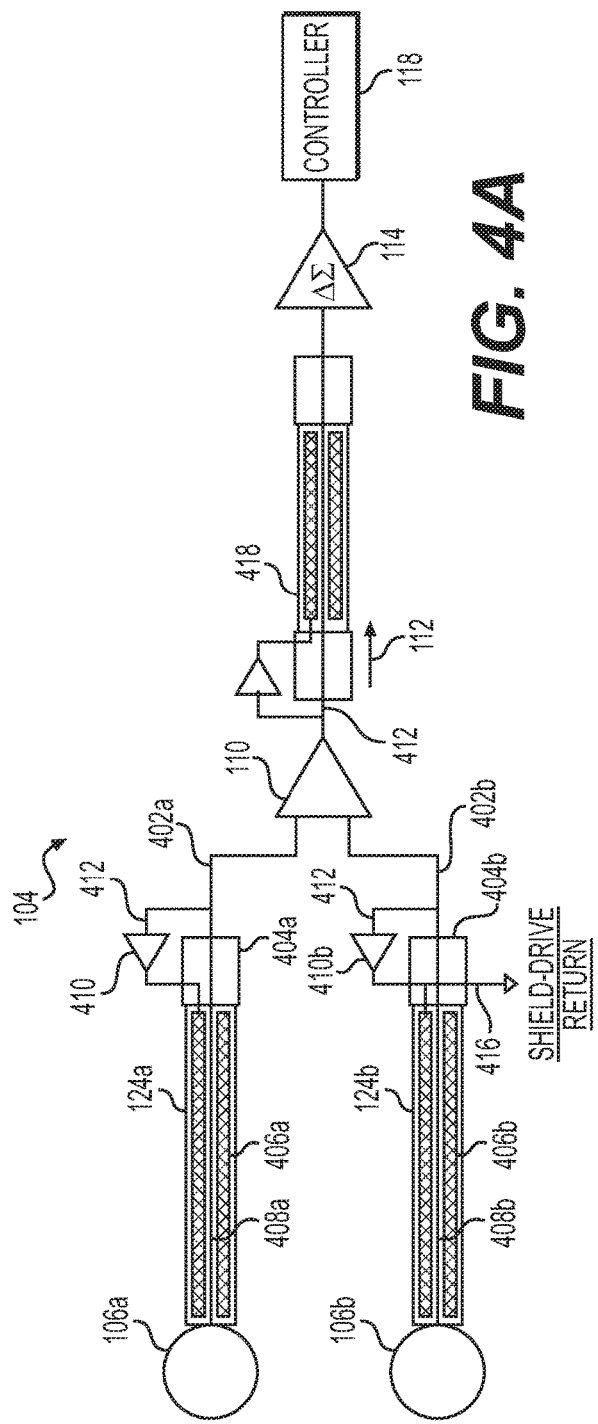
FIG. 4A is a detailed diagram of a biosignal acquisition channel of FIG. 1 with bipolar sensing in accordance with an illustrative embodiment.

FIG. 4A is a diagram of a biosignal acquisition channel 104 with bipolar sensing in accordance with an illustrative embodiment. The biosignal acquisition channel 104 includes an operational amplifier 110 (e.g., an instrumentation class amplifier) having a first differential input 402a and a second differential input 402b that each directly couples to a terminal (shown as 404a, 404b) to operatively couple to the surface electrodes 106a, 106b. The biosignal acquisition channel 104 is configured such that little, or no, non-linear distortions (e.g., such as those discussed herein) are introduced into the signal path. To this end, active and passive filters are preferably not placed in the signal path, or are minimized, to reduce distortions that they may be introduced during operation. In some embodiments, a single anti-aliasing filter is included in the signal path (that also servers a protection to the input of the channel). The operational amplifier 110 preferably provides a gain greater than about 15 dB (decibel) to generate the differentially-acquired wide-band phase gradient signal. In some embodiments, the operational amplifier 110 provides a gain greater than about 20 dB. The output 412 of the operational amplifier 110, in some embodiments, is coupled to the analog-to-digital conversion circuit 114 (e.g., sigma-delta ADC). In some embodiments, the operational amplifier 110 and the analog-to-digital conversion circuit 114 are part of a single integrated circuit. In addition, though shown as two terminals, terminals 404a, 404b may be part of a common terminal housing.

In some embodiments, and as shown in FIG. 4A, each biosignal acquisition channel 104 electrically couples to a respective set of paired surface electrodes 106a, 106b over a pair of cables 124a, 124b (e.g., a co-axial cable)) that employs an active noise reduction system. In some embodiments, the active noise reduction system is used to actively shield signal-carry conductors used to carry signal across multiple circuit boards prior to the acquired signal being digitized.

In FIG. 4A, the biosignal acquisition channel 104 include an active noise reduction system that actively shields the signal-carrying conductors 408a, 408b in cable 124a, 124b arranged between the surface electrode 106a, 106b and the operational amplifier 110. The cables 124a, 124b include a set of first conductors 408a, 408b (e.g., pair of twisted wires) and a set of second conductive layers 406a, 406b (i.e., outer shield) that surrounds the respective first conductors 408a, 408b. The active noise reduction system includes a shield-equalizing circuit (also referred to as a shield-drive circuit or cable-drive circuit) comprising operational amplifiers 410a, 410b that injects the signal carried in the conductors 408a, 408b to the shield 406a, 406b of the cables 124a, 124b such that the injected signal approximately matches (e.g., within at least about 90%) the signal carried in the cable. Put another way, the active noise reduction system drives the shield 406a, 406b to about the same electric potential as the conductor 408a, 408b which reduces the electrical leakage between the conductors 408a, 408b and the shield 406a, 406b. In another aspect, the outer shields (e.g., 406a, 406b) of the cables (e.g., 124a, 124b) are electrically coupled to a shield-drive voltage plane 416 (also referred to as a cable-drive voltage plane) to provide a return pass for noisy current induced on the outer shield (e.g., 406a, 406b).

In some embodiments, the operational amplifier 410 is configured as a unity gain amplifier. In other embodiments, non-unity gain is used. The inputs 414a, 414b of the operational amplifiers 410a, 410b are coupled to the input of the gain amplifier 110, which is also coupled to the terminals 404a, 404b. The outputs of the operational amplifiers 410a, 410b are coupled to the second conductive layers 406a, 406b of the cables 124a, 124b.

Figure 4B:
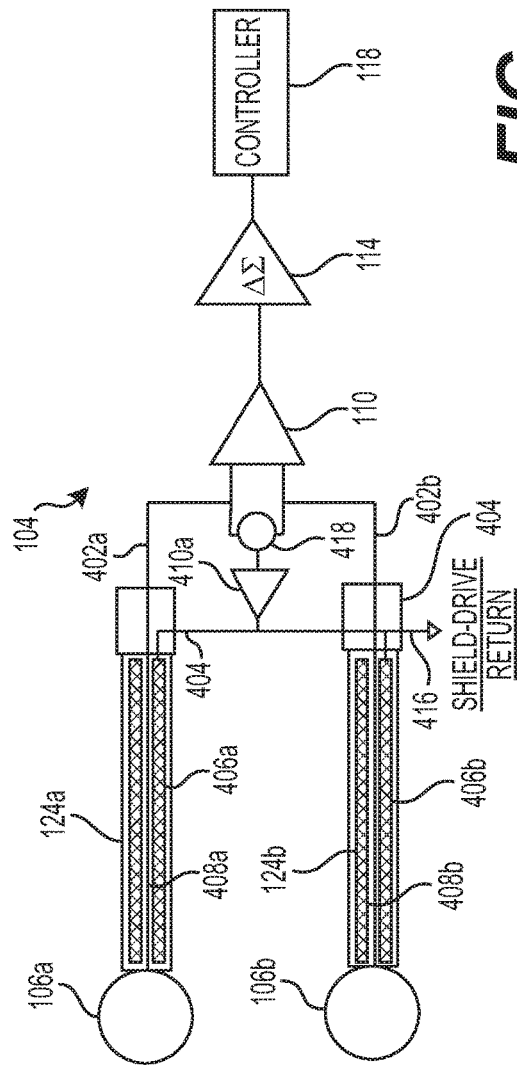
FIG. 4B is a detailed diagram of a biosignal acquisition channel of FIG. 1 with bipolar sensing in accordance with another illustrative embodiment.

FIG. 4B is a diagram of a biosignal acquisition channel 104 with bipolar sensing in accordance with another illustrative embodiment. In FIG. 4B, an active noise reduction system is used in which an average potential from all, or most, of the signal-carrying conductors (e.g., 408a, 408b) is used to drive the outer shield 406a, 406b of the cables (e.g., 124a, 124b) for each of the biosignal acquisition channels. As shown in FIG. 4B, an operational amplifiers 410a is coupled to an averaging circuit 418 that is coupled to each of the signal-carrying conductors (e.g., 408a, 408b). The signal-carrying conductors (e.g., 408a, 408b) are coupled to the gain amplifier 110 that coupled to the analog-to-digital conversion circuit 114. In FIG. 4B, the gain amplifier 110 and the analog-to-digital conversion circuit 114 are arranged on the same printed circuit board. In some embodiments, the gain amplifier 110 and the analog-to-digital conversion circuit 114 are combined in a single integrated circuit. Other components may be arranged with the gain amplifier 110 to provide a desired gain output for the amplifier.

In another embodiment, the operational amplifiers 410a is coupled to output of an amplifier output of a microcontroller that generates an analog output signal by averaging the inputs of the acquired differential wide-band cardiac gradient signal.

In some embodiments, the outer shields (e.g., 406a, 406b) are electrically coupled to a shield-drive voltage plane 416 to provide a return pass for noisy current induced on the outer shield (e.g., 406a, 406b).

In some embodiments, the active noise reduction system uses the potential of a single signal-carrying conductor (e.g., 408a or 408b) to drive the outer shields for all the cables (408a, 408b, etc.) of all the biosignal acquisition channels.

FIG. 5 is a diagram illustrating operations of the shield-equalizing circuit in accordance with an illustrative embodiment. As shown in FIG. 5, a shield conductor 406 of a cable 124 surrounds a signal conductor 408 and is driven by an operational amplifier (e.g., 410a) to a potential that matches, or nearly matches, that of the signal conductor 408. For example, where the signal conductor 408 carries a potential of about +1.5V, and the operational amplifier (e.g. 410a) drives the shield conductor 406 also to about +1.5V. Because the potential between the signal conductor 408 and shield conductor 406 matches, or nearly matches, the dielectric electric field between them is minimized. To this end, a perturbation introduced to the signal-conductor 408 by the shield-conductor 406 due to perturbation of the shield-conductor 406 from external interference is dampened.

Example Noise Rejection Subsystem

To improve the signal quality of the differentially-acquired wide-band cardiac phase gradient signal 112, the exemplified system 100 (e.g., as shown in FIG. 1), in some embodiments, includes a noise rejection system 120 that eliminates, or reduces, environmental noise currents flowing in the patient's body that might interfere with the biopotential measurement. The noise rejection system 120 is configured to actively drive the patient's body to a potential that shunts environmental noise currents during normal operation. Environmental noise may be generated from a variety of environmental sources including nearby electronics, transmission devices, and local AC power systems, among others. Any or all of these sources may generate voltages at the measurement electrodes that can render a patient's biopotential un-measurable or reduce the resolution of the measurement.

As shown in FIG. 1, the noise rejection system 120 is operatively coupled to a surface electrode 122 that is in electrical contact (e.g., directly or via a conductive gel or paste) with a surface of the body 108. In some embodiments, the noise rejection system 120 actively applies a varying potential to the body 108, e.g., a potential that varies between two negative potential values.

In some embodiments, the surface electrode (e.g., 106a, 106b, 106c, 106d, 122) may be used in conjunction with gels or other coupling media or devices that can form a half-cell potential in the signal path when measuring the differentially-acquired wide-band cardiac phase gradient signal. For example, silver chloride gel may introduce a 300 mV biased in the signal path. In some embodiments, the noise rejection system 120 actively drives the body 108 to a varying potential that varies between two negative potential values such that the magnitudes of negative potential values are greater than the expected half-cell potential DC bias value associated with the surface electrodes.

Referring still to FIG. 1, noise rejection system 120 is electrically coupled, via a cable 124e, to a common-mode electrode 122 that is placed on the body 108. In some embodiments, an active noise reduction system, e.g., similar to that used in the biosignal acquisition channels, is used to actively shield the signal-carrying conductor in the cable 124e between the common-mode surface electrode 122 and the noise rejection system 120. In other embodiments, a passive shield is used in which the shield-conductor of the cable 124e is coupled to the ground plane of the system 100.

The noise rejection system 120, in some embodiments, includes a waveform generator and an operational amplifier. In some embodiments, the waveform generator is a fixed-frequency oscillator. In other embodiments, the waveform generator is a microcontroller that is electronically programmable to generate an analog output that can vary in frequency and amplitude range, e.g., based on control signals outputted from the controller 118. In FIG. 1, the noise rejection system 120 is shown operatively coupled to the controller 118 via control line 126.

In some embodiments, the noise rejection system 120 actively drives the body 108 to a varying potential that varies between a negative potential value and a positive potential value.

In some embodiments, the noise reduction system 120 actively drives the body 108 to a varying potential that varies between two positive potential values.

In other embodiments, the noise reduction system 120 actively drives the body to a constant potential (e.g., a value between about −1.5 $V_{DC}$ and about +1.5 $V_{DC}$ or a value between about −3.0 $V_{DC}$ and about +3 $V_{DC}$).

Example BSA System

Figure 6:
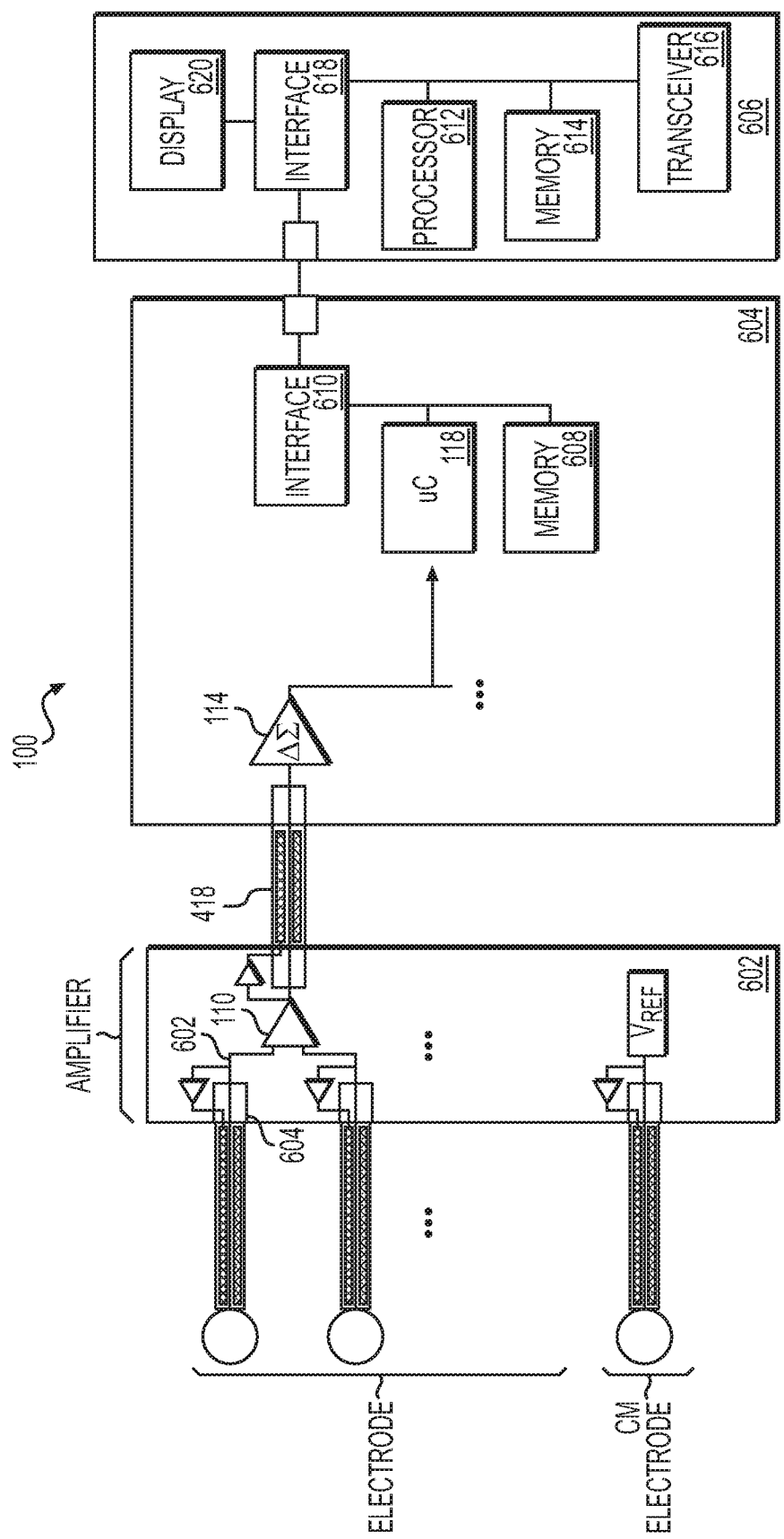
FIG. 6 is a diagram of an example system in accordance with an illustrative embodiment.

FIG. 6 is a diagram of an example system 100 in accordance with an illustrative embodiment. As shown in FIG. 6, the system 100 includes a first stage mixed-signal board 602 that includes the biosignal acquisition channels 104 as described in relation to FIG. 1. The first stage mixed-signal board 602 is operatively coupled to a second stage mixed-signal board 604 over one or more cables 418 that carries the amplified biopotential signals 112. The second stage mixed-signal board 604 includes the analog-to-digital conversion circuit 114 and the controller 118, as described in relation to FIG. 1. The second stage mixed-signal board 604 communicates to a third stage controller board 606 that provides communication and interface functionality for apparatus 100.

As shown in FIG. 6, the second stage mixed-signal board 604 includes memory 608 and interface circuit 610. The memory 608 locally stores the acquired biopotential signal data 116 associated with the differentially-acquired wide-band cardiac phase gradient signal data for a given measurement prior to the data 116 being sent to the third stage controller board 606 to be transmitted to remote storage. The interface circuit 610, in some embodiments, includes communication isolation circuitries such as optical isolators and other isolation circuitries such as, but not limited to, for power and ground. The third stage controller board 606 includes a processor 612, a memory 614, a communication transceiver 616, and an interface circuit 618 that, collectively, is configured to operate with the second stage mix-signal board 604 to offload the differential wide-band cardiac phase gradient signal data acquired thereat to transmit, e.g., via wireless communication to remote storage (e.g., repositories in the cloud). In some embodiments, the third stage controller board 606 is configured to analyze the differentially-acquired wide-band cardiac phase gradient signal data acquired thereat and present outputs of the analyses at a graphical user interface associated therewith. In some embodiments, the third stage controller board 606 is a part of a custom computing device. In other embodiments, the third stage controller board 606 a part of a general computing device.

In some embodiments, the first stage mixed-signal board 602, the second stage mixed-signal board 604, and the third stage controller board 606 are part of a single printed circuit board.

Figure 7:
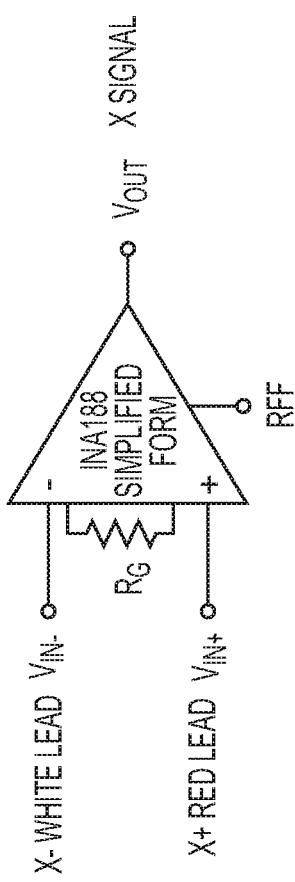
FIG. 7 is a diagram of an example instrumentation amplifier configured for one channel of bipolar sensing operation.

FIG. 7 is a diagram of an example instrumentation amplifier configured for one channel of bipolar sensing operation. The instrumentation amplifier is a zero-drift, instrumentation amplifier (e.g., INA 188 integrated circuit, manufactured by Texas Instruments, Inc. (Dallas, Tex.)).

Figure 8:
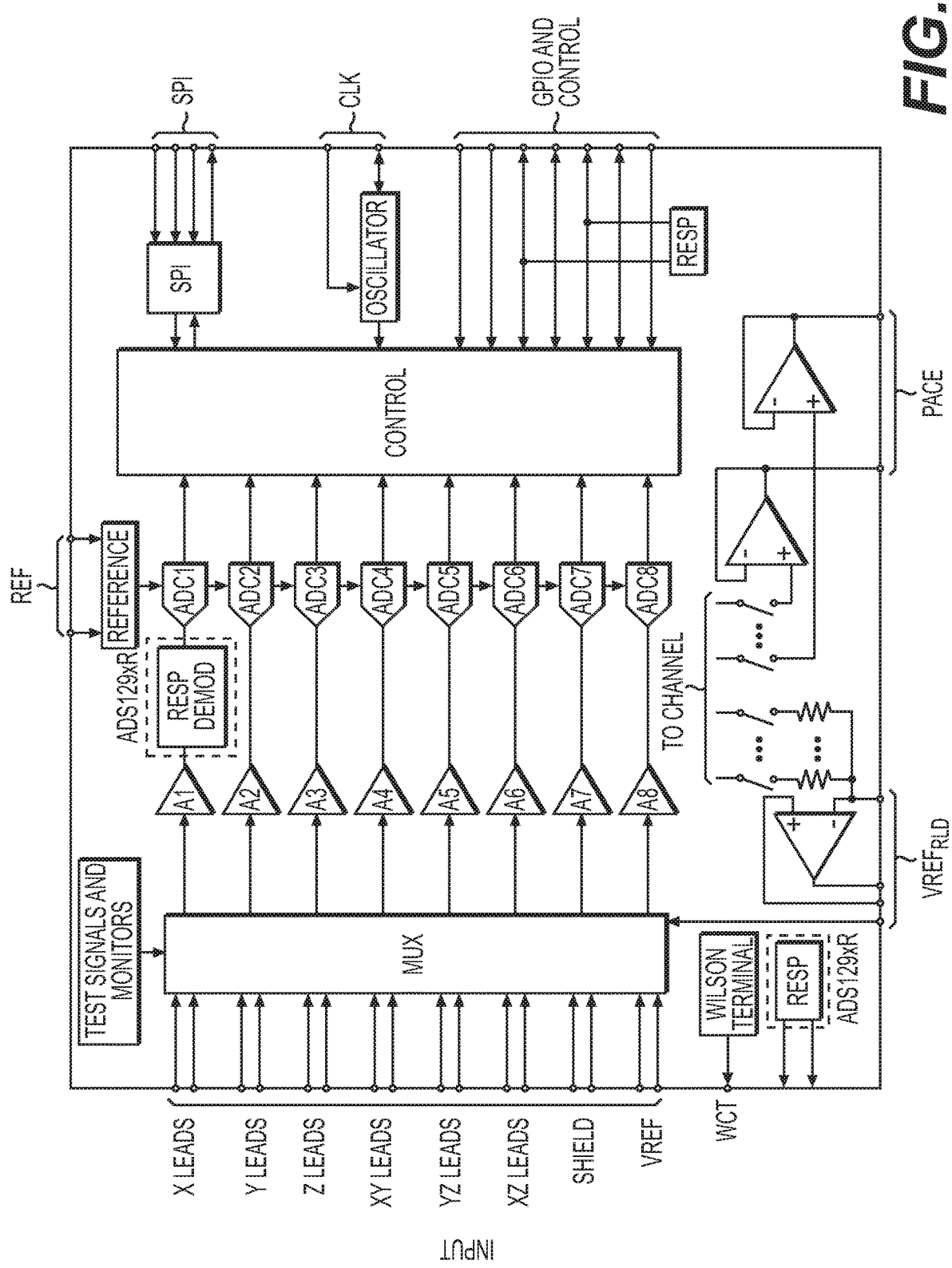
FIG. 8 is a diagram of an example integrated circuit with instrumentation amplifiers configured for multiple channels of bipolar sensing operations.

FIG. 8 is a diagram of an example integrated circuit with instrumentation amplifiers configured for multiple channels of bipolar sensing operations. The integrated circuit is a 6-channel, 24-bit ADC with an integrated ECG front end (e.g., ADS 1296 integrated circuit, manufactured by Texas Instruments, Inc. (Dallas, Tex.)). The integrated circuit has delta-sigma analog-to-digital converters with built-in programmable gain amplifiers (PGAs).

Example BioSignal Acquisition Circuit

FIGS. 9A, 9B, 9C, 9D, 9E, 9F, 9G, 9H, 9I, 9J, 9K, 9L, 9M, 9N, 9O, 9P, 9R, 9S, 9T, and 9V, are circuit diagrams of a prototype wide-band cardiac phase gradient signal acquisition system 900 with bipolar operations in accordance with an illustrative embodiment.

Figure 9A:
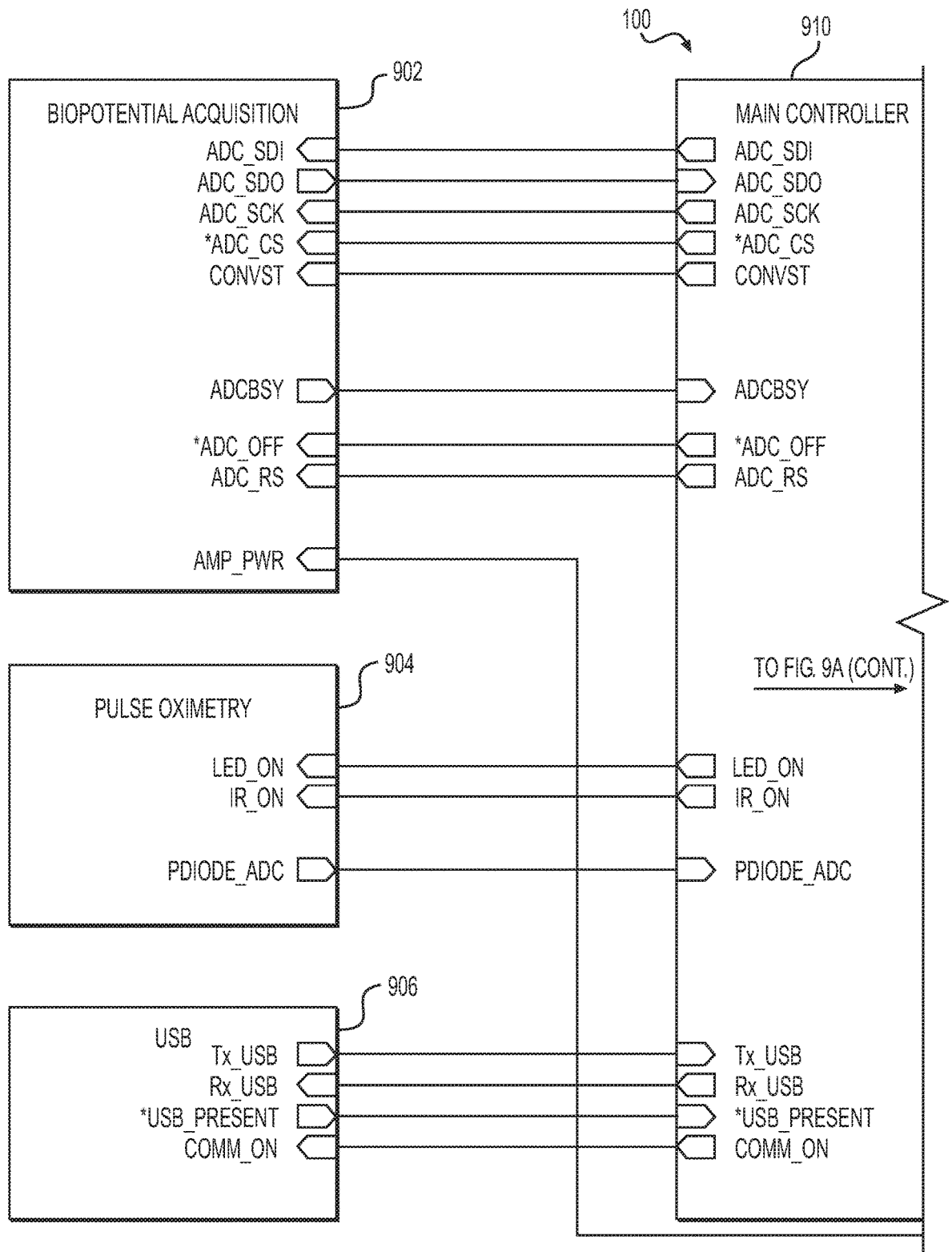
Figure 9A:
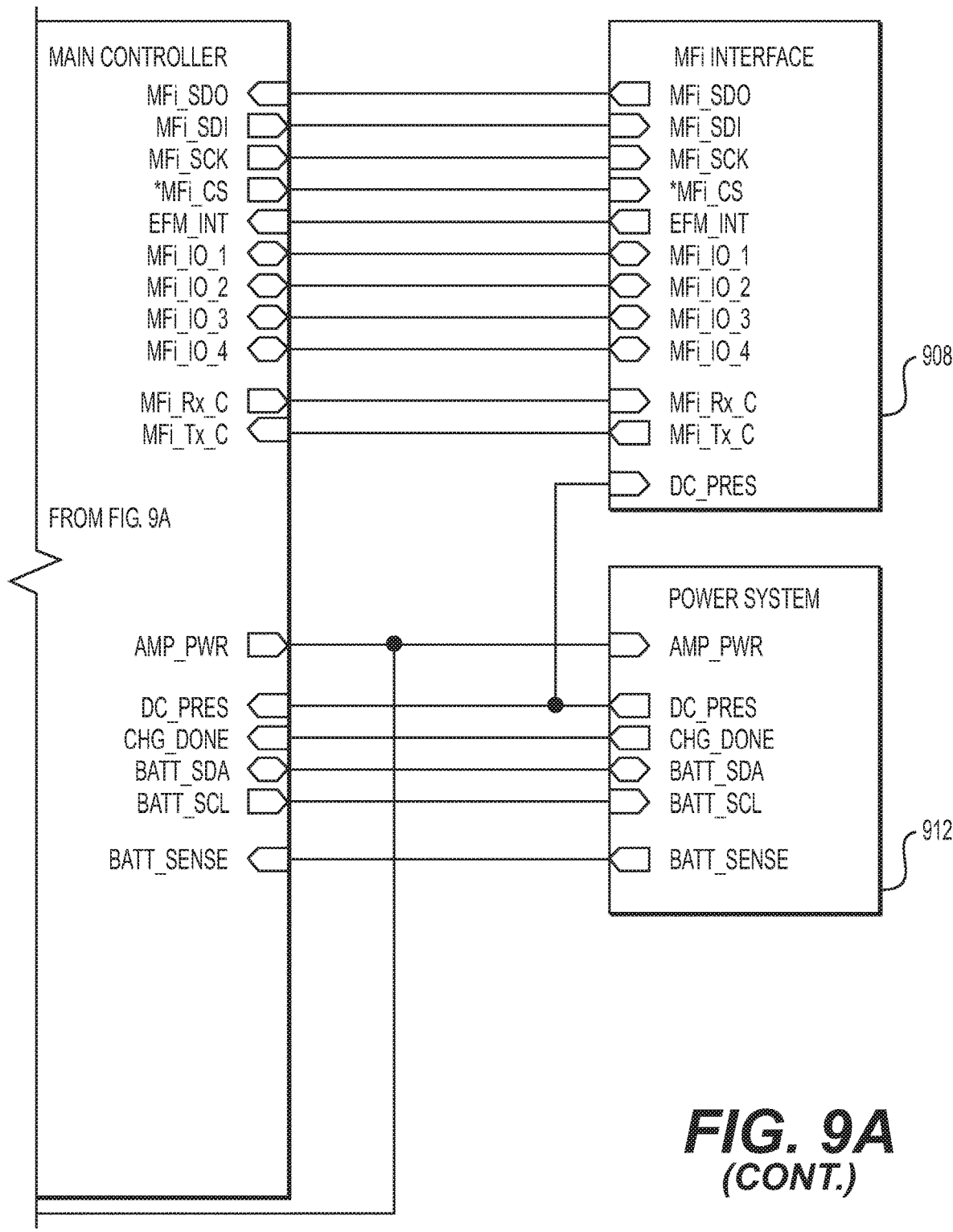

Specifically, FIG. 9A shows a high-level diagram of the system 900. As shown in FIG. 9, the system 900 includes a main controller 910 that couples to a biopotential acquisition circuit 902 that acquires the biopotential signal data associated with differentially-acquired wide-band cardiac phase gradient signals. The main controller 910 may perform the function of controller 118 as described in relation to FIG. 1. The main controller 910 couples to a pulse oximetry circuit 904 that acquires oximetry data. The system 900 further includes a USB interface circuit 906 configured to provide communication to the main controller 910 for testing and development. The system 900 includes an MFi interface circuit 908 that provides connectivity to a computing device (e.g., device 606 as described in relation to FIG. 6). The system 100 further includes a power system 912 to provide power to the various circuits and also to provide reference voltage for the analog-to-digital conversion.

Figure 9B:
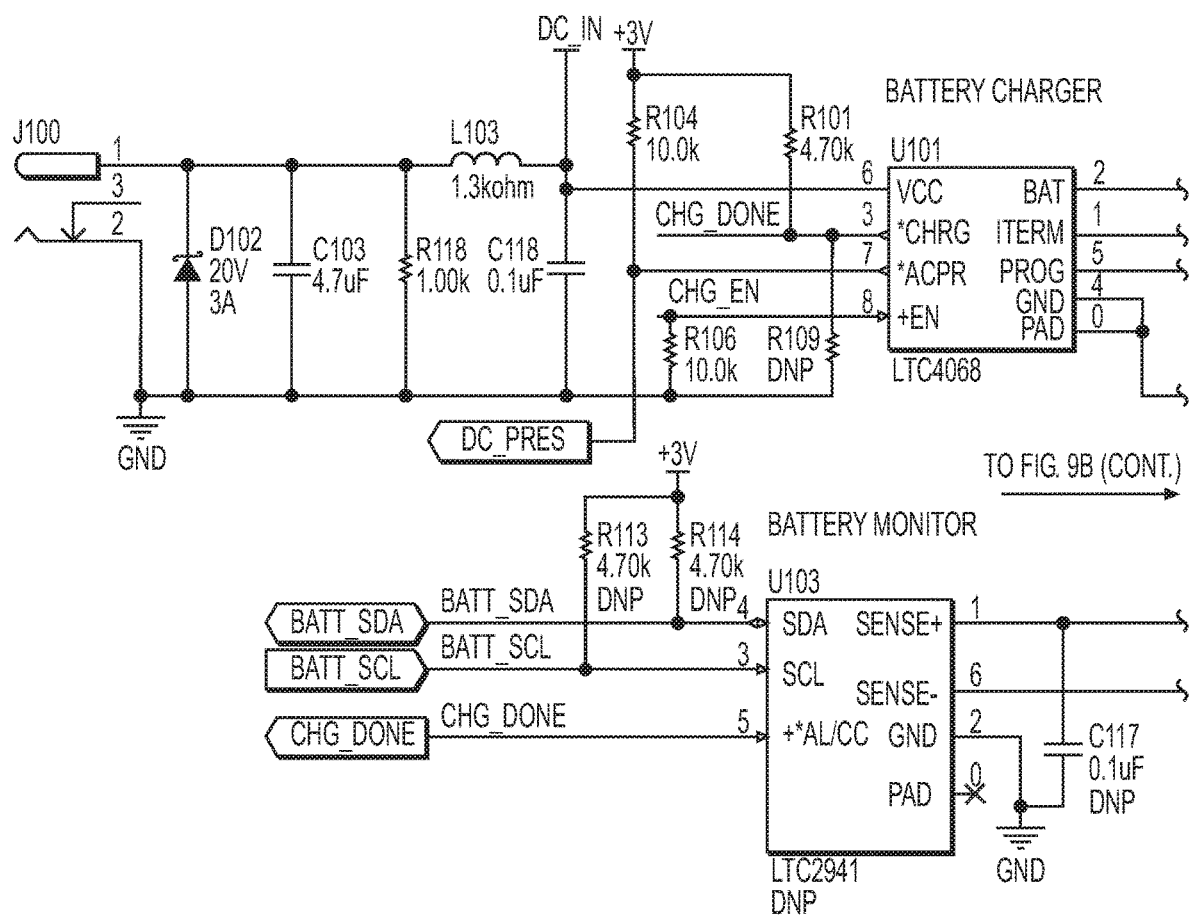
Figure 9B:
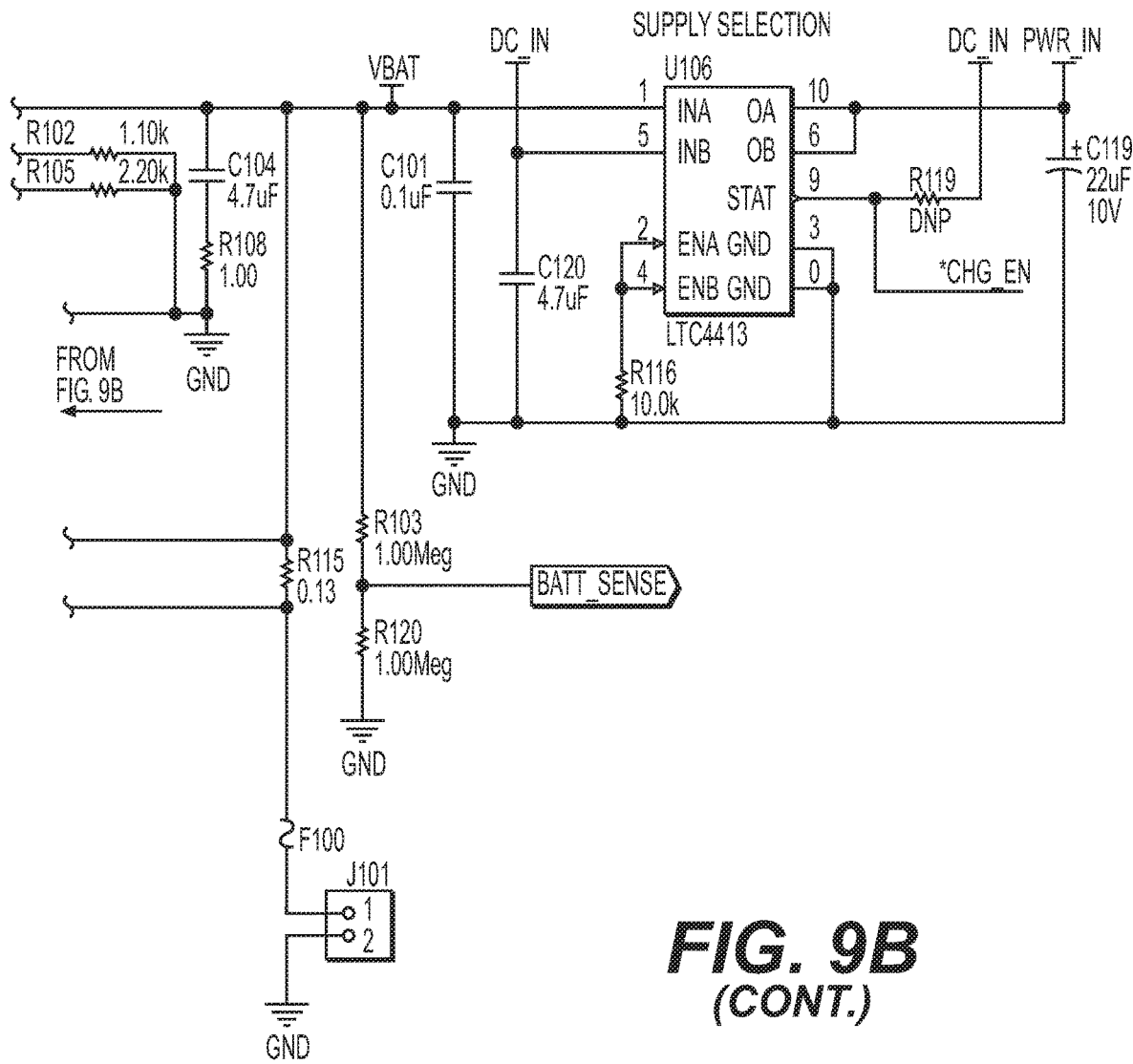
Figure 9C:
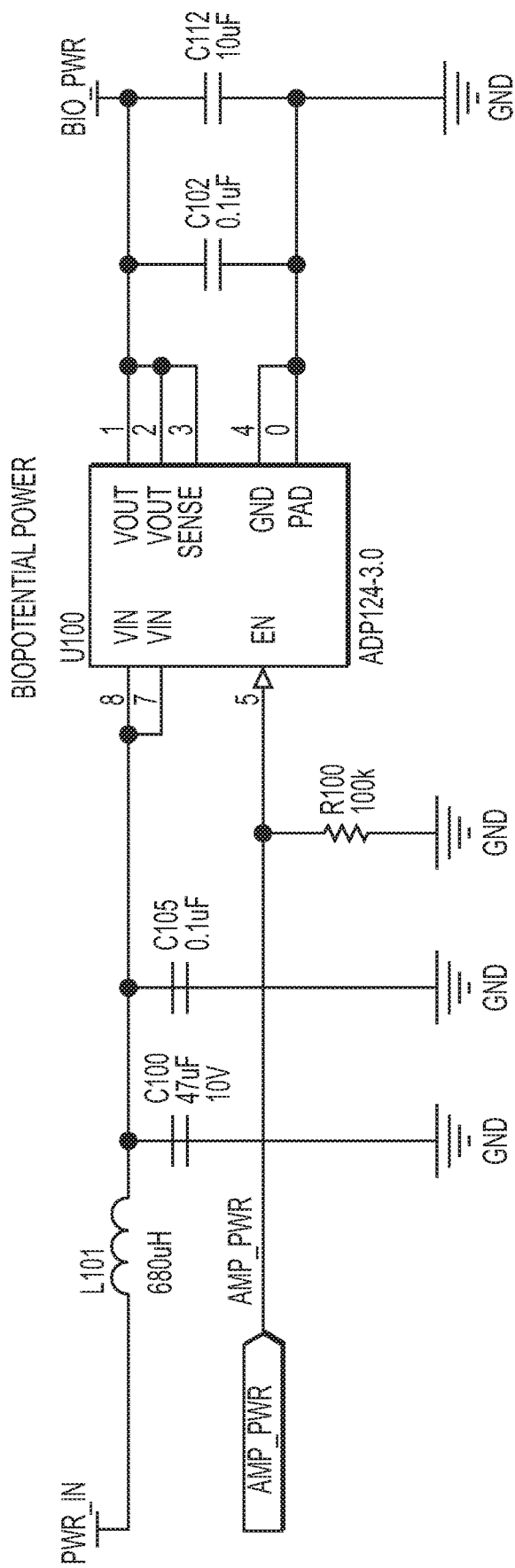
Figure 9D:
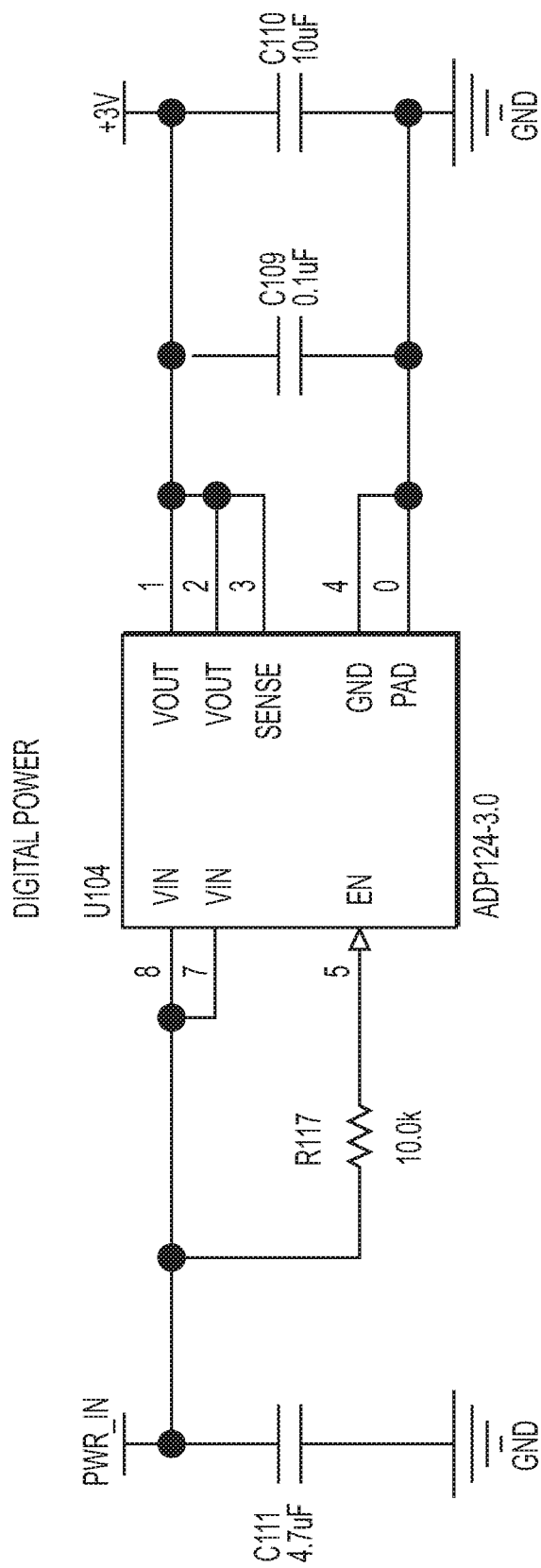

FIGS. 9B, 9C, and 9D show detailed diagrams of power circuits 912. In FIG. 9B, a power circuit 912a to supply power to the system 900 from batteries is shown. The power circuit includes a monitoring and charging circuit. In FIG. 9C, a power circuit 912B for the biosignal acquisition channel is shown. In FIG. 9D, a power circuit 912C for digital circuits is shown.

Figure 9E:
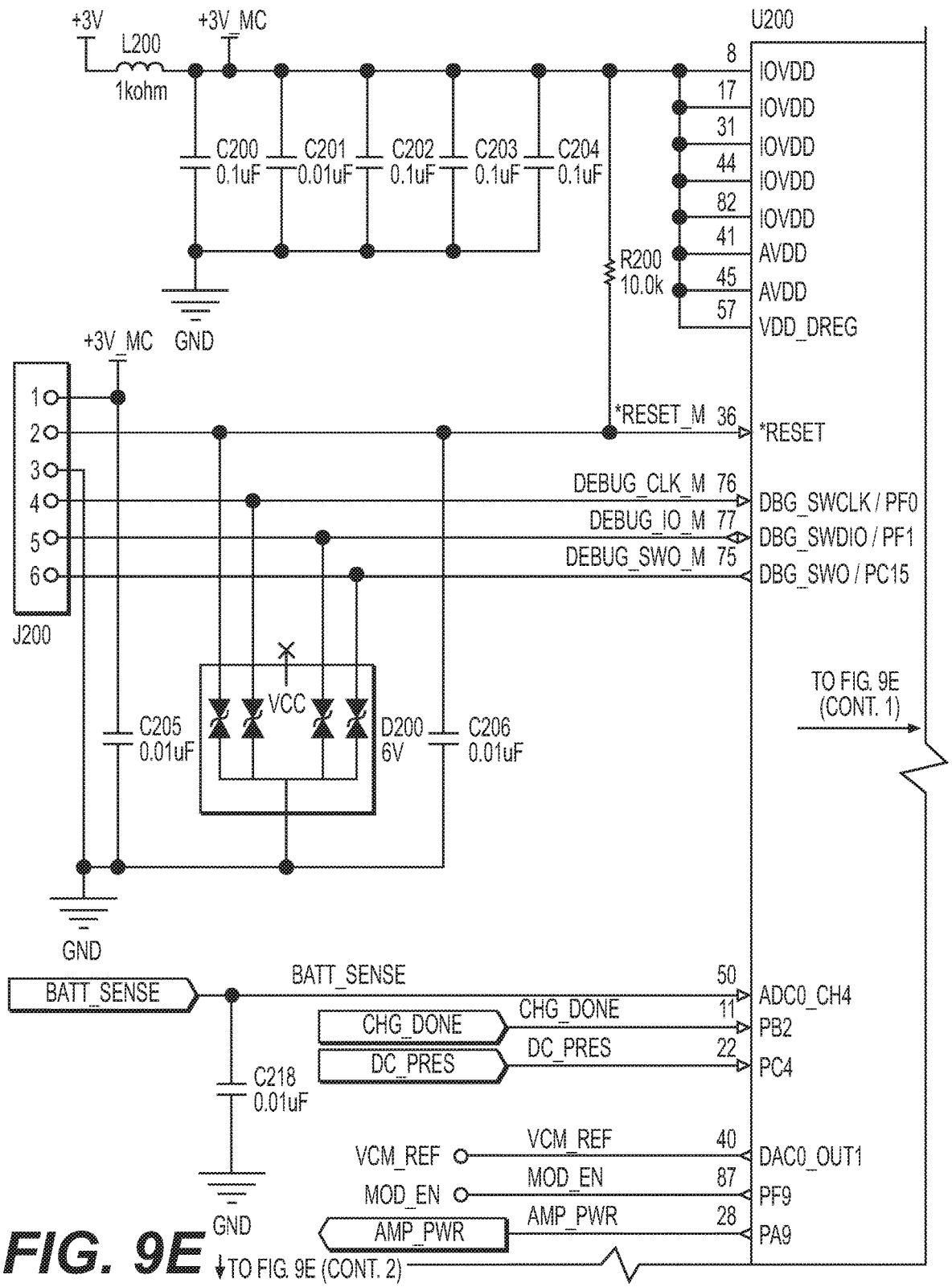
Figure 9E:
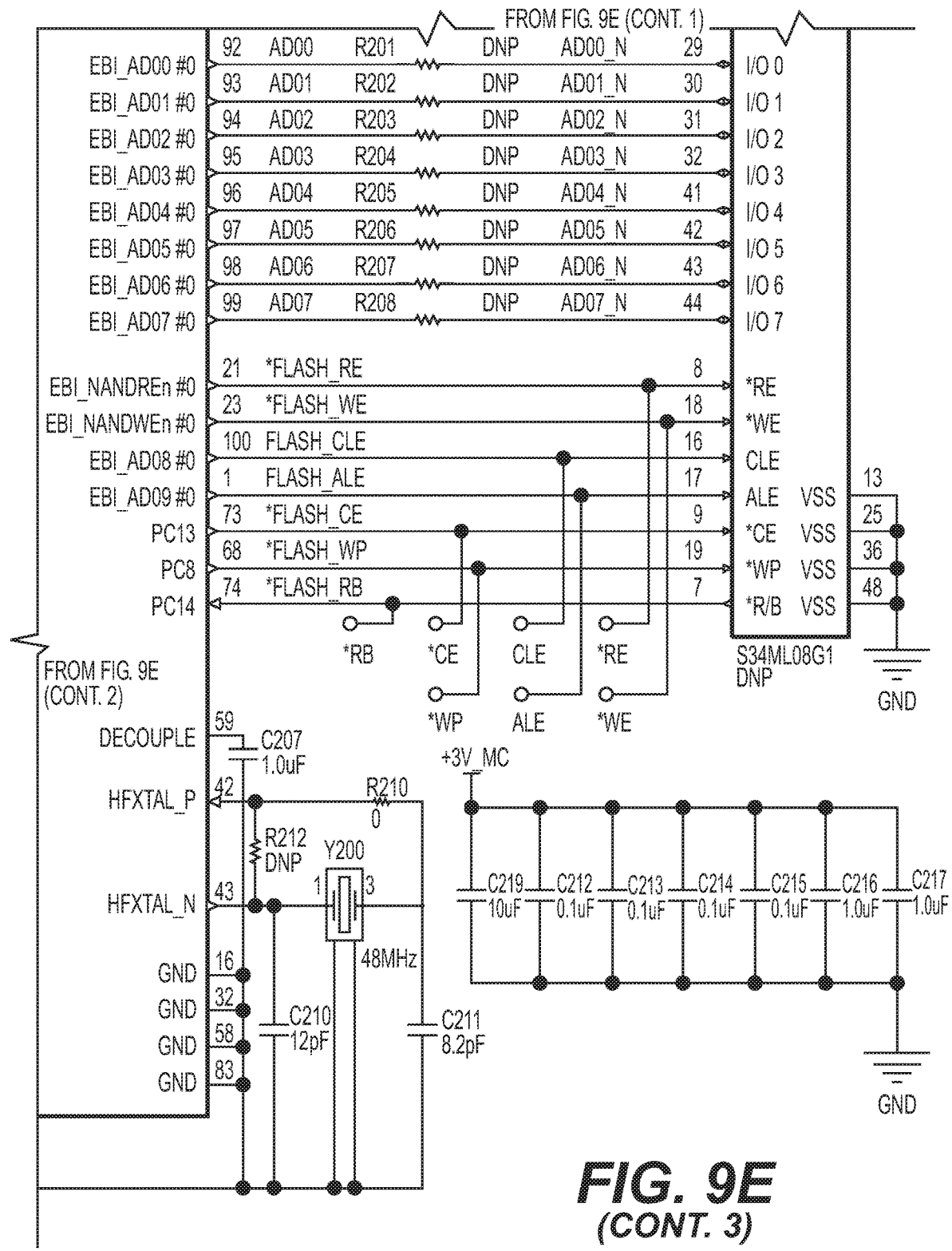

FIG. 9E shows a detailed diagram of a controller circuit for main controller 910 (shown as device "EFM32GG880" 910). The controller circuit includes a memory module 912 (shown as device "S23ML0G1") that couples to the main controller 910. The main controller 910 is an ARM Cortex CPU platform manufactured by Silicon Laboratories (Austin, Tex.), part no. "EFM32GG880". The memory "S23ML0G1" is an 8 GB (gigabyte) NAND Flash memory manufactured by Cypress Semiconductor Corporation (San Jose, Calif.). The main controller 910 operates with the biosignal acquisition channel (e.g., 104) to receive the biopotential signal data and to locally store the data to the NAND Flash memory (e.g., 912) for each acquisition.

Figure 9F:
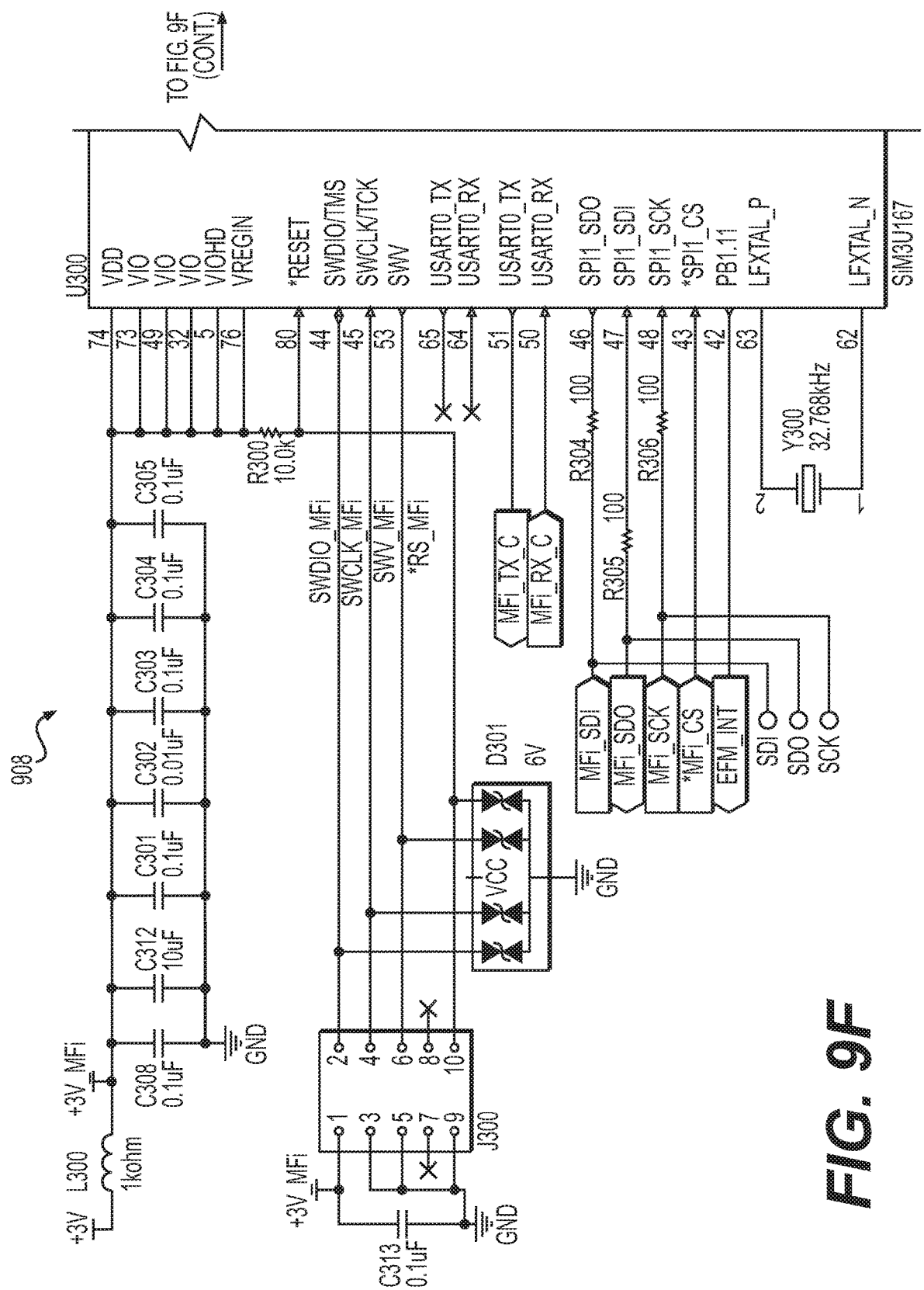
Figure 9F:
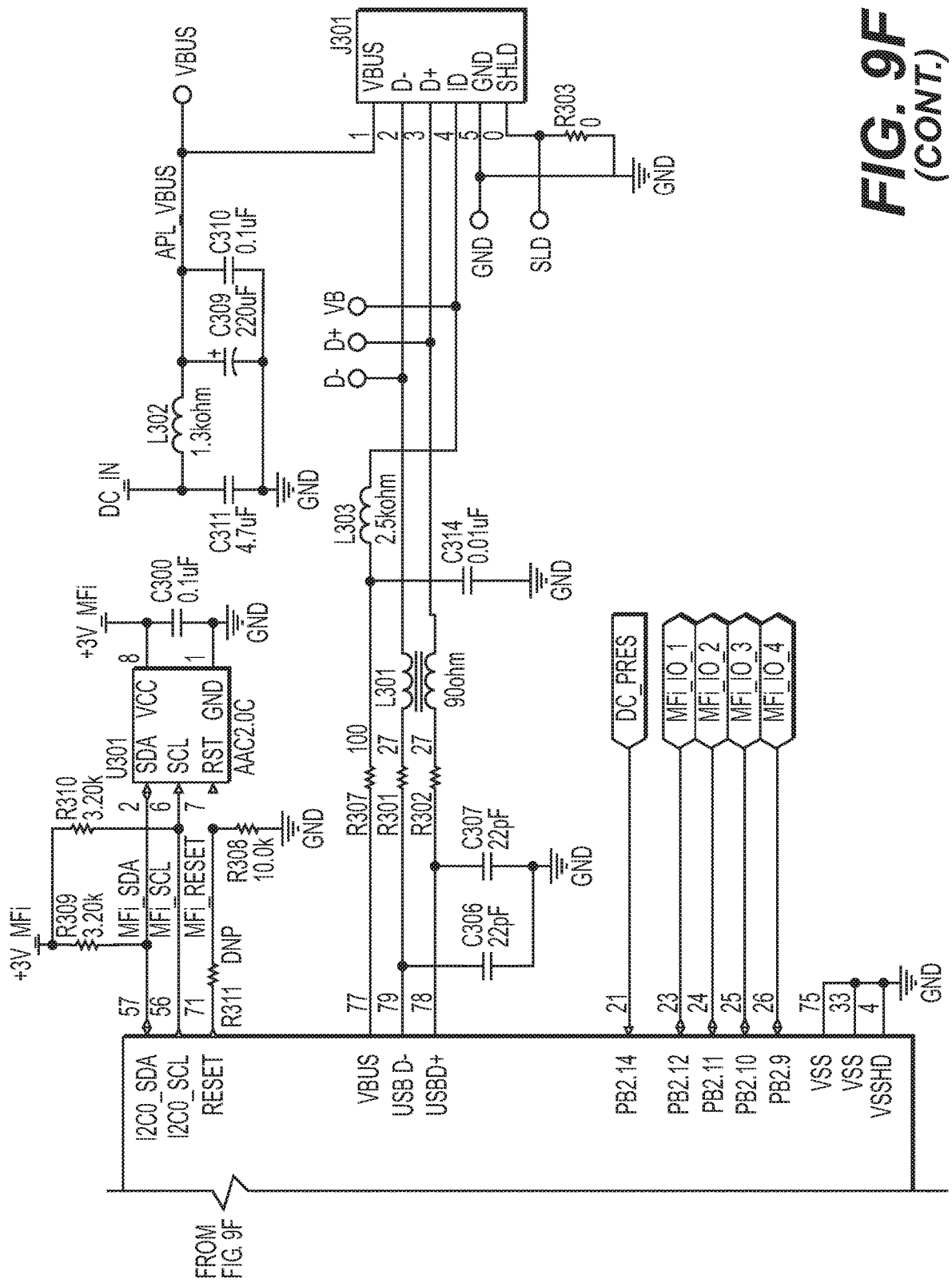

FIG. 9F shows a detailed diagram of the MFi circuit 908. The MFi circuit 908 includes a microcontroller 914 (shown as device "SiM3U167") that provides an interface to an external computing device. The main controller 910 of FIG. 9E may be configured by computer readable instructions stored in memory to retrieve, between acquisition of the differentially-acquired wide-band cardiac phase gradient signal data (e.g., biosignal data and instrument identification data) stored in the NAND Flash memory and transfers the data to an external computing device through the MFi circuit 908. In some embodiments, the MFi circuit 908 may be powered down during the acquisition of wide-band cardiac phase gradient signal data so as to minimize interference during the signal acquisition.

The SiM3U167 is an ARM Cortex-M3 based microcontroller (MCU), manufactured by Silicon Laboratories (Austin, Tex.). The SiM3U167 may be part of a USB MCU family of energy friendly devices configured with low energy operation, fast wake-up times and energy saving modes.

Figure 9G:
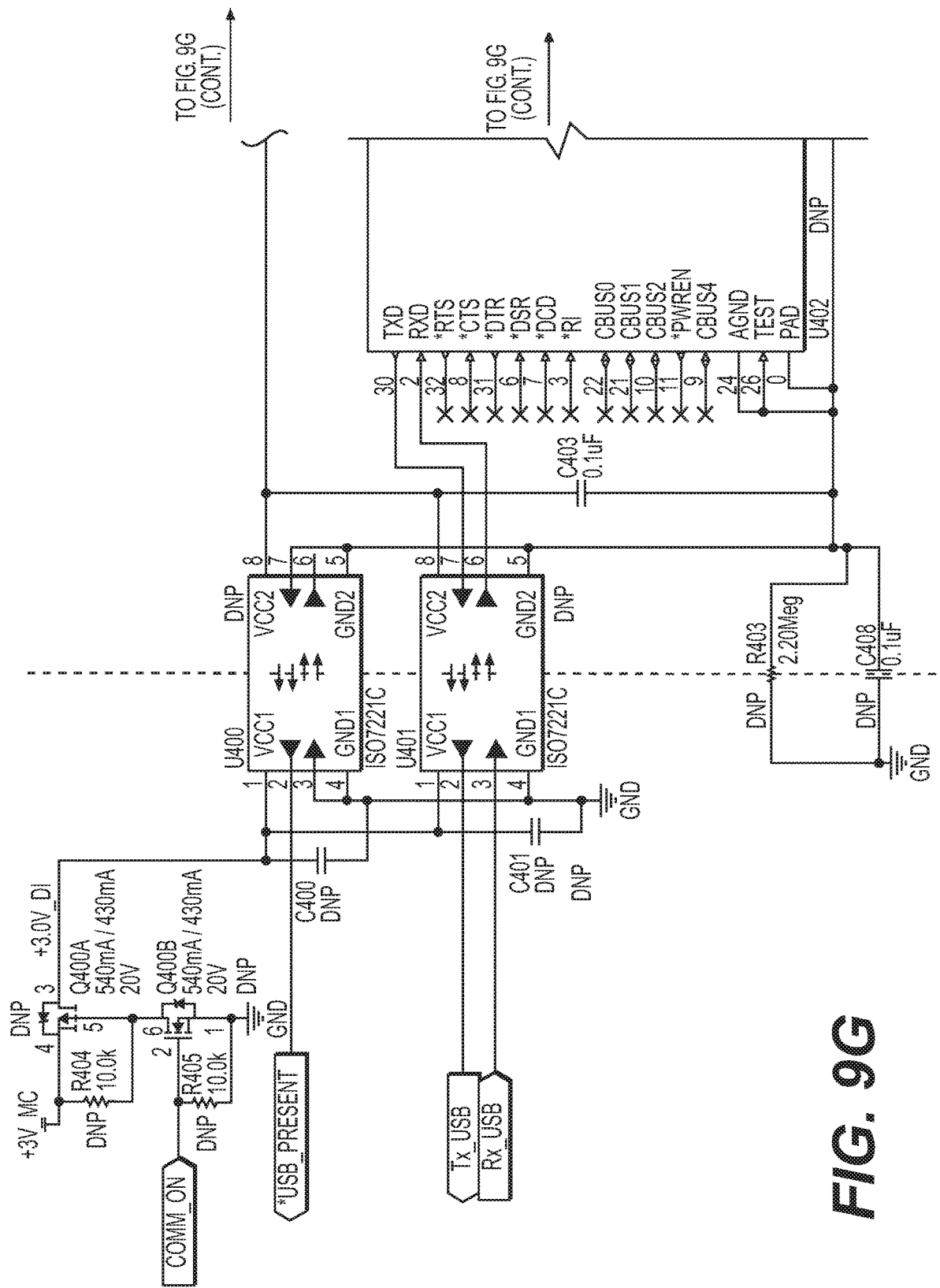

FIG. 9G shows a detailed diagram of the USB communication circuit 906 that is used to access the main controller 910, e.g., for testing and development. The circuit may not be available for access by a user during normal runtime operation.

FIGS. 9H, 9I, 9J, and 9K show detailed diagrams of the biopotential acquisition circuit 902. The biopotential acquisition circuit 902 includes an analog-to-digital converter IC 916 (shown as device "ADS1294" 916) configured with an integrated ECG front end circuit comprising a programmable gain amplifier. To this end, analog-to-digital converter IC 916 includes both the gain amplifier 110 and the analog-to-digital conversion circuit 114 in a single integrated circuit. Other configuration of the analog-to-digital conversion circuit may be used, though the analog-to-digital conversion circuit has at least about 17 bits of resolution, preferably about 24 bits.

Figure 9H:
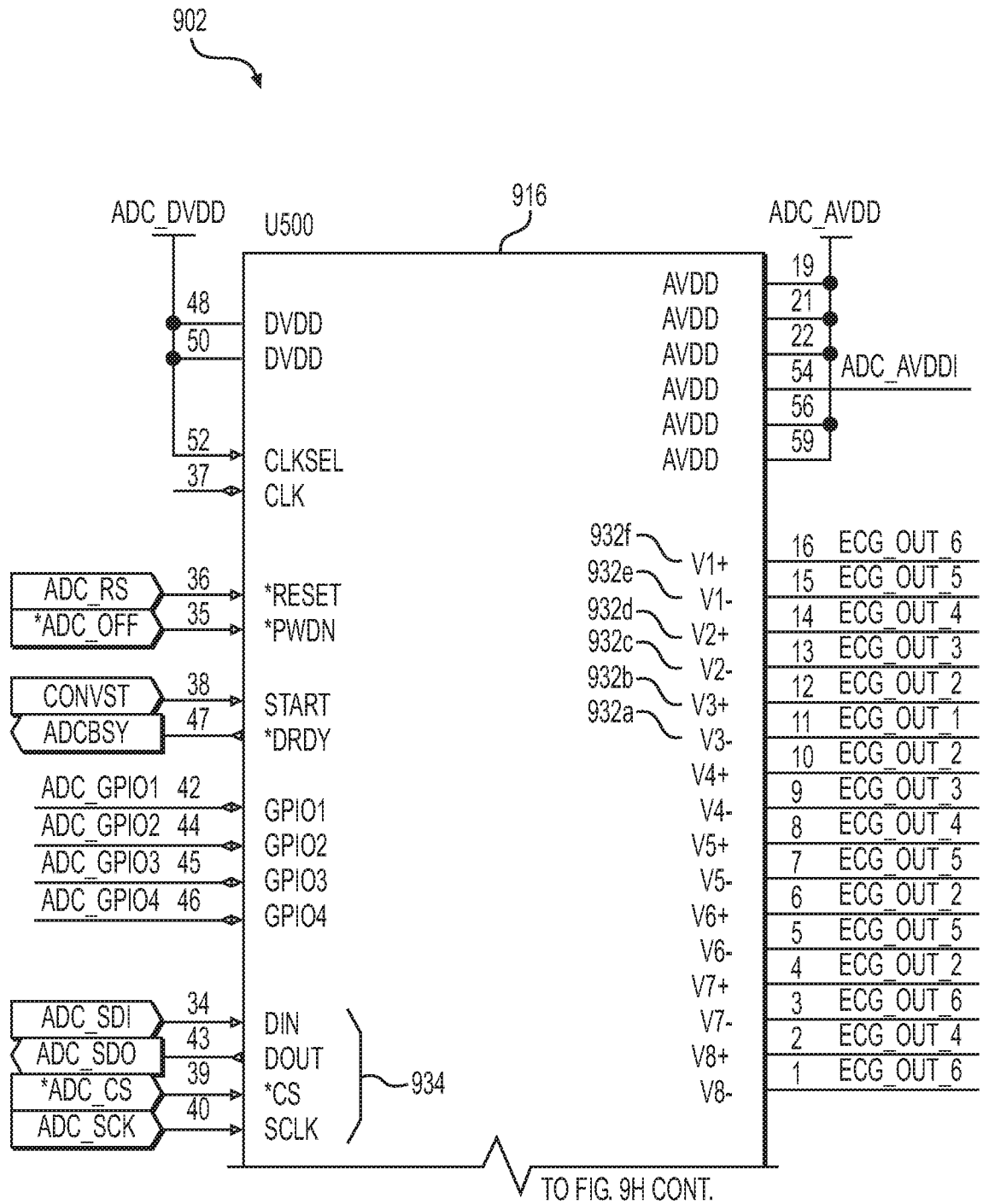
Figure 9H:
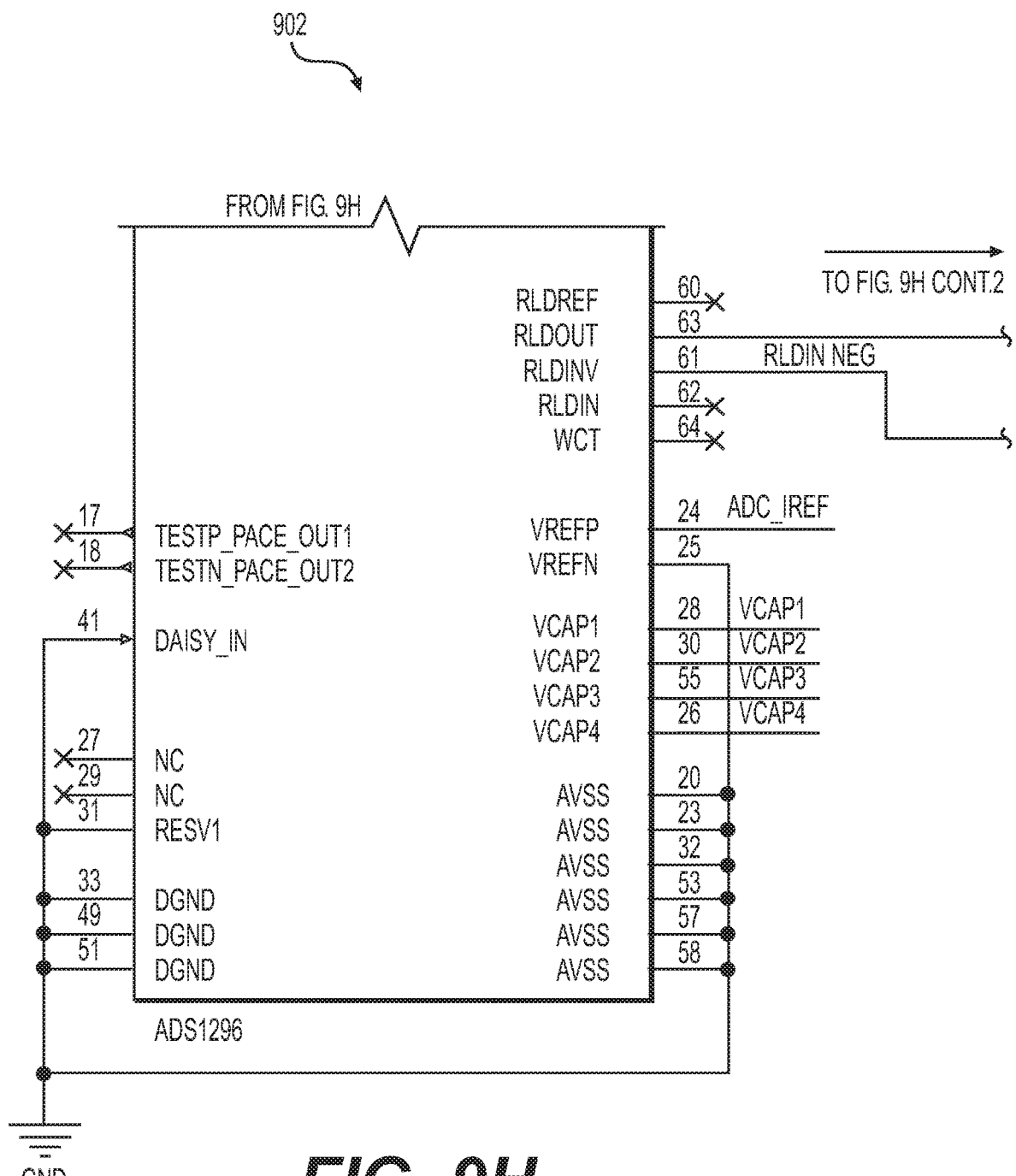
Figure 9I:
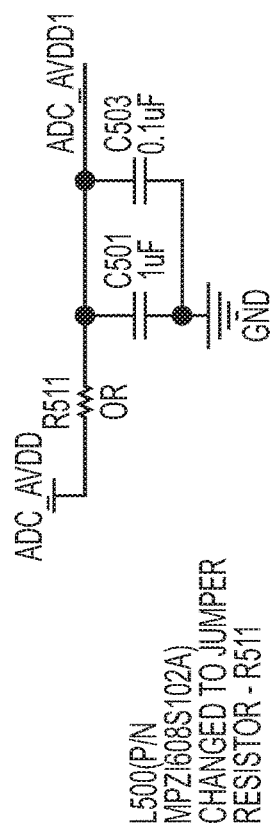
Figure 9J:
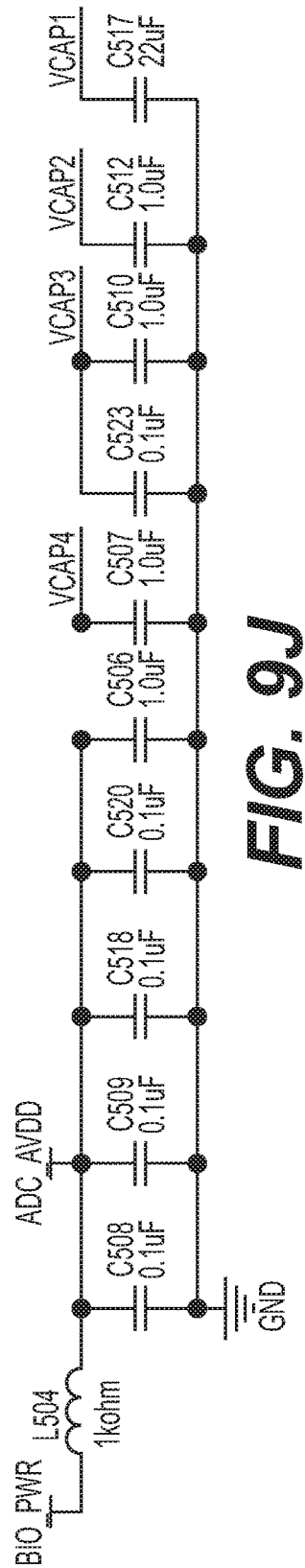
Figure 9K:
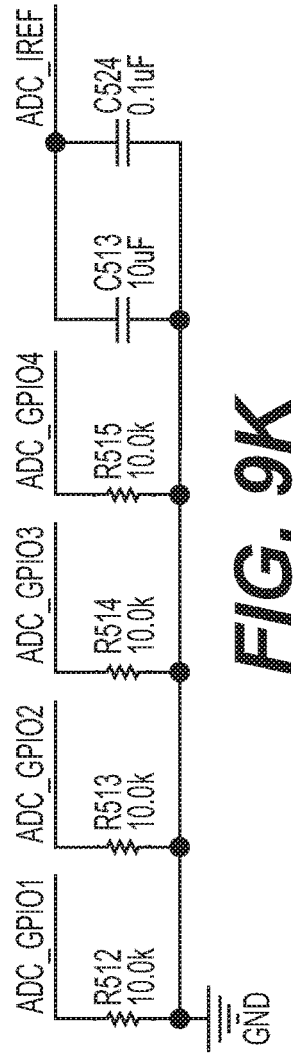
Figure 9O:
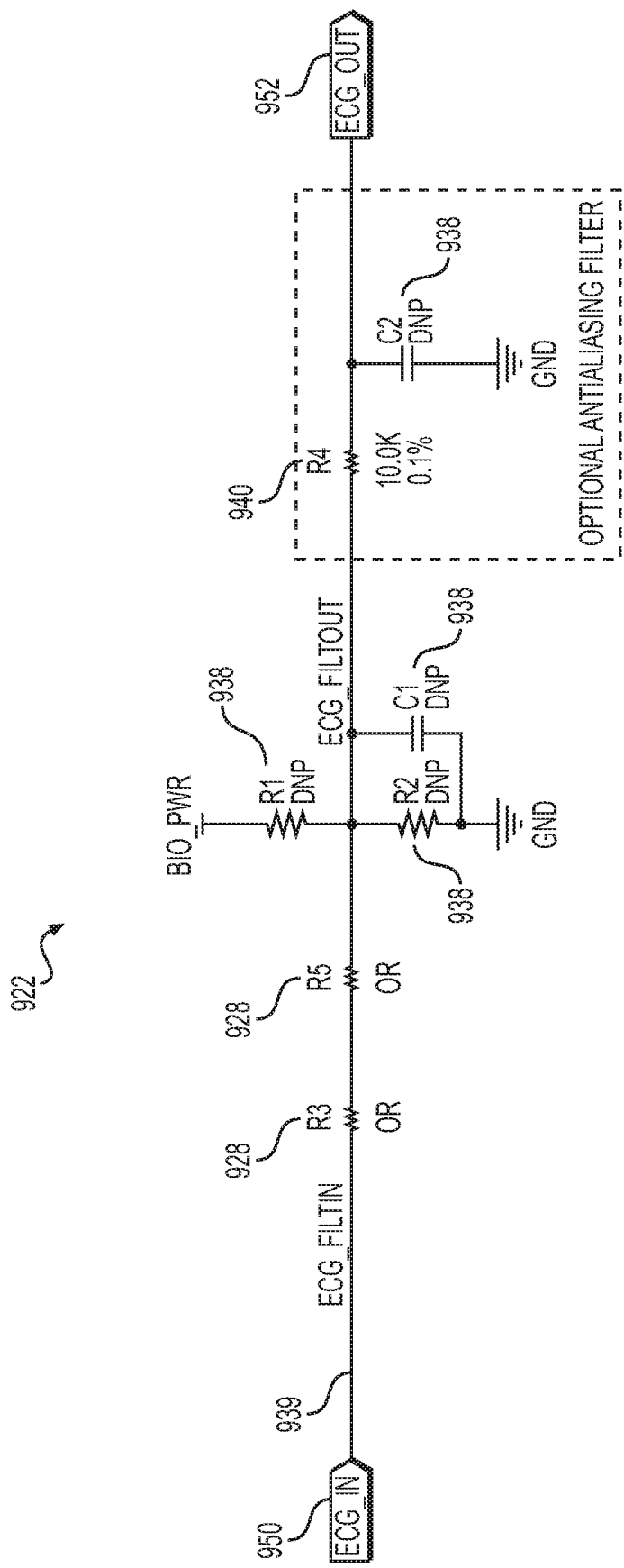

Specifically, FIG. 9H shows the wiring of the analog-to-digital converter IC 916, to the main controller 910 and the biopotential channel circuit 922 of FIG. 9O via the control lines and data lines. Further, in FIG. 9H, a single cable terminal block 924 (corresponding to terminals 404a, 404b) is provided to couple to a cable assembly comprising cables 124a-124e that couples to the electrodes 106a-106e. The cable terminal block 924 includes i) pins (shown as pin 1, 3, 5, 7, and 9 of J500) for 3 pairs of differential inputs and ii) a pin 926 (shown as pin 4 of J500) for the outer shield drive. Each of pins 1, 3, 5, 7, and 9 of J500 connect to respective inputs 928a-928f of respective biopotential channel 922. The biopotential channels 922 are repeated 6 times to provide outputs 930a-930f to the inputs 932a-932f of the analog-to-digital converter IC 916. The analog-to-digital converter IC 916 provides the acquired signal 112 over a digital bus to main controller 910 via lines 934 (see FIGS. 9A and 9E).

FIG. 9O shows a detailed diagram of an example biosignal acquisition channel 922, as shown in connection with FIG. 9H. Notably, there are no active components or low-pass filtering in the signal path 940 between the input 950 and output 952 of the channel 922. To this end, there is a lack of active filters and/or circuit elements that can introduce non-linear distortions into the signal path. In FIG. 9O, components 928 are shunts serving as a jumper and components 938 are not placed and are provided as optional components within the prototype printed circuit board. Indeed, only a single anti-aliasing circuit is included in the signal path 939. The anti-aliasing circuit includes two resisters 940 from two channels 922 connected by a capacitor (shown as 942a, 942b, and 942c in FIG. 9H). The number of components (e.g., resisters 940 and capacitor 942a-942b) is preferably minimized to improve noise performance, though more than one of each of these components may be used. The resisters 940 for a channel pairs are 10 k-Ohm and also serves to protect the input of the analog-to-digital converter IC 916.

One or more ferrite 928 (e.g., ferrite bead) may be placed in the signal path to suppress high frequency noise (e.g., radio-frequency noise). It is noted that radio-frequency signals are generally in the MHz range which is several orders of magnitude higher than the biopotential signals of interest, which are in the KHz to hundreds of KHz.

To provide defibrillation protection, a defibrillator protection circuit, or equivalent thereof, is placed in the signal path 940. As shown in FIG. 9L, a combined defibrillation, surge, and ESD protector circuit is used. FIG. 9L shows a detailed diagram of a defibrillator protection circuit (shown as 948a, 948b). An example combined defibrillation, surge, and ESD protector circuit is the MAX30034 protection devices, manufactured by Maxim Integrated (San Jose, Calif.). In FIG. 9H, a limiting resister (R520, R519, R524, R517, R518, and R521) is shown placed in the signal path 940 used with the ESD protector circuit.

FIGS. 9I, 9J, and 9K each shows the detailed diagram of the capacitive decoupling and filtering of the power plane and ground plane of the analog-to-digital conversion circuit.

FIG. 9M and FIG. 9N show detailed diagrams of power conditioning circuits that provide reference voltages to the biopotential amplifier circuits as shown in FIG. 9L and to the biopotential amplifier circuit as shown in FIG. 9H.

Noise Reduction Circuit

Figure 9P:
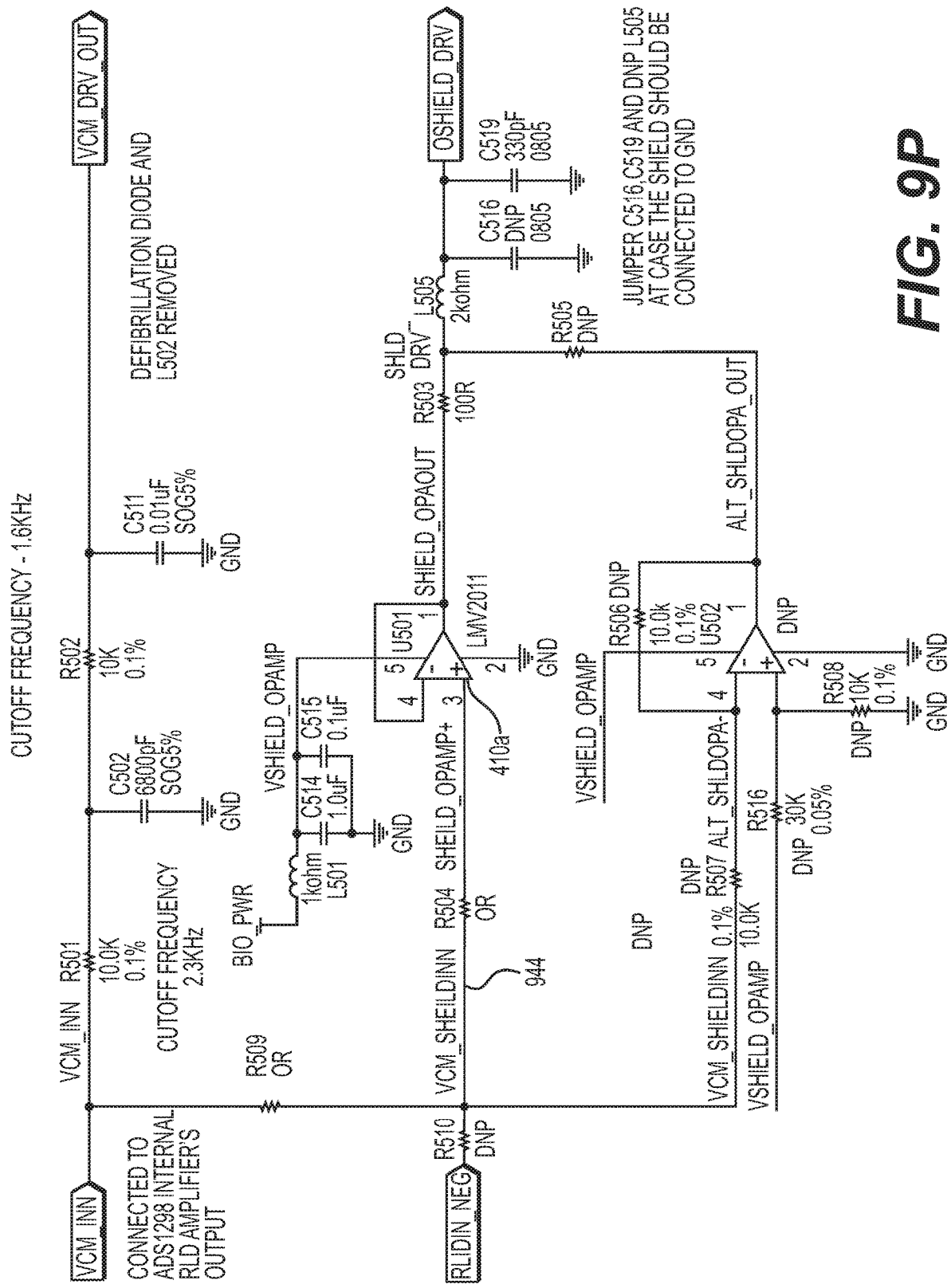
Figure 9Q:
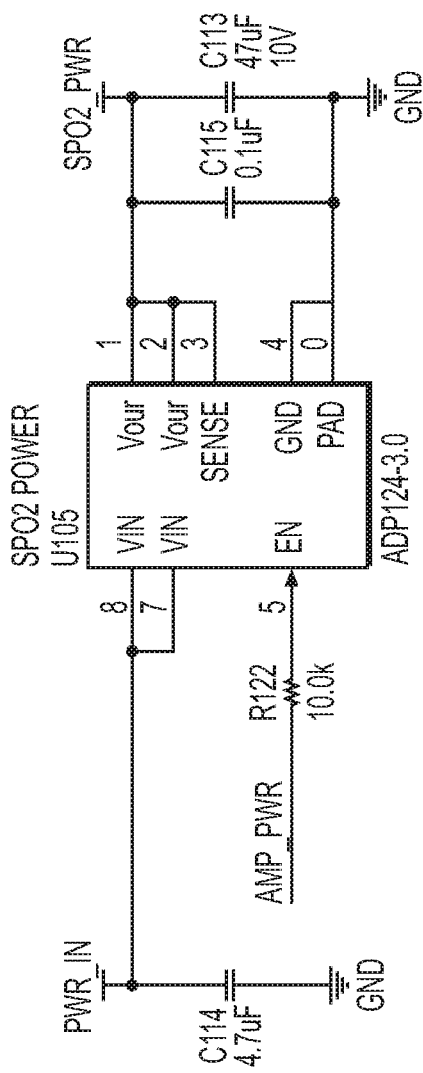
Figure 9R:
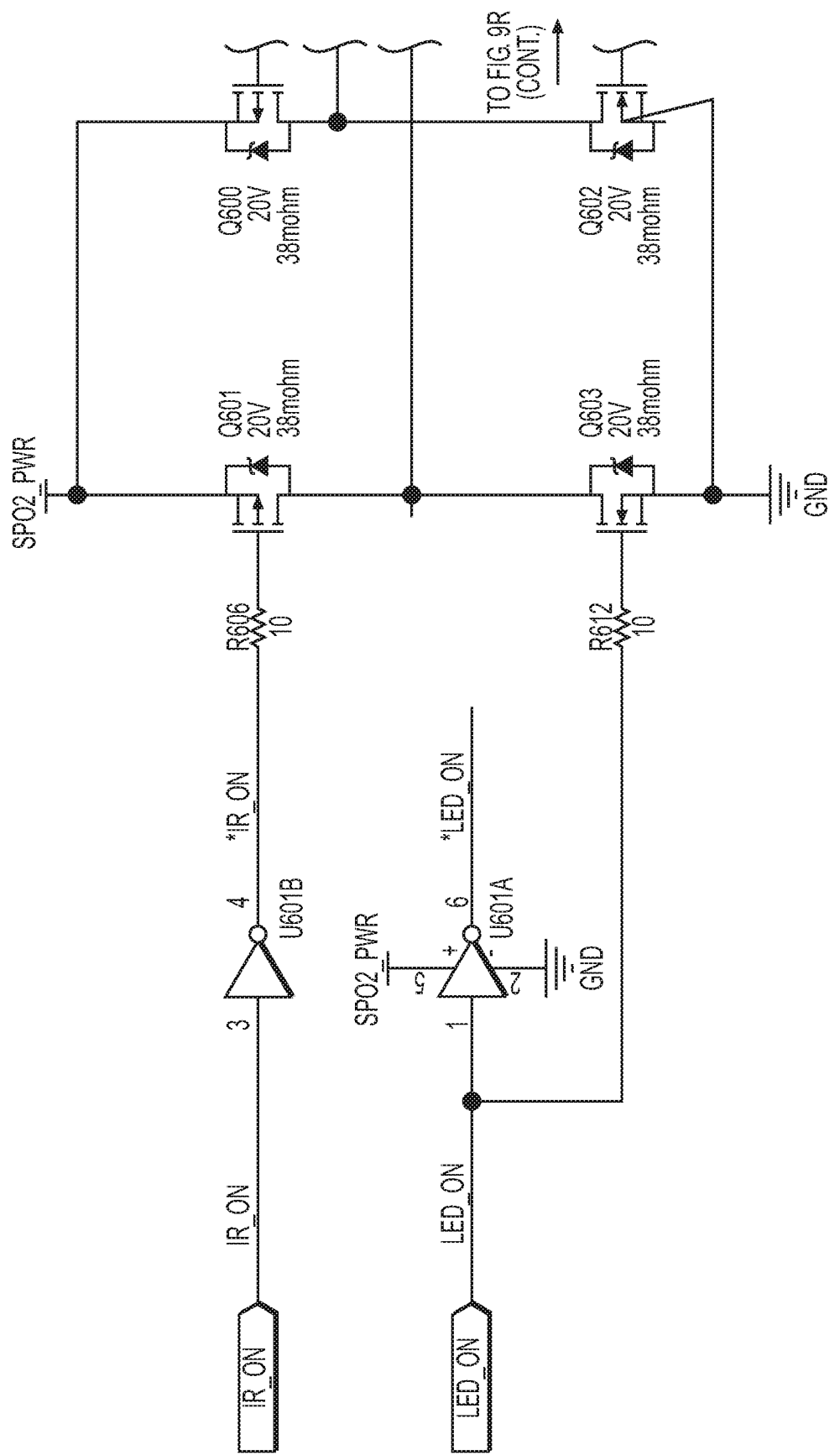
Figure 9R:
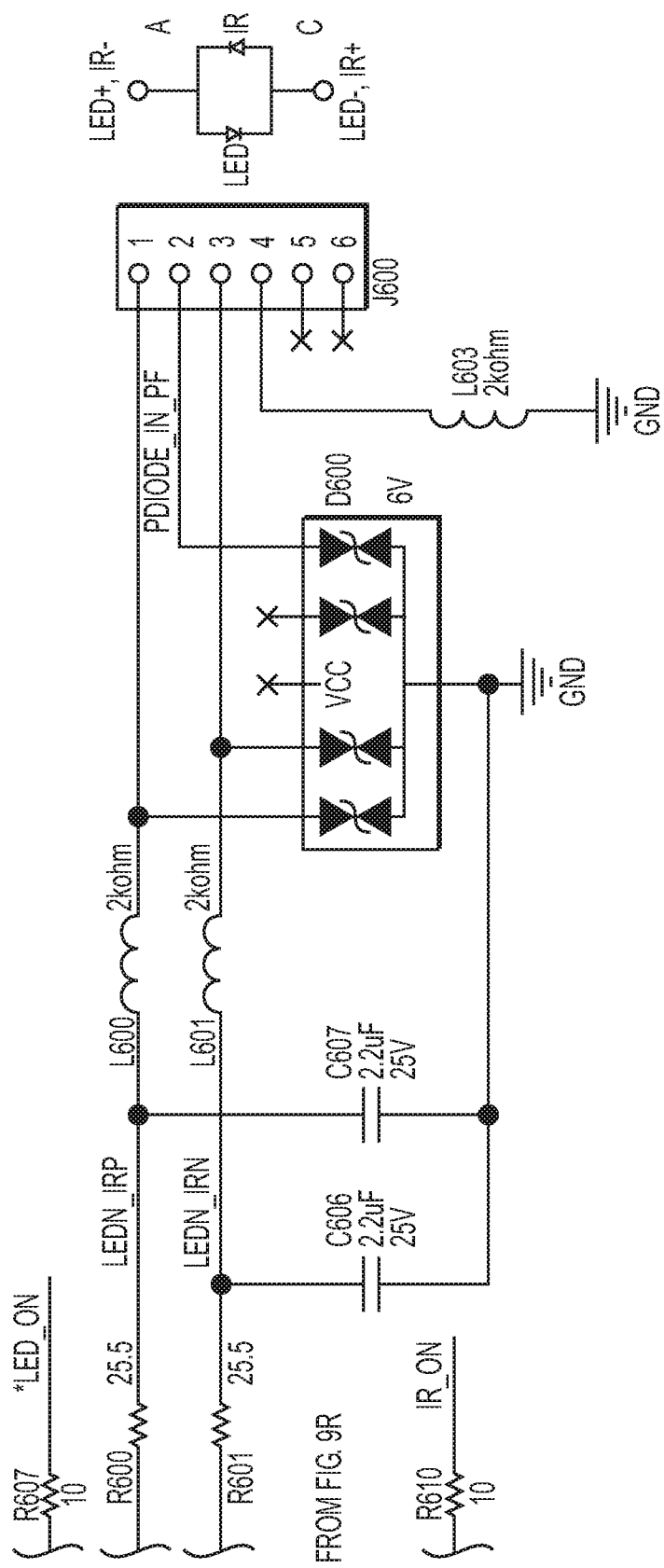
Figure 9S:
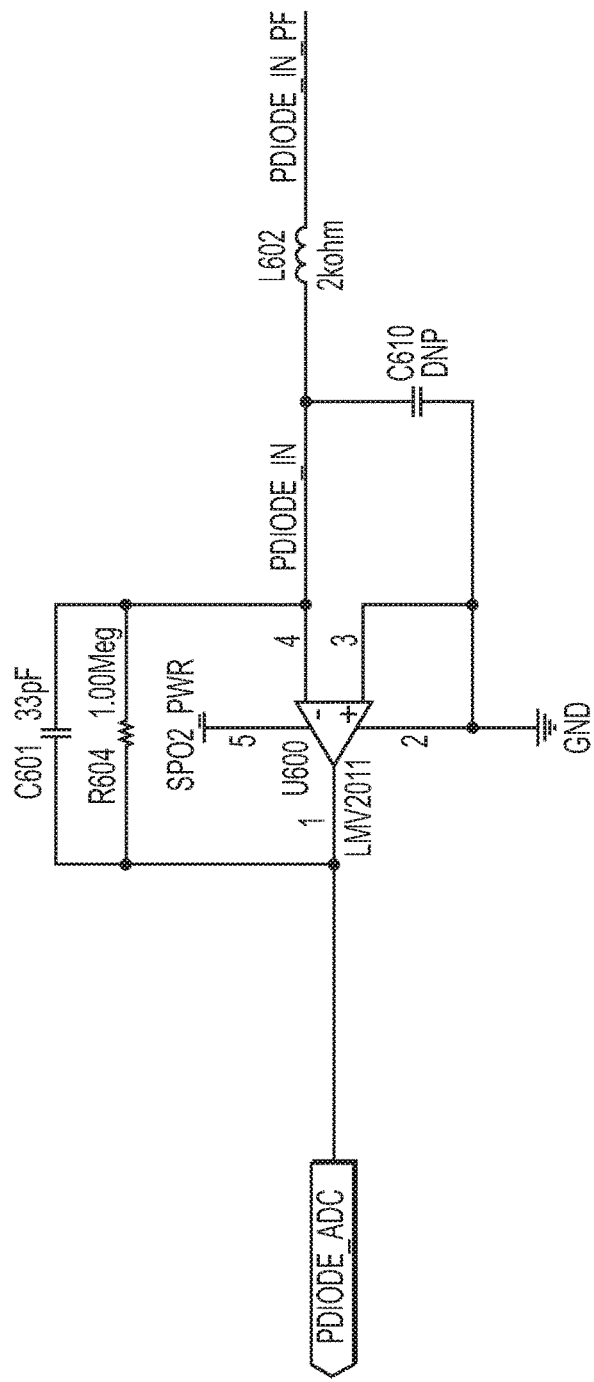
Figure 9T:
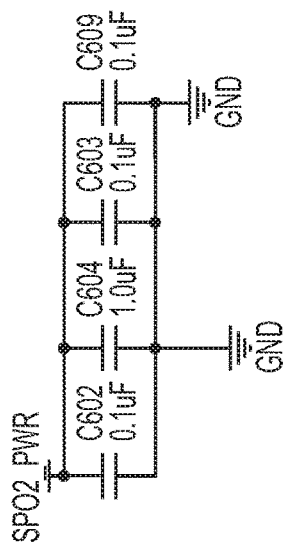

FIG. 9P shows a detailed diagram of an example noise rejection circuit that applies a common-mode voltage reference to the body.

The goal of the noise rejection system is to eliminate environmental noise currents flowing in the patient's body that might interfere with biopotential measurement. Noise may be generated from a variety of environmental sources; including consumer electronics, cell phones, and the local AC power system. Any or all of these may generate voltages at the measurement electrodes that will render a patient's biopotential un-measurable or more difficult to measure.

To combat environmental noise, the BSA Instrument hardware employs a common mode amplifier to actively applies the patient's body with a varying potential (e.g., between −1.0 VDC and −2.0 VDC or +1.0 and +2.0 VDC) or a constant potential (e.g., a value between +1.5 VDC or −1.5 VDC) and thus shunt environmental noise currents during normal operation. In FIG. 9P, the common mode amplifier is connected to an internal amplifier output 946 of the analog-to-digital converter IC 916 (FIG. 9H). In other embodiments, a separate amplifier stage may be used to drive the patient's body to other potentials.

The BSA Instrument hardware further includes an operational amplifier, U501 (shown as "LMV2011" 410a) that drives the outer shields 406a-406f of the cables 124a-124f with the same potential as that of the common mode amplifier. As shown in FIG. 9P, the input 944 of the operational amplifier 410a is also coupled to the internal amplifier output 946 of the analog-to-digital converter IC 916 (FIG. 9H). The analog-to-digital converter IC 916 is configured to generate constant potential (e.g., $1.5V_{DC}$). In other embodiments, the analog-to-digital converter IC 916 is configured to generate an average output of the readings of the inputs 932a-932f of the analog-to-digital converter 916.

FIGS. 9Q, 9R, 9S, and 9T, are detailed diagrams of components of the oximetry circuit (shown as 904a, 904b, 904c, and 904d). The oximetry circuit 904 is configured to operate with a pulse oximeter (PO2) sensor to collect oxygen saturation readings. In some embodiments, the oxygen saturation readings is collected with at least 12 bits of resolution and at a minimum rate of 200 samples per second.

Another example of the wide-band cardiac phase gradient signal acquisition system is described in WO2017/033164, published Mar. 2, 2017, which is incorporated by reference herein in its entirety.

Example BSA Board

Figure 10A:
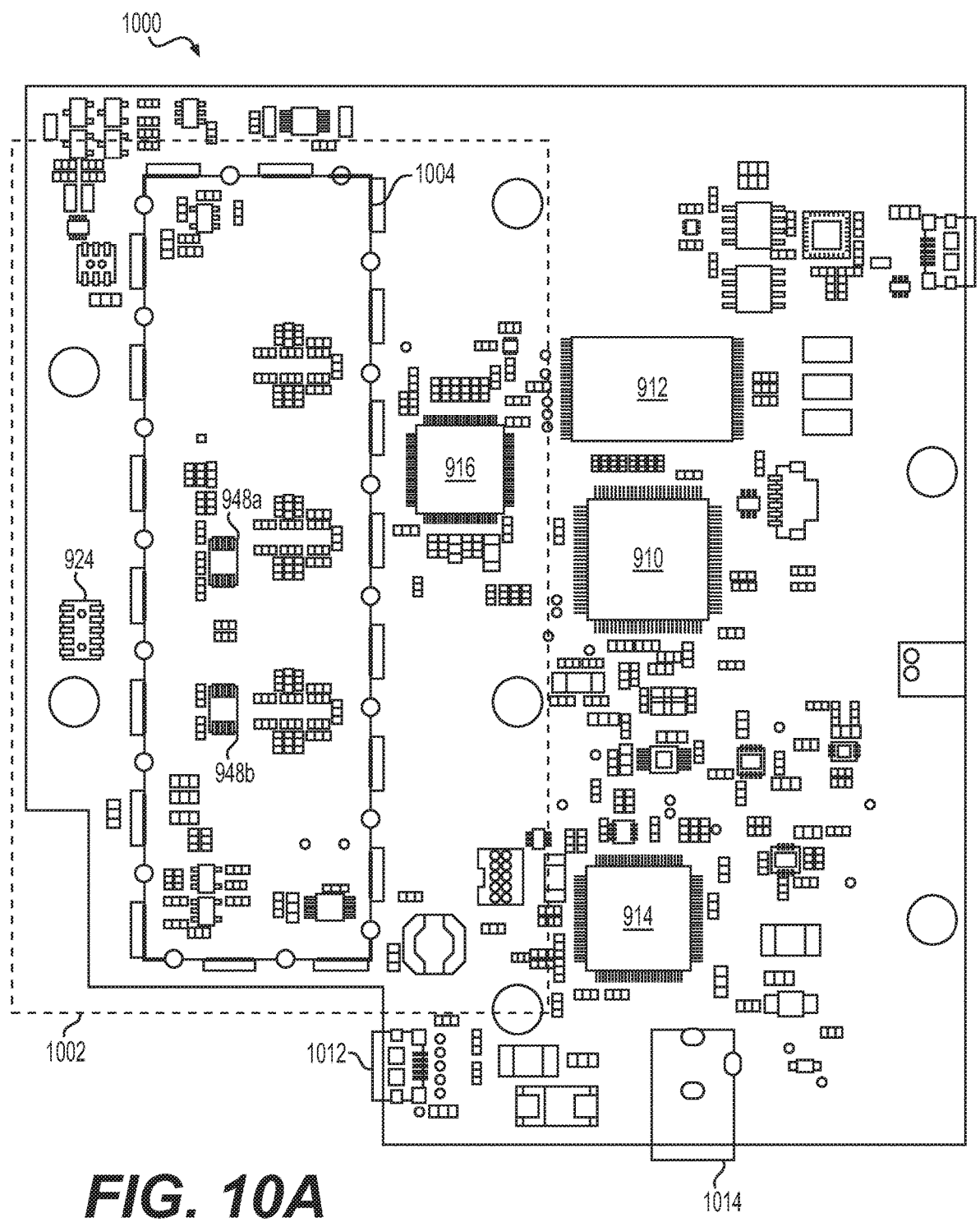
FIG. 10A is a diagram of an example biosignal acquisition ("BSA") board that includes the differentially-acquired wide-band cardiac phase gradient signal acquisition system of FIG. 9 in accordance with an embodiment.

FIG. 10A is a diagram of an example biosignal acquisition ("BSA") board 1000 comprising multi-layer printed circuit board that includes the wide-band cardiac phase gradient signal acquisition system of FIG. 9 in accordance with an embodiment. The BSA board 1000, in some embodiments, includes a conductive shield 1004 (e.g., a grounded shield cage) that surrounds the mixed-signal front-stage circuitries of the biosignal acquisition channel 104 arranged between the cable terminal block 924 and the analog-to-digital converter IC 916. The conductive shield 1004, in some embodiments, is electrically coupled to reference ground plane.

Figure 10B:
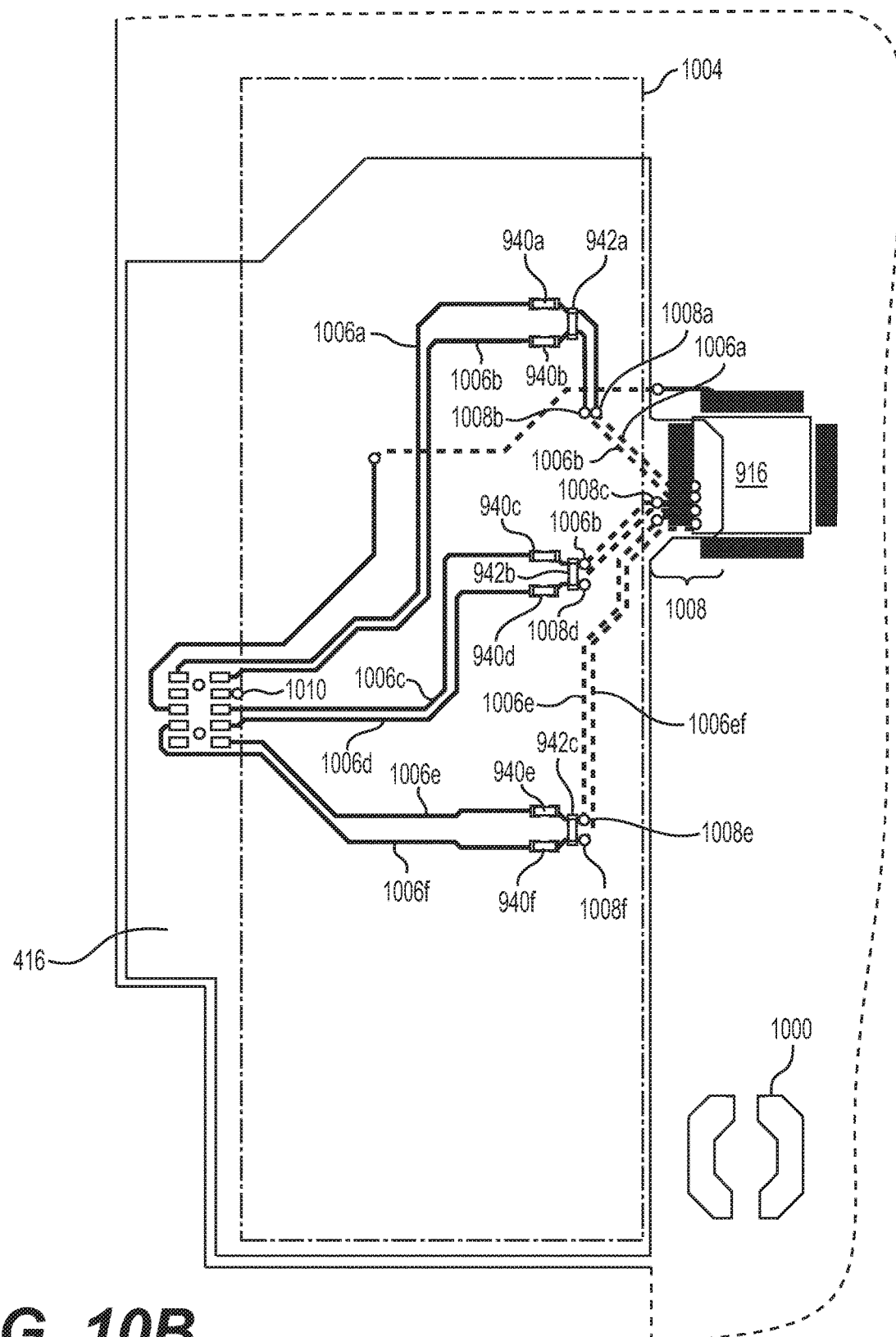
FIG. 10B is a diagram showing details of tracing of the example biosignal acquisition board in accordance with an embodiment.

FIG. 10B shows a diagram of a detailed view 1002 of FIG. 10A of the mixed-signal front-stage circuitries of the biosignal acquisition channel 104 arranged between the cable terminal block 924 and the analog-to-digital converter IC 916.

In FIG. 10B, three sets of tracing pairs for the three-differential channels are shown, including tracings 1006a, 1006b, tracings 1006c, 1006d, and tracings 1006e, 1006f in which tracings 1006a, 1006b are connected to biopotential channel inputs 928a and 928b; tracings 1006c, 1006d are connected to biopotential channel inputs 928c and 928d; and tracings 1006e, 1006f are connected to biopotential channel inputs 928e and 928f. The tracings 1006a-1006f are arranged across two layers (shown in solid and in dash) connected by vias 1008a-1008f.

As noted above, only a single anti-aliasing circuit is included in the signal path 940 (and, in some embodiments, a defibrillation protection circuit). The anti-aliasing circuit includes two resisters 940 from two channels 922 connected by a capacitor (shown as 942a, 942b, and 942c in FIG. 9H). The number of components (e.g., resisters 940 and capacitor 942a-942b) is minimized to improve noise performance. The resisters 940a-940f for a given channel pair are 10 k-Ohm and serve to protect the input of the analog-to-digital converter IC 916 by increasing the a common mode rejection ratio for the inputs of the analog-to-digital converter IC 916.

Cable-Drive Voltage Plane

In another aspect, a shield drive voltage circuit is used to facilitate low noise and low interference operation of the acquisition system. FIG. 10B further shows an example shield-drive voltage plane 416. The shield-drive voltage plane 416 is connected to a shield-drive amplifier 410a that drives the outer shields 406a-406f of the cables 124a-124f and provides a return pass for noisy current induced on the outer shield 406a-406f. The shield-drive voltage plane 416 is electrically coupled to terminal 924 through vias 1010 that connects to a pin of the terminal 924 that connects to outer shields 406-406f of the cables 124a-124f. In some embodiments, the cable includes a trunk segment having an outer shield and includes a set of branch segments comprising multiple branch cables extending from the trunk segment. Each of the branch cables includes an outer shield that connects to the outer shield of the trunk segment.

In some embodiments, the multi-layer printed circuit board comprises seven layers in which the top "first" layer and "third" layer are designated for signal tracings, the "second" layer and bottom "seventh" layer has a reference ground plane, and the "fourth" layer includes the cable-drive voltage plane 416. Indeed, the "second" and "seventh" layer of the board serve as a reference ground plane, and the "fourth" layer serves as the cable-drive ground plane. Layer "five" may be used as a power layer.

The top "first" layer and "third layer" comprise signal layers having pairs of conductive traces (e.g., low-impedance traces) running substantially through the layers and across one or more regions coincident and coplanar to the cable-drive voltage plane 416. In some embodiments, the conductive traces are 0.254 mm wide (0.001 inch wide). Other trace thicknesses may be used depending on the material to facilitate low-impedance operations. The pair of conductive traces electrically couples, across the connector (e.g., terminal 924) directly or indirectly affixed to the multi-layer printed circuit, to the ends of signal-carrying conductors of the cables 124a-124f and also to the differential input pins of the analog-to-digital converter IC 916 (having an analog-to-digital conversion circuit and amplifier stage). The cable-drive voltage plane 416 (as the second ground layer) electrically couple, over terminal 924, to the outer shield 406a of cable 124a, the outer shield 406b of cable 124b, the outer shield 406c or cable 124c, the outer shield 406d of cable 124d, the outer shield 406e of cable 124e, and the outer shield 406f of cable 124f. The cable-drive voltage plane 416 overlaps with a substantial length of the tracings 1006a-1006f and overlaps in part (shown as 1008) over the footprint of the analog-to-digital converter IC 916. Though shown being routed across two layers, in other embodiments, the tracings 1006a-1006f may be routed over a single layer of the multi-layer printed circuit board.

In some embodiments, the cables 124a-124f terminate at a single cable-pin connector (shown in FIG. 11A) that is configured to releasably mate to the connector (e.g., terminal 924) of the signal acquisition board 1000.

To allow for even more improved low-noise operation, each conductive trace of the pair of conductive traces 1006a-1006f is arranged with a similar length and has a same number of via as the corresponding trace (as, for example, shown in FIG. 10B) so as to have a substantially similar impedance characteristics with the corresponding trace of the differential pair. Further, each pair of conductive traces are arranged, on each layer that they are routed, in close proximity (as, for example, shown in FIG. 10B) to one another such that substantial lengths of each conductive trace of the pair of conductive traces are substantially parallel to one another.

Further, the conductive traces 1006a-1006f and cable-drive voltage plane 416 are arranged on a portion of the board 1000 that is, in essence, isolated from the processing and communication components (e.g., 910, 912, 914) to minimize interference and noise generated from such circuits.

Referring still to FIG. 10A, the geometric configuration of the conductive shield 1004 serving as a grounded shield cage is shown. The conductive shield 1004 spans a substantial portion of the cable-drive voltage plane 416 (as the second ground layer) so as to encapsulate a substantial portion of the pair of conductive traces 1006a-1006f.

Indeed, the pair of conductive traces 1006a, 1006b forms a part of a first differential input channel of the signal acquisition board of a set of three differential input channels. As shown in FIG. 10B, the second differential input channel also comprises a pair of conductive traces 1006c, 1006d (and the third differential input channel comprises a pair of conductive traces 1006e, 10060 running substantially through signal layers across a region coincident and coplanar to the cable-drive ground plane.

Referring back to FIG. 10B, the BSA board 1000 is connected, via connector 1014, to a battery that provides power to the acquisition circuit. The BSA board 1000 includes a USB connector 1012 that provides an interface to the microcontroller.

Figure 10C:
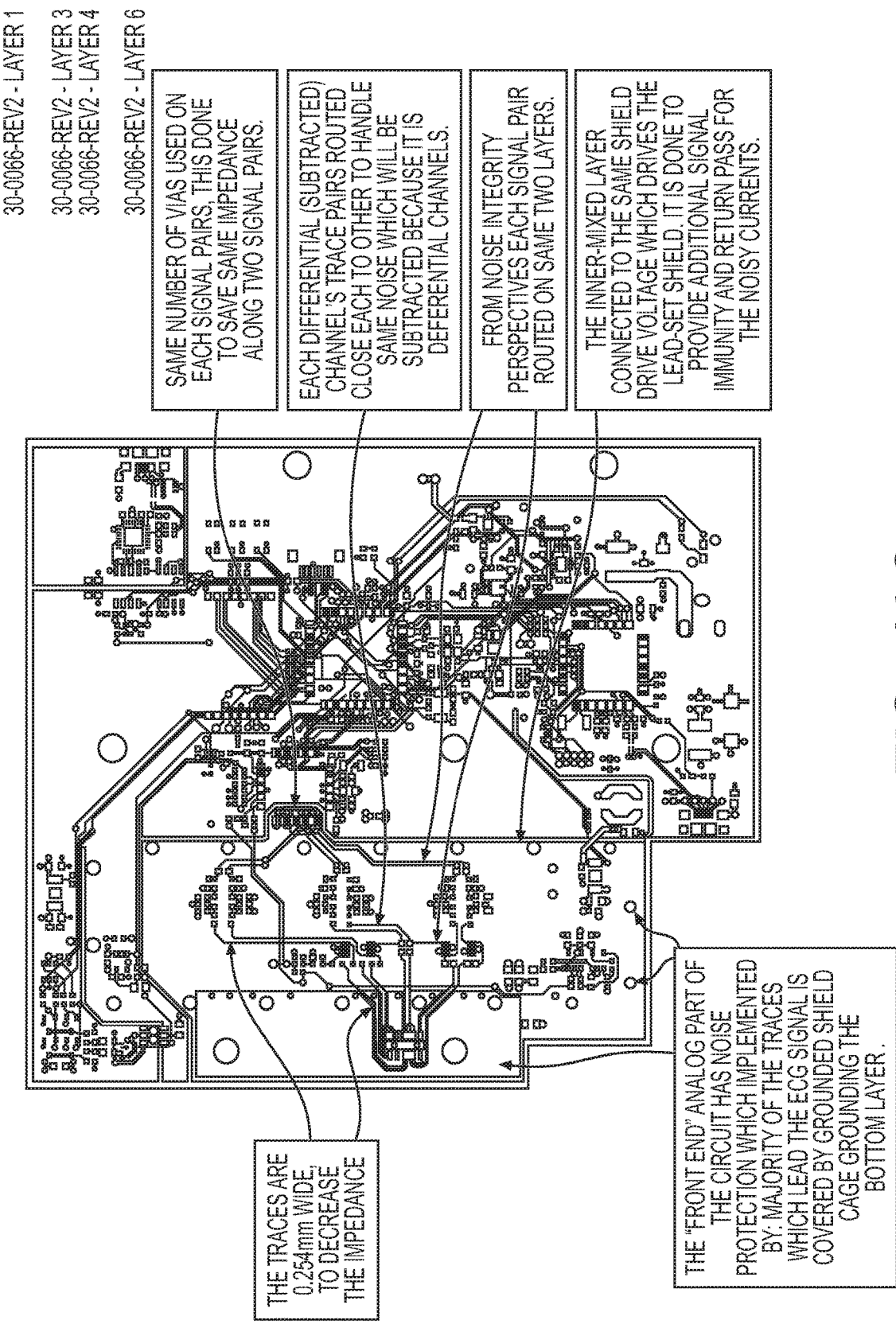
FIGS. 10C and 10D shows additional views of the biosignal acquisition board.
Figure 10D:
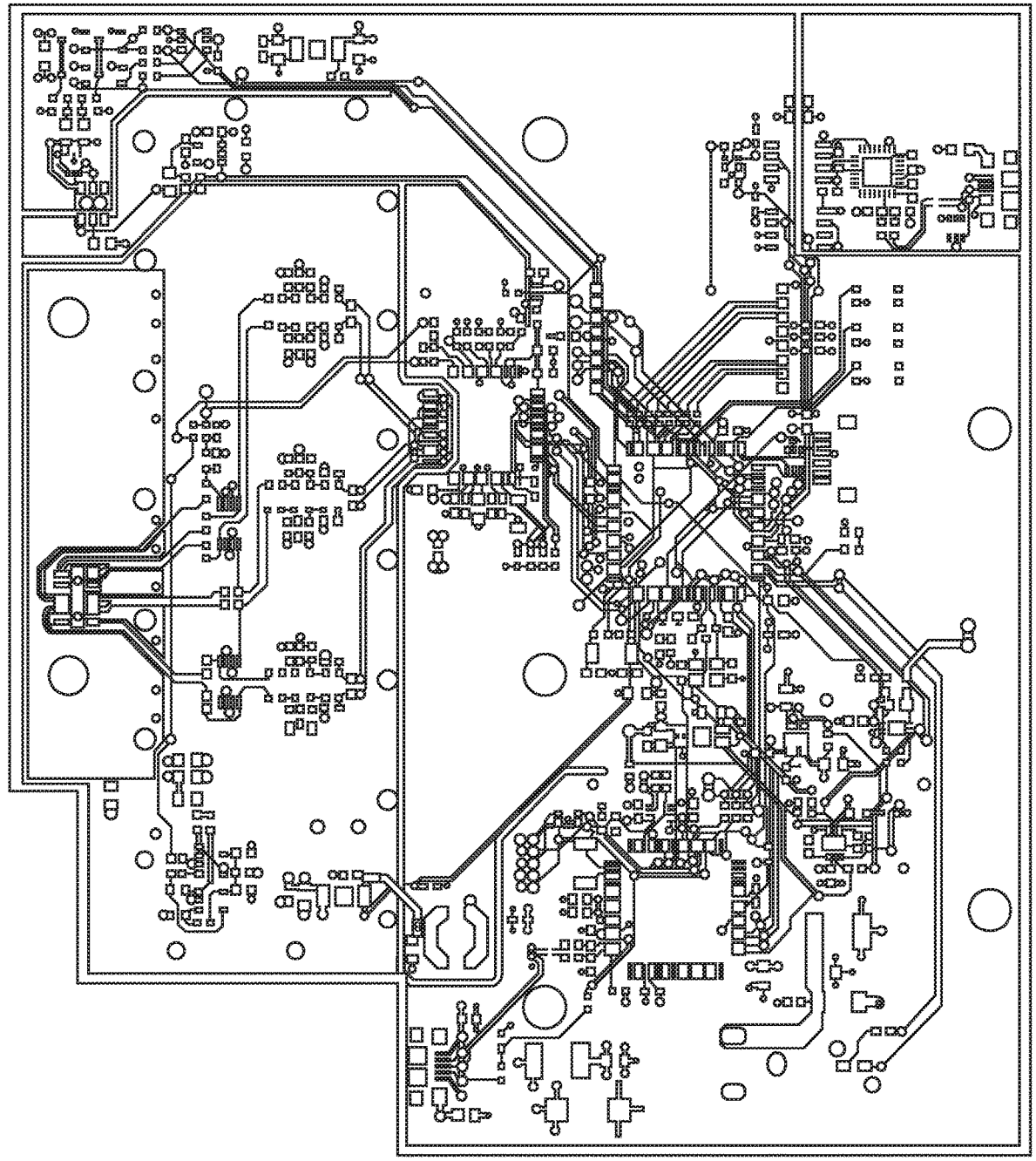

FIGS. 10C and 10D shows additional views of the bio-signal acquisition board 1000. In FIG. 10C, trace routings and plane boundaries of layers 1, 3, and 4 are shown. In FIG. 10D, trace routings and plane boundaries of layers 1, 3, 4, and 6 are shown. The routings as shown in FIGS. 10C and 10D corresponds to the component placements described in relation to FIG. 10A.

Figure 11A:
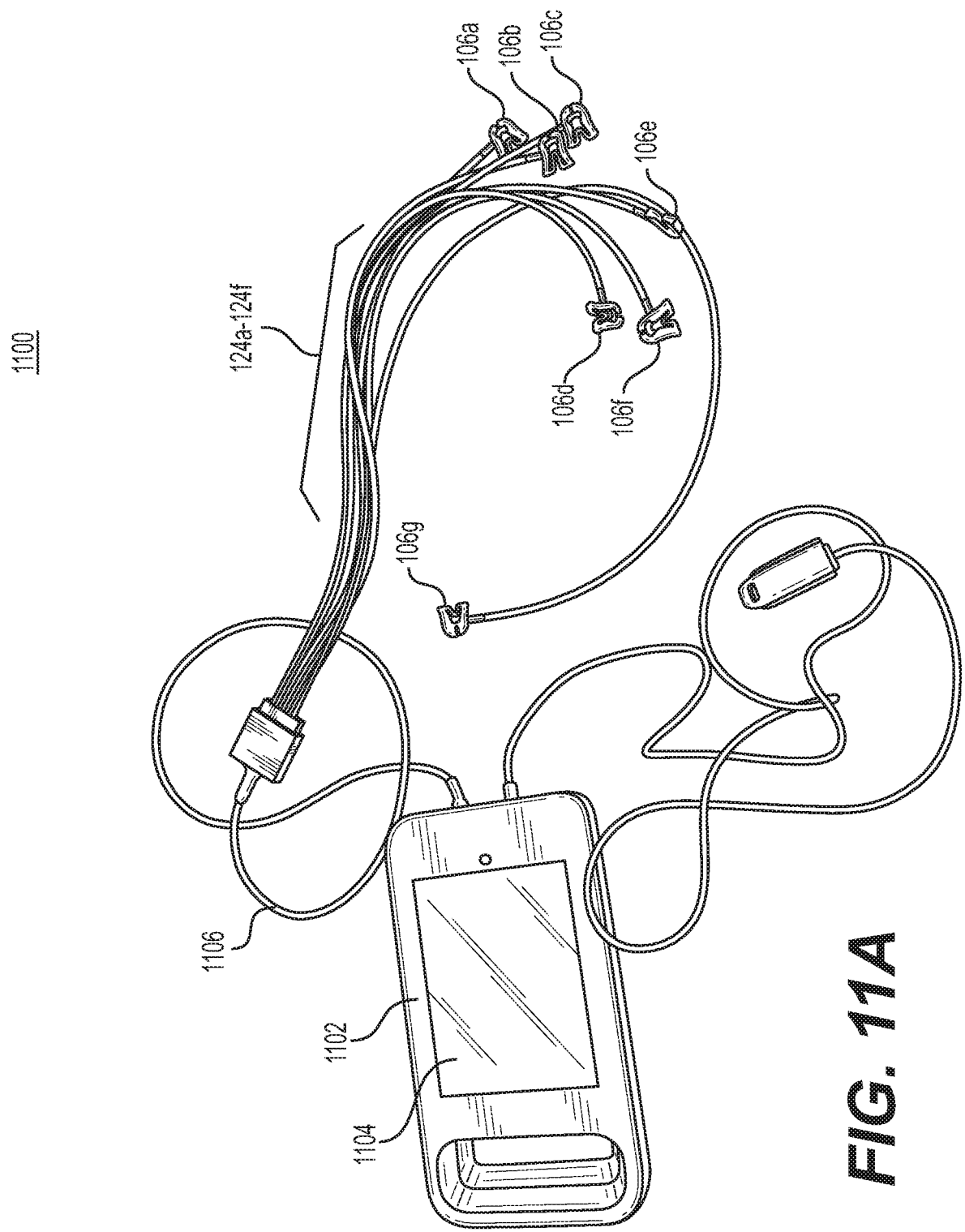
FIG. 11A is a diagram of an example BSA instrument that includes the BSA board of FIG. 10A in accordance with an embodiment.

FIG. 11A is a diagram of an example BSA instrument 1100 that includes the BSA board 1000 of FIG. 10A in accordance with an embodiment. The BSA system 1100 includes a housing 1102 that houses a computing device 1104 (e.g., a portable computing device) that interfaces with the BSA board 1000 (see FIG. 10A). The housing 1102 further includes a connector 1106 that connects to the cables 124a-124f associated with the surface electrodes 106a-106g. As shown in FIG. 11A, surface electrodes 106a-106f are used for the acquisition of the wide-band cardiac phase gradient signals and surface electrode 106g is the common-mode reference electrode.

Figure 11B:
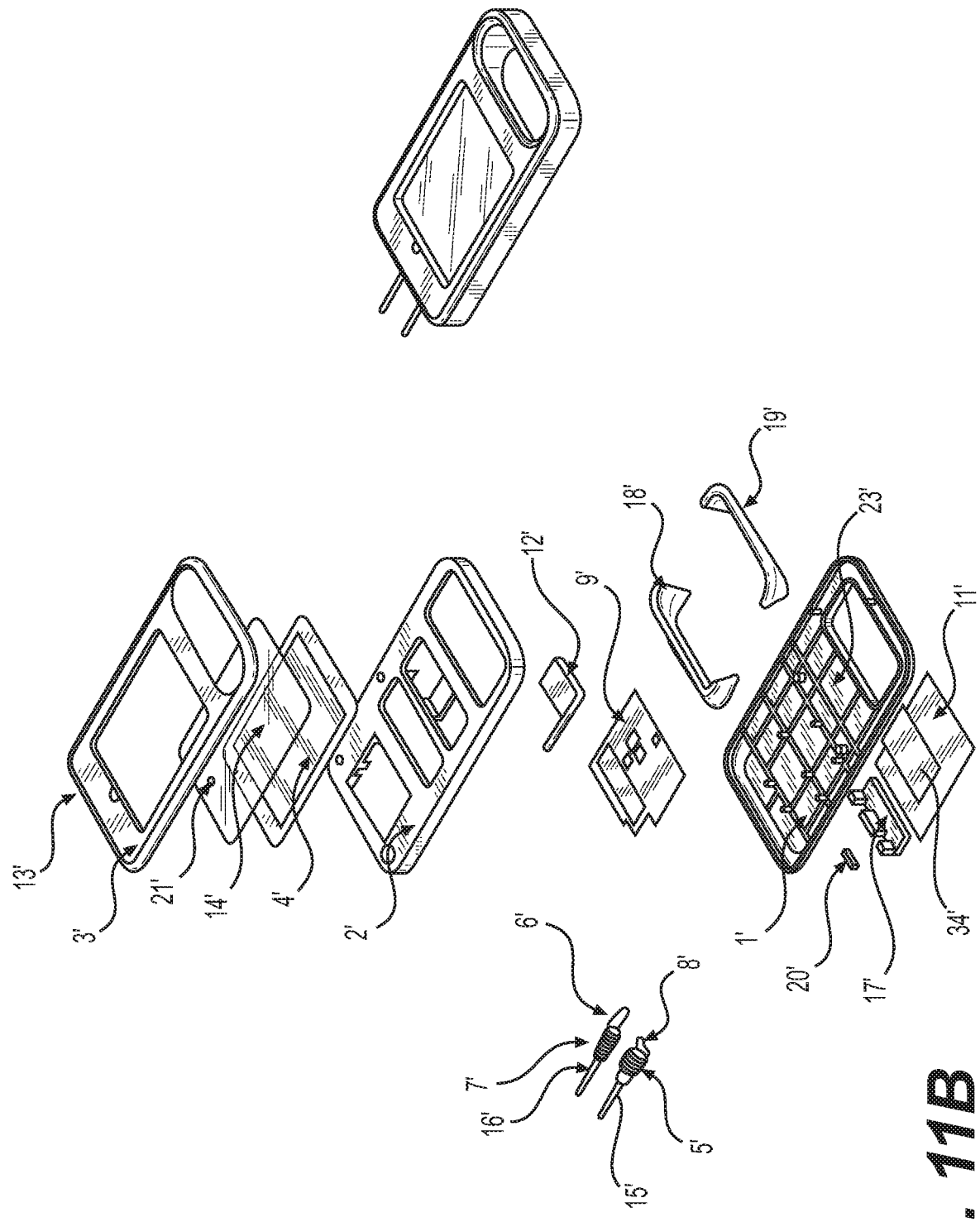
FIG. 11B is a diagram with an exploded unassembled view of an example BSA instrument that includes the BSA board of FIG. 10A in accordance with an embodiment.

FIG. 11B is a diagram with an exploded unassembled view of an example BSA instrument 1100 that includes the BSA board of FIG. 10A in accordance with an embodiment.

Table 1 shows example components of the BSA instrument 1100. FIG. 12

| Item No. (FIG. 11B) | Description |
| --- | --- |
| 1 | Enclosure Base |
| 2 | BSA Enclosure Middle |
| 3 | BSA Enclosure Top |
| 4 | Computing Device (e.g., Apple IPad Mini2, Wi-Fi Cellular) |
| 5 | Nicolay Mini-12 Instrument Socket, Straight |
| 6 | SpO2 Flex PCA |
| 7 | HiRose SpO2 Connector |
| 8 | Lead Flex PCA |
| 9 | Biosignal Acquisition PCA |

-continued

| Item No. (FIG. 11B) | Description |
| --- | --- |
| 10 | Lightning-Micro USB Cable |
| 11 | BSA Instrument Label |
| 12 | 3.7 V(Nominal) Lithium Ion Rechargeable Battery |
| 13 | Computing Device Interface (e.g., iPad Menu Button) |
| 14 | Tempered Glass Screen Protector |
| 15 | 7 Channel Lead Set |
| 16 | SpO2 Sensor |
| 17 | Enclosure Sensor-Lead Safety Door |
| 18 | BSA Enclosure Handle 1 |
| 19 | BSA Enclosure Handle 2 |
| 20 | Enclosure Sensor-Lead Safety Door Label |
| 21 | Top Light Pipe |
| 23 | Battery Double Sided Foam Tape |

The biopotential signal data, in some embodiments, are normalized as time series data and with the common mode potential removed.

The wide-band cardiac phase gradient signal data are generated as differentials of the acquired biopotential signal data.

Phase gradient signals are generated from two or more biopotential signals acquired from the body, for example, as a differential between two biopotential signals acquired at two locations on the body. To this end, phase gradient signals can be generated for any given pairing of biopotential signals acquired at various electrodes, in addition to those shown herein, for subsequent analysis in phase space.

It should be appreciated that non-linear phase distortions, among other things, as described herein can generate errors in the differential signals, which shows as non-linear noise in the data in phase space. To this end, acquisition of wide-band phase gradient signals without non-linear phase distortions can significantly improve the accuracy and precision of subsequent analysis of the wide-band phase gradient signals in phase space.

Examples of the phase space techniques and analyses that can be performed on the wide-band cardiac phase gradient signal are described in U.S. Publication No. 2016/0378936, entitled "Methods and Systems Using Mathematical Analysis and Machine Learning to Diagnose Disease"; U.S. Publication No. 2015/0216426, entitled "Method and System for Characterizing Cardiovascular Systems From Single Channel Data"; U.S. Pat. No. 9,597,021, entitled "Noninvasive Method for Estimating Glucose, Glycosylated Hemoglobin and Other Blood Constituents"; U.S. Publication No. 2015/0133803, entitled "Noninvasive Electrocardiographic Method for Estimating Mammalian Cardiac Chamber Size and Mechanical Function"; U.S. Pat. No. 9,737,229, entitled "Noninvasive Electrocardiographic Method for Estimating Mammalian Cardiac Chamber Size and Mechanical Function"; U.S. Pat. No. 9,408,543, entitled "Non-invasive Method and System for Characterizing Cardiovascular Systems and All-Cause Mortality and Sudden Cardiac Death Risk"; U.S. Pat. No. 9,655,536, entitled "Non-invasive Method and System for Characterizing Cardiovascular Systems"; U.S. Pat. No. 9,289,150, entitled "Non-invasive Method and System for Characterizing Cardiovascular Systems"; U.S. Pat. No. 8,923,958, entitled "System and Method for Evaluating an Electrophysiological Signal"; U.S. Publication No. 2017/0119272, entitled "Method and Apparatus for Wide-Band Phase Gradient Signal Acquisition"; U.S. application Ser. No. 15/633,330, entitled "Noninvasive Method and System for Measuring Myocardial Ischemia, Stenosis Identification, Localization and Fractional Flow Reserve Estimation"; and U.S. application Ser. No. 15/712,104, entitled "Method and System for Visualization of Heart Tissue at Risk"; each of which are incorporated by reference herein in its entirety.

The wide-band phase gradient signal data generated by the exemplified embodiments may be used, as noted above, as inputs for various phase space techniques and analyses that may in turn be used and performed to generate clinically useful information for assessing the state of the patient's health as well as to, e.g., pinpoint and distinguish disease states and their status as well as for predicting possible disease onset, whether it be in the cardiac or brain fields (such as when wide-band cardiac or cerebral phase gradient signals are used), the oncological field, the prenatal field, or any other medical field in which all or a portion of full spectrum of physiologic signals emitted from the human or other mammalian body could be so used. For example, such clinically useful information may be then further analyzed and transformed into any number of reports, data sets, presentations, etc. (in any number of formats including but not limited to digital formats for presentation via a smartphone or computer, paper report formats, presentation slide formats, or other) for review by a physician and/or presentation to a patient. Such data may be used, for example, by the physician to recommend further testing and/or treatment for the patient. Examples of methods and systems that could be used to collect and process physiologic signals as discussed herein may be found in co-owned and above-referenced U.S. Provisional Patent Application Ser. No. 62/340, 410 filed May 23, 2016 and entitled "Method and System for Collecting Phase Signals for Phase Space Tomography Analysis", the entirety of which is incorporated herein by reference. As such, the present invention contemplates methods and systems for utilizing the biosignal acquisition instruments described herein to acquire and process any type of mammalian physiological signal into wide-band phase gradient signal data that may be then further processed using various phase space techniques and analyses described herein and for in turn generating data and/or reports based on such techniques and analyses, in any number of formats, that include clinically relevant and useful information for the patient and his/her physician.

Figures 12A, 12B:
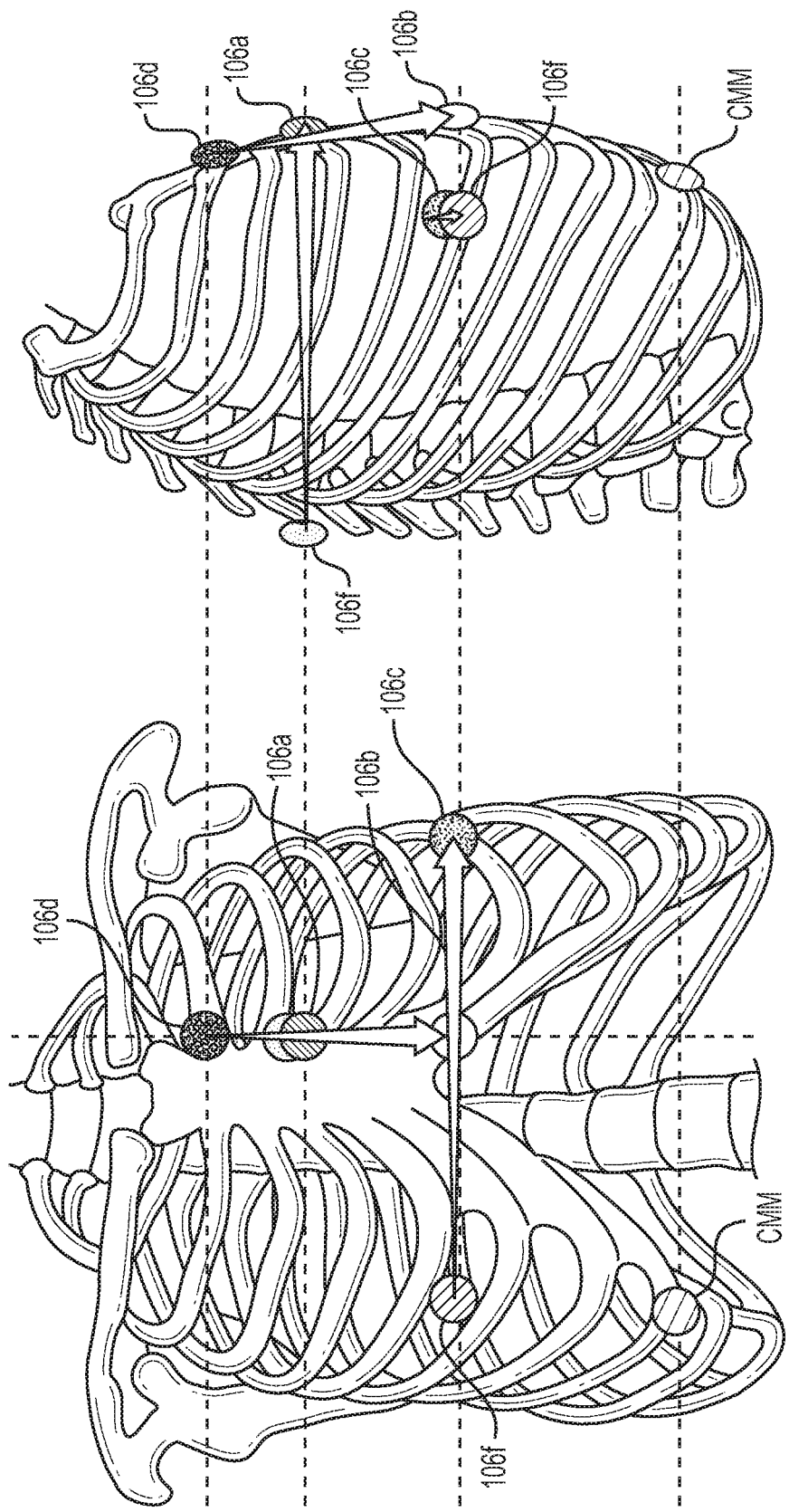
FIGS. 12A and 12B are diagrams of an example placement of the surface electrodes at the chest and back of a patient to acquire bio-potential signals associated with differentially-acquired wide-band cardiac phase gradient signal data in accordance with an illustrative embodiment.

FIGS. 12A and 12B are diagrams of an example placement of the surface electrodes 106a-106g at the chest and back of a patient to acquire bio-potential signals associated with wide-band cardiac phase gradient signals in accordance with an illustrative embodiment. FIG. 12A shows a front view of placement of the surface electrodes 106a-106g to the chest and back of the patient. FIG. 12B shows a side view of placement of the surface electrodes 106a-106g to the same. As shown, the surface electrodes are positioned at i) a first location proximal to a Right anterior axillary line corresponding to a 5th intercostal space; ii) a second location proximal to a Left anterior axillary line corresponding to the 5th intercostal space; iii) a third location proximal to a Left sternal border corresponding to a 1st intercostal space; iv) a fourth location proximal to the Left sternal border below the sternum and lateral to a xiphoid process; v) a fifth location proximal to the Left sternal border corresponding to a 3rd intercostal space; vi) a sixth location proximal to a Back directly opposite of the fifth location and left of a spine; and viii) a seventh location proximal to a Right upper quadrant corresponding to a 2nd intercostal space along a Left axillary line. A common lead (shown as "CMM") is also shown.

FIGS. 12A and 12B also show example acquisition points of the differential measurements that is acquired by the BSA instrument.

It is contemplated that in addition to acquisition of wide-band cardiac phase gradient signals, the exemplified system 100 may be used to acquire wide-band cerebral phase gradient signals.

FIG. 13 is an example operation of BSA instrument or device 1100 (shown as "BioSignal Acquisition Device" 100) in accordance with an illustrative embodiment. As shown in FIG. 13, the BSA instrument 1100 is configured to acquire a wide-band cardiac phase gradient signal 116 from a patient 108. Each BSA instrument 1100 is operatively coupled a wireless communication device 1302 that is configured to transmit the acquired wide-band cardiac phase gradient signal data 116 to a data repository 1304 (shown as "MDDS 1304" (Medical Device Data System)) that is connected to a plurality of BSA instrument 100. The wide-band cardiac phase gradient signal data 116 of each BSA instrument 1100 is stored at the repository 1304 and is subsequently analyzed, e.g., by a processing center 1306. The output of the analysis is stored in a diagnosis repository 1308 that is accessible to clinicians, via client devices 1310, from a portal 1312 operatively coupled to the diagnosis repository 1308.

Having thus described several embodiments of the present disclosure, it will be rather apparent to those skilled in the art that the foregoing detailed disclosure is intended to be presented by way of example only, and is not limiting. Many advantages for non-invasive method and system for location of an abnormality in a heart have been discussed herein. Various alterations, improvements, and modifications will occur and are intended to those skilled in the art, though not expressly stated herein. These alterations, improvements, and modifications are intended to be suggested hereby, and are within the spirit and the scope of the present disclosure.

In some embodiments, acquisition of biopotential signals associated with wide-band phase gradient signals may be performed at other parts of the body to diagnose various disease and conditions. For example, the exemplified system may be used to acquire biopotential signals associated with wide-band phase gradient signals for oncology. The exemplified system may be used to acquire biopotential signals associated with wide-band phase gradient signals for monitoring pre-natal development.

It is contemplated that the exemplified methods and systems can be used to acquire biosignals from any type of mammals and animals including test animals for research and clinical purposes as well as for the treatment of animals in veterinary purposes.

Additionally, the recited order of the processing elements or sequences, or the use of numbers, letters, or other designations therefore, is not intended to limit the claimed processes to any order except as may be specified in the claims. Accordingly, the present disclosure is limited only by the following claims and equivalents thereto.

The exemplary analyses can be used to identify various pathologies and conditions including, but not limited to: heart disease, cardiac arrhythmia, diabetic autonomic neuropathy, Parkinson's disease, forms of epilepsy, brain injury, altered states of cognition, stability of a heart at different heart rates, effectiveness of medication, ischemia, silent ischemia, atrial fibrillation, ventricular fibrillation, ventricular tachycardia, blood vessel blockages, attention deficit disorder, etc.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

These various components discussed herein are merely examples of components that could work in these embodiments and other components may also be used.

What is claimed is:

1. An apparatus comprising:
a plurality of bio-signal acquisition channels, each bio-signal acquisition channel comprising a gain amplifier configured to, by bipolar sensing for each input, amplify differential biopotential signals received from a pair of associated surface electrodes placed on a patient to generate a differential wide-band cardiac phase gradient signal, wherein each differential biopotential signal is amplified without filtering that causes distortion in the generated wide-band cardiac phase gradient signal above 1 kHz, each output of the bio-signal acquisition channels feeding an analog-to-digital conversion circuit that simultaneously samples, each of bio-signal acquisition channels to generate a differential wide-band cardiac phase gradient signal data set,
wherein the generated differential wide-band cardiac phase gradient signal data set or a portion thereof is analyzed, in a phase-associated analysis, along with a data set associated with oxygen saturation readings concurrently acquired with the biopotential signals of the plurality of bio-signal acquisition channels, to generate an output data set in a report and/or a display, and wherein the output data set is used in a diagnosis of cardiac disease.

2. The apparatus of claim 1, further comprising:
a potential biasing circuit configured to actively drive the patient via a potential to shunt environmental noise currents flowing in the patient.

3. The apparatus of claim 1, comprising:
a potential biasing circuit configured to actively drive the patient via a constant positive potential so as to shunt environmental noise currents flowing in the patient.

4. The apparatus of claim 1, comprising:
a potential biasing circuit configured to actively drive the patient to a constant negative potential so as to shunt environmental noise currents flowing in the patient.

5. The apparatus of claim 2, wherein the potential biasing circuit comprises:
a waveform generator; and
a drive circuit configured to couple to the waveform generator and to actively drive the patient to an alternating potential so as to shunt environmental noise currents flowing in the patient.

6. The apparatus of claim 5, wherein the potential biasing circuit is configured to actively drive the patient to an alternating potential having a minimum magnitude greater than a DC bias value associated with one or more of the surface electrodes placed on the patient.

7. The apparatus of claim 6, comprising:
a potential biasing circuit configured actively drive the patient to a potential so as to shunt environmental noise currents flowing in the patient, wherein a portion of the varying potential is negative.

8. The apparatus of claim 1, comprising:
a terminal block comprising a connector configured to couple one or more cables terminating with one or more corresponding surface electrodes, wherein each of the one or more cables comprises a shield layer that encapsulates one or more signal wires that carries a given biopotential signal received from a given surface electrode; and
a noise-rejection circuit having an output coupled to a shield layer for each of the one or more cables to apply a potential of the potential biasing circuit.

9. The apparatus of claim 1, comprising:
a terminal block comprising one or more connectors configured to couple to one or more cables each associated with a given surface electrode, wherein each of the one or more cable comprises a shield layer that encapsulates one or more signal wires that carries a given biopotential signal received from the given surface electrode; and
a noise-rejection circuit having an input that receives the given biopotential signal that is carried over the one or more signal wires, the rejection circuit having an output that couples, through the one or more connectors, to the shield layer for each of the one or more cable to apply a potential corresponding to the received biopotential signal.

10. The apparatus of claim 8, wherein the bio-signal acquisition channels comprise a number of channels selected from the group consisting of 1, 2, 3, 4, 5, 6, 7, 8, 9, 10, 11, and 12.

11. The apparatus of claim 8, wherein the plurality of bio-signal acquisition channels comprise three differential channels.

12. The apparatus of claim 8, further comprising:
a plurality of analog-to-digital circuits, each corresponding to a bio-signal acquisition channel, wherein each output of the each bio-signal acquisition channel feeds a corresponding analog-to-digital circuit, and wherein the analog-to-digital circuits simultaneously sample to generate a plurality of wide-band cardiac phase gradient signal data streams each associated with a given differential wide-band cardiac phase gradient signal.

13. The apparatus of claim 12, wherein the gain amplifier and the plurality of analog-to-digital circuits are part of a same integrated circuit.

14. The apparatus of claim 1, wherein the plurality of bio-signal acquisition channels are located on a multi-layer printed circuit board, multi-layer printed circuit board comprising:
a first layer that serves as a reference ground plane;
a second layer co-planar to the first layer that serves as a cable-shield drive voltage plane; and
one or more signal layers having a pair of conductive traces running therethrough and across one or more regions coincident and coplanar to the second ground layer, wherein the pair of conductive traces electrically couple, across a connector directly or indirectly affixed to the multi-layer printed circuit, ends of at least two signal-carrying conductors to differential input pins of an analog-to-digital conversion and amplifier stage mounted on a surface of the multi-layer printed circuit, wherein a first signal-carrying conductor of the at least two signal-carrying conductors is associated with a first cable and a second signal-carrying conductor of the at least two signal-carrying conductors is associated with a second cable;

wherein the second ground layer electrically couples, over the at least one connector, i) a first outer conductor that serves as an outer shield of the first cable and ii) a second outer conductor that serves as an outer shield of the second cable, so as to drive potentials of the first outer conductor and the second outer conductor to that of the cable-drive voltage plane.

15. The apparatus of claim 14, wherein the first cable and the second cable terminate at a single cable-pin connector, the single cable-pin connector having a coupling element configured to releasably mate to the connector of the signal acquisition board.

16. The apparatus of claim 14, wherein the pair of conductive traces are arranged, on a same set of signal layers of the one or more signal layers, and in close proximity to one another such that lengths, or a portion thereof, of each conductive trace of the pair of conductive traces are parallel to one another.

17. The apparatus of claim 14, wherein each conductive trace of the pair of conductive traces has a length and have a same number of via so as to have a similar impedance characteristics as one another.

18. The apparatus of claim 14, wherein each conductive trace of the pair of conductive traces includes an impedance element arranged between a respective pin of the connector and a respective differential input pins of the analog-to-digital conversion circuit, and wherein the pair of conductive traces has a capacitance element coupled therebetween to form, with the impedance elements, an antialiasing filter.

19. The apparatus of claim 14, wherein the multi-layer printed circuit board further comprises a conductive housing that serves as a grounded shield cage, wherein the conductive housing spans a portion of the second ground layer so as to encapsulate a portion of the pair of conductive traces, and wherein the conductive housing is affixed to the surface of the multi-layer printed circuit and is electrically coupled to the reference ground plane.

20. The apparatus of claim 14, wherein the multi-layer printed circuit board further comprises:

one or more processors and one or more memory components coupled to the one or more processors, wherein the one or more processors and the one or more memory components are arranged on a portion of the surface of the multi-layer printed circuit that do not coincide or overlap with the cable-drive voltage plane of the second layer.

21. The apparatus of claim 14, wherein the pair of conductive traces forms a part of a first differential input channel of the signal acquisition board.

22. The apparatus of claim 14, further comprising:

a second differential input channel and a third differential input channel, wherein each of the second differential input channel and the third differential input channel comprises a pair of conductive traces running through the one or more signal layers across the one or more regions coincident and coplanar to the cable-drive voltage plane of the second ground layer, wherein each of the second differential input channel and the third differential input channel connects to a pair of cables having at least one signal-carrying conductor and an outer conductor that serves as an outer shield of the signal-carrying conductor, and wherein the cable-drive voltage plane electrically couples, over the at least one connector, to the outer conductors of the pair of cables so as to drive potentials of the outer conductors to that of the cable-drive voltage plane.

\* \* \* \* \*